(12) United States Patent
Mohan

(10) Patent No.: US 12,012,431 B2
(45) Date of Patent: Jun. 18, 2024

(54) METHODS OF PREPARING 1'-CYANO NUCLEOSIDES

(71) Applicant: Gilead Sciences, Inc., Foster City, CA (US)

(72) Inventor: Sankar Mohan, Edmonton (CA)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/108,480

(22) Filed: Feb. 10, 2023

(65) Prior Publication Data

US 2023/0295214 A1 Sep. 21, 2023

Related U.S. Application Data

(62) Division of application No. 17/198,829, filed on Mar. 11, 2021, now Pat. No. 11,613,553.

(60) Provisional application No. 62/988,661, filed on Mar. 12, 2020.

(51) Int. Cl.
*C07H 19/23* (2006.01)
*C07H 1/00* (2006.01)

(52) U.S. Cl.
CPC ............ *C07H 19/23* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 4,816,570 A | 3/1989 | Farquhar |
| 4,968,788 A | 11/1990 | Farquhar |
| 5,663,159 A | 9/1997 | Starrett, Jr. et al. |
| 5,792,756 A | 8/1998 | Starrett, Jr. et al. |
| 6,312,662 B1 | 11/2001 | Erion et al. |
| 6,475,985 B1 | 11/2002 | Wagner et al. |
| 6,476,030 B1 | 11/2002 | Carling et al. |
| 6,639,059 B1 | 10/2003 | Kochkine et al. |
| 6,656,915 B1 | 12/2003 | Bantia et al. |
| 6,909,011 B2 | 6/2005 | Skranc et al. |
| 7,078,403 B1 | 7/2006 | Wu et al. |
| 7,105,493 B2 | 9/2006 | Sommadossi et al. |
| 7,125,855 B2 | 10/2006 | Bhat et al. |
| 7,166,604 B2 | 1/2007 | Watson et al. |
| 7,176,203 B2 | 2/2007 | Chambers et al. |
| 7,268,119 B2 | 9/2007 | Cook et al. |
| 7,285,658 B2 | 10/2007 | Cook et al. |
| 7,368,437 B1 | 5/2008 | Bojack et al. |
| 7,390,791 B2 | 6/2008 | Becker et al. |
| 7,429,571 B2 | 9/2008 | Chand et al. |
| 7,514,410 B2 | 4/2009 | Babu et al. |
| 7,560,434 B2 | 7/2009 | Babu et al. |
| 7,598,230 B2 | 10/2009 | Cook et al. |
| 7,608,597 B2 | 10/2009 | Sommadossi et al. |
| 7,713,941 B2 | 5/2010 | Cook et al. |
| 7,803,788 B2 | 9/2010 | Becker et al. |
| 7,807,653 B2 | 10/2010 | Cook et al. |
| 7,842,672 B2 | 11/2010 | Boojamra et al. |
| 7,951,787 B2 | 5/2011 | McGuigan |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,568 B2 | 12/2011 | Narjes et al. |
| 8,119,607 B2 | 2/2012 | Francom et al. |
| 8,242,085 B2 | 8/2012 | Babu et al. |
| 8,318,682 B2 | 11/2012 | Butler et al. |
| 8,415,308 B2 | 4/2013 | Cho et al. |
| 8,455,451 B2 | 6/2013 | Cho et al. |
| 8,853,171 B2 | 10/2014 | Butler et al. |
| 8,871,737 B2 | 10/2014 | Smith et al. |
| 8,889,159 B2 | 11/2014 | Clearly et al. |
| 8,980,865 B2 | 3/2015 | Wang |
| 9,090,642 B2 | 7/2015 | Cho et al. |
| 9,243,022 B2 | 1/2016 | Beigelman et al. |
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,938,283 B2 | 4/2018 | Pandey et al. |
| 9,949,994 B2 | 4/2018 | Chun et al. |
| 10,023,600 B2 | 7/2018 | Butler et al. |
| 10,034,893 B2 | 7/2018 | Luly et al. |

(Continued)

FOREIGN PATENT DOCUMENTS

| | | |
|---|---|---|
| CN | 108084192 | 5/2018 |
| CN | 110330540 | 10/2019 |

(Continued)

OTHER PUBLICATIONS

"Molecular Nuclear Medicine," First Edition, Wang (ed.), May 31, 2001, 8 pages.

(Continued)

*Primary Examiner* — Layla D Berry

(74) *Attorney, Agent, or Firm* — Fish & Richardson P.C.

(57) ABSTRACT

The present disclosure generally describes methods of preparing 1'-cyano nucleosides, such as a compound of Formula (I). For example, the compound of Formula (I) can be prepared from a compound of Formula (II-a) in a flow reactor.

20 Claims, 2 Drawing Sheets

(56) References Cited

U.S. PATENT DOCUMENTS

| | | |
|---|---|---|
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,225,508 B1 | 1/2022 | Baric et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,377,456 B2 | 7/2022 | Souza et al. |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 11,660,307 B2 | 5/2023 | Cihlar et al. |
| 11,701,372 B2 | 7/2023 | Ellis et al. |
| 11,780,844 B2 | 9/2023 | Bartlett et al. |
| 11,814,406 B2 | 10/2023 | Bunyan et al. |
| 11,845,755 B2 | 12/2023 | Bartlett et al. |
| 11,851,438 B2 | 12/2023 | Bartlett et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0129437 A1 | 5/2010 | Gaillard |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0023745 A1 | 1/2019 | Baric et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | Clarke et al. |
| 2021/0403497 A1 | 12/2021 | Butler et al. |
| 2022/0081462 A1 | 3/2022 | Bunyan et al. |
| 2022/0175805 A1 | 6/2022 | Cihlar |
| 2022/0280549 A1 | 9/2022 | Larson et al. |
| 2022/0354873 A1 | 11/2022 | Axt et al. |
| 2022/0356196 A1 | 11/2022 | Byun et al. |
| 2023/0027727 A1 | 1/2023 | Clarke et al. |
| 2023/0040586 A1 | 2/2023 | Byun et al. |
| 2023/0125751 A1 | 4/2023 | Mackman et al. |
| 2023/0151043 A1 | 5/2023 | Bunyan et al. |
| 2023/0233587 A1 | 7/2023 | Cihlar |
| 2023/0279013 A1 | 9/2023 | Bartlett et al. |
| 2023/0279014 A1 | 9/2023 | Bartlett et al. |
| 2023/0279015 A1 | 9/2023 | Bartlett et al. |
| 2023/0295172 A1 | 9/2023 | Bartlett et al. |
| 2023/0322813 A1 | 10/2023 | Chun et al. |
| 2023/0346812 A1 | 11/2023 | Cihlar et al. |
| 2023/0348519 A1 | 11/2023 | Brak et al. |
| 2024/0009220 A1 | 1/2024 | Bannister et al. |
| 2024/0024341 A1 | 1/2024 | Ellis et al. |

FOREIGN PATENT DOCUMENTS

| | | |
|---|---|---|
| CN | 110724174 | 1/2020 |
| CN | 110776512 | 2/2020 |
| CN | 111171078 | 5/2020 |
| CN | 111205294 | 5/2020 |
| CN | 111205327 | 5/2020 |
| CN | 111233869 | 6/2020 |
| CN | 111265532 | 6/2020 |
| CN | 111440176 | 7/2020 |
| CN | 111548384 | 8/2020 |
| CN | 111961057 | 11/2020 |
| CN | 112778310 | 5/2021 |
| CN | 113185519 | 7/2021 |
| CN | 113248508 | 8/2021 |
| CN | 113292565 | 8/2021 |
| CN | 113387954 | 9/2021 |
| CN | 114437159 | 5/2022 |
| CN | 114621229 | 6/2022 |
| IN | 202011021676 | 11/2021 |
| JP | 2005185235 | 7/2005 |
| JP | 2005187428 | 7/2005 |
| WO | WO1991019721 | 12/1991 |
| WO | WO1999045029 | 9/1999 |

(56) References Cited

FOREIGN PATENT DOCUMENTS

| | | |
|---|---|---|
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013039861 | 3/2013 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017165489 | 9/2017 |
| WO | WO2017184668 | 10/2017 |
| WO | WO2018085307 | 5/2018 |
| WO | WO2018099946 | 6/2018 |
| WO | WO2018121678 | 7/2018 |
| WO | WO2018145148 | 8/2018 |
| WO | WO2018204198 | 11/2018 |
| WO | WO2018217906 | 11/2018 |
| WO | WO2019014247 | 1/2019 |
| WO | WO2019053696 | 3/2019 |
| WO | WO2019079594 | 4/2019 |
| WO | WO2019113462 | 6/2019 |
| WO | WO2021021717 | 2/2021 |
| WO | WO2021040356 | 3/2021 |
| WO | WO2021050961 | 3/2021 |
| WO | WO2021102363 | 5/2021 |
| WO | WO2021147236 | 7/2021 |
| WO | WO2021154530 | 8/2021 |
| WO | WO2021175296 | 9/2021 |
| WO | WO2021188915 | 9/2021 |
| WO | WO2021195661 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2022008642 | 1/2022 |
| WO | WO2022029704 | 2/2022 |
| WO | WO2022047065 | 3/2022 |
| WO | WO2022047441 | 3/2022 |
| WO | WO2022081870 | 4/2022 |
| WO | WO2022093895 | 5/2022 |
| WO | WO2022165386 | 8/2022 |
| WO | WO2022174194 | 8/2022 |
| WO | WO2022197950 | 9/2022 |
| WO | WO2022217153 | 10/2022 |
| WO | WO2022217154 | 10/2022 |
| WO | WO2022217155 | 10/2022 |
| WO | WO2022251663 | 12/2022 |
| WO | WO2023009977 | 2/2023 |
| WO | WO2023056335 | 4/2023 |
| WO | WO2023122212 | 6/2023 |
| WO | WO2023167938 | 9/2023 |
| WO | WO2023239665 | 12/2023 |

OTHER PUBLICATIONS

"Veterinary Microbiology," 4th Edition, Lu (ed.), 2007, p. 304: paragraph 2, p. 408: paragraph 1, p. 419: paragraphs 1-2, 4 pages.

Adlington et al., "Synthesis of novel C-nucleosides with potential applications in combination and parallel synthesis," Tetrahedron Letters, 2000, 41:575-578.

(56) References Cited

OTHER PUBLICATIONS

Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.
Aleissa et al., "New Perspectives on Antimicrobial Agents: Remdesivir Treatment for COVID-19," Antimicrobial Agents and Chemotherapy, Dec. 2020, 65(1): 18 pages.
Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters. Bulletin of Environmental Contamination and Toxicology, 2000, pp. 415-420, vol. 65, No. 4.
Anderson et al., "The use of convalescent plasma therapy and remdesivir in the successful management of a critically ill obstetric patient with novel coronavirus 2019 infection: A case report," Case Reports in Women's Health, May 2020, 27: 3 pages.
Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop- remdesivir-with-gilead-thanks-to-37-5m-from-nih>, Mar. 1, 2020, 5 pages.
Anonymous, "Gillings research on broad-spectrum antiviral could aid public health response to coronavirus outbreaks"—UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Baker et al., "Prodrugs of 9-Beta-D-Arabinofuranosyladenine. 1. Synthesis and Evaluation of some 5'-(O-Acyl) Derivatives," Journal of Medicinal Chemistry, Dec. 1978, 21(12): 1218-1221.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.
Bandini, et al., Indium tribromide: a highly effective catalyst for the addition of trimethylsilyl cyanide to a-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Barl, et al., The halogen/magnesium-exchange using iPrMgCl•LiCl and related exchange reagents, Heterocycles, Jan. 2014, pp. 827-844, vol. 88, No. 2.
Beer et al., "Characteristics of Filoviridae: Marburg and Ebola Viruses," Naturwissenschaften, 1999, 86:8-17.
Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.
Beigel et al., "Remdesivir for the Treatment of Covid-19—Final Report," New England Journal of Medicine, Nov. 5, 2020, 383(19): 1813-1826.
Belokon et al., "Optimized catalysts for the asymmetric addition of trimethylsilyl cyanide to aldehydes and ketones," Tetrahedron, 2001, 57: 771-779.
Benksim et al., "A Novel Stereospecific Synthesis of Glycosyl Cyanides from 1,2-O-sulfinyl Derivatives," Organic Letters, 2004, 6(22): 3913-3915.
Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.
Bio et al., "Practical Synthesis of a Potent Hepatitis C Virus RNA Replication Inhibitor," J. Org. Chem., 2004, 69(19): 6257-6266.
Bobeck et al., "Advances in Nucleoside Monophosphate Prodrugs as Anti-HCV Agents," Antiviral Therapy, 2010, 15: 935-950.
Bobrowski et al., "Synergistic and Antagonistic Drug Combinations against SARS-COV-2", Molecular Therapy, Feb. 2021, 29(2):873-885.
Bojack, et al., Design and Synthesis of Inhibitors of Adenosine and AMP Deaminases, Organic Letters, 2001, pp. 839-842, vol. 3, No. 6.
Bowie et al., "RIG-I: tri-ing to discriminate between self and non-self RNA," Trends in Immunology, Apr. 2007, 28(4): 147-150.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
Brands et al., "Crystallization-Induced Diastereomer Transformations," Chem. Rev., 2006, 106(7): 2711-2733.
Brittain, Polymorphism in Pharmaceutical Solids, 2nd Edition, 2009, pp. 183-226, Informa Healthcare USA, Inc.
Brotschi et al., "Bipyridyl and biphenyl DNA: A recognition motif based on interstrand aromatic stacking," Chemistry—A European Journal, 2005, 11(6):1911-1923.
Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.
Brown, "Progress towards improving antiviral therapy for hepatitis C virus polymerase inhibitors", Part O: Nucleoside analogues, 2009, 18: 709-725.
Bullard-Feibelman et al., "The FDA-approved drug Sofosbuvir inhibits Zika Virus infection." Antiviral Res., Jan. 1, 2018, 137: 134-140.
Burns, "A Glimmer of Hope for Fatal Feline Disease," JAVMAnews, Dec. 15, 2017, 5 pages.
Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.
Cabirol et al., Robust and Efficient, yet Uncatalyzed, Synthesis of Triarylsilyl-protected Cyanohydrins from Ketones, 2008, pp. 2446-2449, vol. 73.
Caira, "Crystalline Polymorphism of Organic Compounds." Topics in Current Chemistry, 1998, 198: 163-208.
Cales et al., "Treatment of liver fibrosis: clinical aspects," Gastroentérologie Clinique et Biologique, 2009, 33(10-11): 958-966.
Calisher et al., "Antigenic Relationships between Flaviviruses as Determined by Cross-neutralization Tests with Polyclonal Antisera," Journal of General Virology, 1989, 70: 37-43.
Camps, "Studies on Structurally Simple-αβ-butenolides-II," Tetrahedron, 1982, 38(15): 2395-2402.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.

(56) References Cited

OTHER PUBLICATIONS

Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRe, retrieved on Jul. 29, 2021, retrieved from URL <"https://www.chemsrc.com/en/cas/4298-15-1_589766.html"> 4 pages.
CAS No. 54-05-7, "Chloroquine", ChemSRe, retrieved on Jul. 29, 2021, retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-, 2-ethylbutyl ester, 6-ester with 2-C-(4-aminopyrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_m=1809249-37-3">, 3 pages.
Chapman et al., "RSV604, a Novel Inhibitor of Respiratory Syncytial Virus Replication," Antimicrobial Agents and Chemotherapy, 2007, 51(9): 3346-3353.
Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.
Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.
Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.
Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.
Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.
Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.
Cox et al., "Therapeutically administered ribonucleoside analogue MK-4482/EIDD-2801 blocks SARS-CoV-2 transmission in ferrets," Nature Microbiology, 2020, 6(1): 11-18.
Dai et al., "Synthesis of 2'-C-β-Fluoromethyluridine," Organic Letters, 2003, 5(6): 807-810.
Damont et al., "Synthesis of 1'-C-Fluoromethyladenosine," Nucleosides, Nucleotides , and Nucleic Acids, 2007, 26:1431-1434.
Dande et al., "Remdesivir in a pregnant patient with COVID-19 pneumonia," Journal of Community Hospital Internal Medicine Perspectives, Jan. 2021, 11(1): 103-6.
De Clercq, "Antiviral Drugs: Current State of the Art," J. Clin. Virol., 2001, 22(1): 73-89.
De Clercq, "Molecular Targets for Antiviral Agents," The Journal of Pharmacology and Experimental Therapeutics, 2001, 297(1): 1-10.
De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.
De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.
De Wit et al., "Prophylactic and Therapeutic Remdesivir (GS-5734) Treatment in the Rhesus Macaque Model of MERS-CoV Infection," Proceedings of the National Academy of Sciences of the United States of America, Mar. 2020, 117(12): 6771-6776.
Di Bisceglie et al., "The Unmet Challenges of Hepatitis C," Scientific American, Oct. 1999, pp. 80-85.
Dinnon et al., "A mouse-adapted model of SARS-CoV-2 to test COVID-19 countermeasures, " Nature, Aug. 2020, 586: 560-566.
Dolzhenko et al., "Pyrazolo[1,5-a][1,3,5]Triazines(5-Aza-9-Deazapurines): Synthesis and Biological Activity," Heterocycles, 2008, 75(7): 1575-1622.
Domingo et al., "The quasispecies (extremely heterogeneous) nature of viral RNA genome populations: biological relevance—a review," Gene, 1985, 40: 1-8.
Dondoni et al., "Thiazole-Based Synthesis of Formyl C-Glycosides," Journal of Organic Chemistry, 1994, 59: 6404-6414.
Douafer et al., "Scope and limitations on aerosol drug delivery for the treatment of infectious respiratory diseases," Journal of Controlled Release, Sep. 2020, 325: 276-292.
Dudfield et al., "Synthesis of C-ribosyl imidazo[2,1-f][1,2,4]triazines as inhibitors of adenosine and AMP deaminases," J. Chem. Soc, Perkin Trans I, 1999, pp. 2929-2936.
Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Dymock et al., "Novel approaches to the treatment of hepatitis C virus infection," Antiviral Chemistry & Chemotherapy, 2000, 11(2): 79-96.
Easterlin et al., "Extremely Preterm Infant Born to a Mother With Severe COVID-19 Pneumonia." Journal of Investigative Medicine High Impact Case Reports, Jul. 2020, 8: 1-5.
El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.
Farquhar et al., "Biologically Reversible Phosphate-Protective Groups," Journal of Pharmaceutical Sciences, 1983, 72(3): 324-325.
Fauquet et al., "Abbreviations for vertebrate virus species names", Archives of Virology, Dec. 31, 1999, pp. 1865-1880.
fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.
Flint et al., "Functional analysis of cell surface-expressed hepatitis C virus E2 glycoprotein," J. Virol., Aug. 1999, 73(8): 6782-6790.
Foster et al., "Deuterium isotope effects in studies of drug metabolism," Trends in Pharmacological Sciences, Jan. 1984, 5:524-527.
Franchetti et al., "Antitumor Activity of C-Methyl-β-D-ribofuranosyladenine Nuceoside Ribonuccotide Reductase Inhibitors," J. Med. Chem. 2005, 48: 4983-4989.
Freeman et al., "3 Prodrug Design for Phosphates and Phosphonates," Progress in Medicinal Chemistry, 1997, 34: 111-147.
Fukumoto et al., "Viral Dynamics of Hepatitis C Early After Orthotopic Liver Transplantation: Evidence for Rapid Turnover of Serum Virions," Hepatology, 1996, 24: 1351-1354.
Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.
Gardelli et al., "Phosphoramidate Prodrugs of 2'-C-Methylcytidine for Therapy of Hepatitis C Virus Infection," Journal of Medicinal Chemistry, 2009, 52(17): 5394-5407.
George et al., "Preparation of silyl- and germylmetallic compounds," Journal of the American Chemical Society, Jan. 1960, 82(2):403-6.

(56) References Cited

OTHER PUBLICATIONS

Gil et al., "COVID-19: Drug Targets and Potential Treatments," Journal of Medicinal Chemistry, Jun. 2020, 63(21): 12359-12386.
Gleeson et al., "Prediction of the Potency of Inhibitors of Adenosine Deaminase by QM/MM Calculations," Chem. Commun., 2003, pp. 2180-2181.
Gordon et al., "Control of Hepatitis C: A Medicinal Chemistry Perspective," J. Med. Chem., 2005, pp. 1-20, vol. 48, No. 1.
Gordon et al., "Remdesivir is a direct-acting antiviral that inhibits RNA-dependent RNA polymerase from severe acute respiratory syndrome coronavirus 2 with high potency," J. Biol. Chen., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Greene et al., "Protective Groups in Organic Synthesis," John Wiley & Sons., 1991, pp. 118-142.
Greene et al., "Protective Groups in Organic Synthesis," published by John Wiley & Sons, v Inc., 1991, pp. 1-4, 10-14, 47-53 and 100-103.
Grein et al., "Compassionate Use of Remdesivir for Patients with Severe Covid-19", The New England Journal of Medicine, Apr. 2020, 382(24): 2327-2336.
Gudmundsson et al., "Synthesis of imidazo[1,2-a]pyridine C-Nucleosides with an Unexpected Site of Ribosylation," Journal of Organic Chemistry, 1997, 62: 3453-3459.
Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.
Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.
Hamann et al., "Synthesis and antiviral evaluation of 7,9-dideaza-8-thiapurine C-nucleoside derivatives," Collection Symposium Series, 2008, 10: 347-349.
Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.
Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.
Haraguchi et al., "Stereoselective Synthesis of 1'-C-Branched Uracil Nucleosides From Uridine," Nucleosides & Nucleotides, 1995, 14(3-5): 417-420.
Harcourt et al., "Molecular Characterization of the Polymerase Gene and Genomic Termini of Nipah Virus," Virology, 2001, 287: 192-201.
Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.
Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.
Hecker et al., "Liver Targeted Prodrugs of 2'-C-Methyladenosine for Therapy of Hepatitis C Virus Infection." J. Med. Chem., 2007, 50(16): 3891-3896.
Hoffmann et al., "When, in the context of drug design, can a fluorine atom successfully substitute a hydroxyl group?," International Journal of Quantum Chemistry, 2002, 89: 419-427.
Holshue et al., "First Case of 2019 Novel Coronavirus in the United States", The New England Journal of Medicine, Jan. 2020, 9 pages.
Huang et al., "Recent development of therapeutics for chronic HCV infection," Antiviral Research, Sep. 2006, 71(2-3): 351-362.

Igbinosa et al., "Use of remdesivir for pregnant patients with severe novel coronavirus disease 2019," American Journal of Obstetrics & Gynecology, Aug. 2020, 223(5): 768-770.
Itoh et al., "Divergent and Stereocontrolled Approach to the Synthesis of Uracil Nucleosides Branched at the Anomeric Position," J. Org. Chem, 1995, 60: 656-662.
Jacobson et al., "Use of dexamethasone, remdesivir, convalescent plasma and prone positioning in the treatment of severe COVID-19 infection in pregnancy: A case report," Case Reports in Women's Health, Jan. 2021, 29: 3 pages.
Jasko et al., "5'-Phosphonates of Ribonucleosides and 2'-Deoxyribonucleosides: Synthesis and Antiviral Activity," Nucleosides & Nucleotides, 1993, 12(8): 879-893.
Joseph [online]. "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.
Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.
Kaewkhao et al., "High sensitivity methods to quantify chloroquine and its metabolite in human blood samples using LC-MS/MS", Bioanalysis, Mar. 2019, 11(5):333-347.
Kalil et al., "Baricitinib plus Remdesivir for hospitalized adults with Covid-19," New England Journal of Medicine, Dec. 11, 2020, 13 pages.
Khamnei et al., "Neighboring Group Catalysis in the Design of Nucleotide Prodrugs," J. Med. Chem., 1996, 39(20): 4109-4115.
Khan et al., "Coronaviruses disease 2019 (COVID-19): Causative agent, mental health concerns, and potential management options," Journal of Infection and Public Health, Dec. 2020, 13(12):1840-1844.
Kim et al., "Reversal of the Progression of Fatal Coronavirus Infection in Cats by a Broad-Spectrum Coronavirus Protease Inhibitor," PLOS Pathogens, Mar. 30, 2016, 18 pages.
Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.
Knaggs et al., A QSAR Study Investigating the Effect of L-Alanine Ester Variation on the Anti-HIV Activity of Some Phosphoramidate Derivatives of d4T, Bioorganic & Medicinal Chemistry Letters. 2000. 10: 2075-2078.
Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.
Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I. 1984, pp. 229-238.
Kobe et al., "Use of Distance Geometry Approach for the In Vitro Antiviral Activity Evaluation of N-bridgehead C-nucleosides," European J. Med. Chem., 1992, 27(3): 259-266.
Koplon [online], "$37.5 million grant will address research of high-priority infections," UAB News, retrieved on Mar. 13, 2023. URL <https://www.uab.edu/news/health/item/10307-37-5-million-grant-will-address-research-of-high-priority-infections>, Mar. 20, 2019, 1 page.
Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.
Kushner et al., "Pharmacological uses and perspectives of heavy water and deuterated compounds," Canadian Journal of Physiology and Pharmacology, Feb. 1999, 77(2):79-88.
Kuzik et al., "Nebulized Hypertonic Saline in the Treatment of Viral Bronchiolitis in Infants", The Journal of Pediatrics, Sep. 2007, 151(3):266-270.e1.

(56) References Cited

OTHER PUBLICATIONS

Lat et al., "Therapeutic options in the treatment of severe acute respiratory syndrome coronavirus 2 in pregnant patient," American Journal of Obstetrics & Gynecology MFM, Nov. 2020, 2(4): 100224.

Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.

Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.

Leyssen et al., "Molecular strategies to inhibit the replication of RNA Viruses," Antiviral Research, 2008, 78:9-25.

Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.

Liu et al., "Hydroxychloroquine, a less toxic derivative of chloroquine, is effective in inhibiting SARS-CoV-2 infection in vitro," Cell Discovery, Mar. 18, 2020, 6:16, 4 pages.

Lo et al., "GS-5734 and its parent nucleoside analog inhibit Filo-, Pneumo-, and Paramyxoviruses," Scientific Reports, 2017, 7(43395):1-7.

Lovelette, ",2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.

Lu, Chengping, Veterinary Microbiology 5th edition, Jan. 31, 2013, p. 431, China Agriculture Press (No English Translation available).

Maldarelli et al., "Remdesivir Treatment for Severe COVID-19 in Third-Trimester Pregnancy: Case Report and Management Discussion," Open Forum Infectious Diseases, Sep. 2020, 7(9): 4 pages.

Martell et al., "Hepatitis C Virus (HCV) Circulates as a Population of Different but Closely Related Genomes: Quasispecies Nature of HCV Genome Distribution," Journal of Virology, 1992, 6695: 3225-3229.

Martin et al., "Hint2, A Mitochondrial Apoptotic Sensitizer Down-Regulated in Hepatocellular Carcinoma," Gastroenterology, Jun. 2006, 130(7): 2179-2188.

Mason et al., "Polyadenylation-dependent screening assay for respiratory syncytial virus RNA transcriptase activity and identification of an inhibitor." Nucleic Acids Research, 2004, 32(16): 4758-4767.

Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.

Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.

McCoy et al., "Compassionate use of remdesivir for treatment of severe coronavirus disease 2019 in pregnant women at a United States academic center," American Journal of Obstetrics & Gynecology MFM, Aug. 2020, 2(Suppl 3): 4 pages.

McGuigan et al. "Application of Phosphoramidate ProTide Technology Significantly Improves Antiviral Potency of Carbocyclic Adenosine Derivatives," J. Med. Chem., 2006, 49: 7215-7226.

McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.

McGuigan et al., "Design, synthesis and biological evaluation of phosphorodiamidate prodrugs of antiviral and anticancer nucleosides," European Journal of Medical Chemistry, 2013, 70: 326-340.

McGuigan et al., "Intracellular Delivery of Bioactive AZT Nucleotides by Aryl Phosphate Derivatives of AZT," J. Med. Chem., 1993, 36(8): 1048-1052.

Mehellou et al., "Aryloxy Phosphoramidate Triesters: a Technology for Delivering Monophosphorylated Nucleosides and Sugars into Cells," ChemMedChem, 2009, 4:1779-1791.

Meppen et al., "Cyclic phosphoramidates as prodrugs of 2'-C-methylcytidine," European Journal of Medicinal Chemistry, 2009, 49(9): 3765-3770.

Meppen et al., "Medi-404—A Prodrug Approach for the Treatment of HCV Infection," Abstracts of papers, 236th ACS National Meeting, Philadelphia, PA, United States, Aug. 17-21, 2008, 1 page.

Metobo et al., "Practical synthesis of 1'-substituted Tubercidin C-nucleoside analogs," Tetrahedron Letters, Feb. 2012, 53(5):484-486.

Migliaccio et al., "Characterization of Resistance to Non-obligate Chain-terminating Ribonucleoside Analogs That Inhibit Hepatitis C Virus Replication in vitro." The Journal of Biological Chemistry, 2003, 278(49): 49164-49170.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans, 1, 1992, pp. 2345-2353.

Mitchell et al., "Synthesis of C-Nucleoside Isosteres of 9-(2-Hydroxyethoxymethyl)guanine (Acyclovir)," J. Het. Chem., 1984, 21(3): 697-699.

Moennig et al., "The Pestiviruses", Advances in Virus Research, 1992, 41: 53-98.

Moradpour et al., "Replication of hepatitis C virus," Nature Reviews Microbiology, 2007, 5(6): 453-463.

Morris, "Mechanisms of action and therapeutic role of corticosteroids in asthma", J. Allergy Clin. Inmunol., Jan. 1985, 75(1 Pt): 1-13.

Moscow et al., "Reduced Folate Carrier Gene (RFC1) Expression and Anti-Folate Resistance in Transfected and Non-Selected Cell Lines," International Journal of Cancer, 1997, 72: 184-190.

Mossel et al., "Exogenous ACE2 expression allows refractory cell lines to support severe acute respiratory syndrome coronavirus replication," Journal of Virology, Mar. 15, 2005, 79(6): 3846-50.

Mulangu et al., "A Randomized, Controlled Trial of Ebola Virus Disease Therapeutics," New England Journal of Medicine, Dec. 2019; 381(24): 2293-303.

Munster et al., "Hydroxychloroquine concentration-response relationships in patients with rheumatoid arthritis", Arthritis Rheumatology, Jun. 2002, 46(6): 1460-1469.

Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.

Murakami et al., "Mechanism of Activation of PSI-7851 and Its Diastereoisomer PSI-7977", The Journal of Biological Chemistry, 2010, 285(45): 34337-34347.

Murphy et al., "The Nucleoside Analog GS-441524 Strongly Inhibits Feline Infectious Peritonisitis (FIP) Virus in Tissue Culture and Experimental Cat Infection Studies", Veterinary Microbiology, 2018. 219: 226-233.

Naqvi et al., "Tocilizumab and Remdesivir in a Pregnant Patient With Coronavirus Disease 2019 (COVID-19)," Obstetrics & Gynecology, Nov. 2020, 136(5): 1025-9.

Neumann et al., "Hepatitis C Viral Dynamics in Vivo and the Antiviral Efficacy of Interferon-α Therapy", Science, 1998, 282: 103-107.

Nishimura et al., "Synthesis of pyrrolo[2,1-f][1,2,4]triazine C-nucleosides, Isosteres of sangivamycin, tubercidin, and toyocamycin," Carbohydrate Research, 2001, 331: 77-82.

Ogura et al., "Reaction of Ethynyl Compounds with Lactones," Journal of Organic Chemistry, 1972, 37(1): 72-75.

Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004. 3944-3953.

Otter et al., "Conformational Properties of Purine-Like C-Nucleosides," Nucleosides & Nucleotides, 1996, 15(1-3): 793-807.

Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5): 121-133.

Pankiewicz et al., "C-Nucleoside Analogues of Nicotinamide Mononucleotide (NMN)," Nucleosides and Nucleotides, 1988, 7(5 &6): 589-593.

(56) References Cited

OTHER PUBLICATIONS

Pankiewicz et al., "Efficient Synthesis of 5-(β-D-RibofuranosyD)nicotinamide and its α-Isomer," Journal of Organic Chemistry, 1988, 53: 3473-3479.

Patani et al., "Bioisosterism: a rational approach in drug design," Chem. Rev., 1996, 96:3147-3176.

Patil et al., "4-Aza-7,9-Dideazaadenosine, a New Cytotoxic Synthetic C-Nucleoside Analogue of Adenosine," Tetrahedron Letters, 1994, 35(30): 5339-5342.

Patil et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 1990, 9(7): 937-956.

Patil et al., "Synthesis of Pyrrolo[2,1-f][1,2,4]triazine Congeners of Nucleic Acid Purines via the N-Amination of 2-Substituted Pyrroles," J. Het. Chem., 1994, 31: 781-786.

Patil et al., "Synthesis of some new thieno[3,4-d]pyrimidines and their C-nucleosides," Journal of Heterocyclic Chemistry, 1993, 30(2): 509-515.

Pelet et al., "High throughput screening assay for negative single stranded RNA virus polymerase inhibitors," J. Virol. Methods, Sep. 2005, 128(1-2): 29-36.

Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.

Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.

Peterson et al., "Prodrug approaches to improving the oral absorption of antiviral nucleotide analogues." Expert Opinion, Drug Deliv., 2009, 6(4): 405-420.

Piccirilli et al., "A Direct Route to 3-(D-Ribofuranosyl)pyridine Nucleosides," Helvetica Chimica Acta, 1991, 74: 397-406.

Pierce-Williams et al., "Clinical course of severe and critical coronavirus disease 2019 in hospitalized pregnancies: a United States cohort study," American Journal of Obstetrics & Gynecology MFM, Aug. 2020, 2(3): 12 pages.

Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.

Pilcer et al., "Formulation strategy and use of excipients in pulmonary drug delivery," International Journal of Pharmaceutics, Jun. 2010, 392(1-2): 1-19.

Pizzorno et al., "In vitro evaluation of antiviral activity of single and combined repurposable drugs against SARS-CoV-2," Antiviral Research, Sep. 2020, 181: 104878.

Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.

Porter et al., "Zika virus, drug discovery, and student projects," ScienceBlogs, Mar. 9, 2016, 7 pages.

Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940): 1-16.

Puech et al., "Intracellular Delivery of Nucleoside Monophosphates through a Reductase-mediated Activation Process," Antiviral Research, 1993, 22(4): 155-174.

Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.

Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.

Rebeaud et al., "SARS-CoV-2 and the Use of Chloroquine as an Antiviral Treatment," Frontiers in Medicine, Apr. 24, 2020, 7: 184, 6 pages.

Reddy et al., "Stereoselective Synthesis of Nucleoside Monophosphate HepDirectTM Prodrugs," Tet. Lett., 2005, 46: 4321-4324.

Remington's Pharmaceutical Science, 17th ed., Gennaro (ed)., 1985, Chapter 68, 58 pages.

Ross et al., "Synthesis of Diastereomerically Pure Nucleotide and Phosphoramidates," J. Org. Chem., 2011, 76: 8311-8319.

Sacramento et al., "The clinically approved antiviral drug Sofosbuvir inhibits Zika Virus replication." Nature, Jan. 18, 2017, 7: 40920, 12 pages.

Sahakijpijarn et al., "Development of Remdesivir as a Dry Powder for Inhalation by Thin Film Freezing." Pharmaceutics, Oct. 2020, 12(11):1002, 27 pages.

Schnettler et al., "Severe acute respiratory distress syndrome in coronavirus disease 2019-infected pregnancy: obstetric and intensive care considerations," American Journal of Obstetrics & Gynecology MFM, Aug. 2020, 2(Suppl 3): 10 pages.

Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>. 3 pages.

Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.

Schultz, "Prodrugs of Biologically Active Phosphate Esters," Bioorganic & Medicinal Chemistry, 2003, 11: 885-898.

Scott et al., "Interferon-a-2b Plus Ribavirin: A Review of its Use in the Management of Chronic Hepatitis C," Drugs, 2002, 62(3): 507-556.

Sheahan et al., "Broad-spectrum antiviral GS-5734 inhibits both epidemic and zoonotic coronaviruses", Science Translational Medicine, Jun. 2017, 9(396):eaal3653. 11 pages.

Sheahan et al., "Comparative therapeutic efficacy of remdesivir and combination lopinavir, ritonavir, and interferon beta against MER-CoV," Nature Communications, 2020, 11(222): 1-14.

Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.

Shekunov et al., "Crystallization processes in pharmaceutical technology and drug delivery design," Journal of Crystal Growth, 2000, 211: 122-136.

Shi et al., "Synthesis and anti-viral activity of a series of d- and 1-2'-deoxy-2'-fluororibonucleosides in the subgenomic HCV replicon system." Bioorganic & Medicinal Chemistry, Mar. 2005, 13(5):1641-1652.

Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.

Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.

Silverman et al., "The Organic Chemistry of Drug Design and Drug Action," Elsevier Science, 1992. pp. 19-23.

Silverman, "The Organic Chemistry of Drug Design and Drug Action," Elsevier Science, 2nd Ed., 2004, pp. 29-34.

Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19): 7202-7218.

(56) References Cited

OTHER PUBLICATIONS

Spinner et al., "Effect of Remdesivir vs Standard Care on Clinical Status at 11 Days in Patients With Moderate COVID-19: A Randomized Clinical Trial," Jama, Sep. 2020, 324(11): 1048-1057.
Srivastav et al., "Antiviral Activity of Various 1-(2'-Deoxy-β-D-lyxofuranosyl), 1-(2'-Fluoro-B-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.
Stein et al., "Phosphorylation of Nucleoside Analog Antiretrovirals: A Review for Clinicians," Pharmacotherapy, Jan. 2001, 21(1): 11-34.
Stella et al., "Cyclodextrins," Toxicologic Pathology, 2008, 36(1): 30-42.
Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.
Sun, "Remdesivir for Treatment of COVID-19: Combination of Pulmonary and IV Administration May Offer Additional Benefit", The AAPS Journal, 2020, 22(77):1-6.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Tapia et al., "Combination of a Mutagenic Agent with a Reverse Transcriptase Inhibitor Results n Systematic Inhibition of HIV-1 Infection," Virology, 2005, 338: 1-8.
Taylor, "Aulton's Pharmaceutics: The Design and Manufacture of Medicines; Chapter 37: Pulmonary Drug Delivery." 5th ed., Aulton et al.(ed), 2018: 653-670.
Totura et al., "Broad-spectrum coronavirus antiviral drug discovery", Expert Opinion on Drug Discovery, Mar. 2019, 17 pages.
Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inhibition of coronavirus RNA-dependent RNA polymerase by remdesivir reveals a second mechanism of action," J. Biol. Chem., 2020, 295(47): 16156-16165.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.
Venkatachalam et al., "Effect of change in nucleoside structure on the activation and antiviral activity of phosphoramidate derivatives," Bioorganic & Medicinal Chemistry, 2005, 13: 5408-5423.
Vieira et al., "Development of a Large-Scale Cyanation Process Using Continuous Flow Chemistry En Route to the Synthesis of Remdesivir," Organic Process Research & Development, May 2020, 24(10):2113-2121.
V'kovski et al., "Coronavirus Biology and Replication: Implications for SARS-CoV-2," Nature Reviews Microbiology, Oct. 2021, 19(3): 155-170.
Walker et al., "Plasma chloroquine and desethylchloroquine concentrations in children during and after chloroquine treatment for malaria.", British Journal Clinical Pharmacology, Dec. 1983, 16(6): 701-705.
Wang et al., "ANNOVAR: functional annotation of genetic variants from high-throughput sequencing data," Nucleic Acids Research, 2010, 38(16): e164, 7 pages.
Wang et al., "Remdesivir and chloroquine effectively inhibit the recently emerged novel coronavirus (2019-nCoV) in vitro", Cell Research, 2020, 30: 269-271.
Wang et al., "Remdesivir in adults with severe COVID-19: a randomised, double-blind, placebo-controlled, multicentre trial," Lancet, Apr. 29, 2020, 395: 1569-1578.
Warren et al., "Protection against filovirus diseases by a novel broad-spectrum nucleoside analogue BCX4430", Nature, Apr. 2014, 508(7496): 402-405.
Warren et al., "Therapeutic efficacy of the small molecules GS-5734 against EBOLA virus in rhesus monkeys", Nature, Mar. 17, 2016, 531(7594): 381-385.
Wolfel et al., "Virological assessment of hospitalized patients with COVID-2019," Nature, Apr. 2020, 581: 465-470.
Wu et al., "Synthetic Methodologies for C-Nucleosides," Synthesis, 2004, 10: 1533-1553.
Xie et al., "A nanoluciferase SARS-CoV-2 for rapid neutralization testing and screening of anti-infective drugs for COVID-19," Nature Communications, Oct. 15, 2020, 11(1):1-11.
Xie et al., "Engineering SARS-CoV-2 using a reverse genetic system," Nature protocols, Jan. 29, 2021, 16(3): 1761-1784.
Xie et al., "Weinreb Amide Approach to the Practical Synthesis of a Key Remdesivir Intermediate," The Journal of Organic Chemistry, 2021, 86:5065-5072.
Yamanaka et al., "Metabolic Studies on BMS-200475, a New Antiviral Compound Active against Hepatitis B Virus," Antimicrobial Agents and Chemotherapy, 1999, p. 43(1): 190.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Yates et al., "The evolution of antiviral nucleoside analogues: A review for chemists and non-chemists. PartII: Complex modifications to the nucleoside scaffold", Antiviral Research, Dec. 8, 2018, 162: 5-21.
Yoon et al., "High-throughput screening-based identification of paramyxovirus inhibitors," J. Biomol. Screen., Aug. 2008, 13(7): 591-608.
Yoshimura et al., "Synthesis and Biological Evaluation of 1'-C-Cyano-Pyrimidine Nucleosides," Nucleosides & Nucleotides, 1996, 15(1-3): 305-324.
Zhang et al., "A Practical Synthesis of (2R)-3,5-di-O-benzoyl-2-fluoro-2-C-methyl-D-ribono-y-lactone", Tetrahedron: Asymmetry, 2009, 20: 305-312.
Zhu et al., "A novel coronavirus from patients with pneumonia in China, 2019," New England Journal of Medicine, Jan. 24, 2020, 14 pages.
ARIPO Patent Office, Form 21 and Substantive Examination Report (in English) for AP Application No. AP/P/2010/005439, dated Mar. 18, 2014.
ARIPO Patent Office, Forn 21 for AP Patent Application No. AP/P/2011/005818, dated Sep. 19, 2013.
ARIPO Patent Office, Search and Exam Report for AP Application No. AP/P/2012/006189, dated Jun. 26, 2014.
Australia Patent Office, First Examination Report for AU Patent Application No. 2009240630, dated Jun. 14, 2012.
Australia Patent Office, Patent Examination Report No. 1 for AU Application No. 2011306066, dated Nov. 21, 2013.
Australia Patent Office, Patent Examination Report No. 1 for AU Patent Application No. 2010213873, dated Jun. 4, 2014.
Australian Office Action in AU Appln. No. 2021234308, dated Apr. 26, 2023, 4 pages.
Chile Patent Office, First Office Action for CL Patent Application No. 1906-2011.
Chile Patent Office, Opposition for CL Patent Application No. 727-2013, dated Oct. 15, 2013.
Chile Patent Office, Second Office Action for CL Patent Application No. 1906-2011, dated Oct. 16, 2013.
Chinese Patent Office, First Examination Report for CN Patent Application No. 200980120218.8, dated Nov. 13, 2012.
Chinese Patent Office, First Office Action for CN Patent Application No. 201080011690.0, dated Jun. 8, 2013.
Chinese Patent Office, Notification of Reexamination for CN Patent Application No. 200980120218.8, dated Sep. 1, 2014.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.

(56) References Cited

OTHER PUBLICATIONS

Columbia Patent Office, First Examination Report (in English) for CO Patent Application No. 10-131479, dated Oct. 23, 2012.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-131479, dated Sep. 27, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Ecuador Patent Office, Opposition for EC Patent Application No. SP-2012-11817, dated May 27, 2013.
El Salvador Patent Office, Official Action for SV National Phase Entry of International Application No. PCT/US2010/049471, dated Nov. 6, 2013.
Eurasian Patent Office, First Examination Report for EA Patent Application No. 201071128, dated Apr. 25, 2012.
Eurasian Patent Office, First Office Action for EA Patent Application No. 201190110/28, dated Apr. 26, 2012.
Eurasian Patent Office, First Office Action for EA Patent Application No. 201390141/28, with English translation.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Office Action for EA Application No. 201190110/28, dated Oct. 18, 2013.
European Patent Office, Communication pursuant to Article 94(3) EPC for EP Patent Application No. 10763083.2, dated May 2, 2014.
European Patent Office, Communication pursuant to Article 94(3) EPC for EP Patent Application No. 11715792.5, dated Feb. 14, 2014.
European Patent Office, Communication under 161/162 for EP Patent Application No. 10704068.5, dated Sep. 6, 2011.
European Patent Office, Communication under 161/162 for EP Patent Application No. 10763083.2, dated May 11, 2012.
European Patent Office, Communication under 161/162 for EP Patent Application No. 11715792.5, dated Apr. 26, 2013.
European Patent Office, First Office Action for EP Patent Application No. 10704068.5, dated Jun. 18, 2012.
Indonesia Patent Office, First Examination Report for ID Patent Application No. W00 2010 03957, dated Apr. 25, 2013.
Indonesia Patent Office, Substantive Examination Report Stage 1 for ID Application No. W-00201103126, dated Jun. 10, 2014.
Israel Patent Office, First Examination Report for IL Patent Application No. 208701, dated Jan. 13, 2013.
Israel Patent Office, First Office Action for IL Patent Application No. 214396, dated Jul. 8, 2013.
Israel Patent Office, Notification of Defects for IL Patent Application No. 214396, dated Nov. 11, 2013.
Israel Patent Office, Notification of Defects for IL Patent Application No. 218599, dated Aug. 25, 2014.
Israel Patent Office, Notification of Defects for IL Patent Applicaton No. 208701, dated Aug. 25, 2014.
Israel Patent Office, Notification Prior to Examination for IL Patent Application No. 218599, dated Nov. 13, 2012.
Japanese Patent Office, First Examination Report for JP Patent Application No. 2011-506429, dated Aug. 22, 2013.
Japanese Patent Office, Notice of Reasons for Rejection for Japanese Patent Appln. No. JP 2017-520934, dated Mar. 30, 2018.
Japanese Patent Office, Notification of Reasons for Rejection for JP Application No. 2011-549324, dated Jul. 28, 2014.
Japanese Patent Office, Notification of Reasons for Rejection for JP Application No. 2011-549324, dated Mar. 26, 2014.
Japanese Patent Office, Notification of Reasons for Rejection for JP Patent Application No. 2012-529958, dated Aug. 5, 2014.
Mexico Patent Office, English translation of Office Action for MX Application No. MX/a/2013/003179, dated Feb. 25, 2014.
Mexico Patent Office, First Examination Report (in English) for MX Patent Application No. MX/a/2010/011661, dated Oct. 26, 2011.
Mexico Patent Office, Office Action for MX Application No. MX/a/2011/008409, dated Mar. 25, 2014.
New Zealand Patent Office, First Examination Report for NZ Patent Application No. 588670, dated Apr. 8, 2011.
New Zealand Patent Office, First Examination Report for NZ Patent Application No. 608070, dated Nov. 7, 2013.
New Zealand Patent Office, Further Examination Report for NZ Application No. 594370, dated Oct. 8, 2013.
PCT International Preliminary Report on Patentability and Written Opinion for PCT International Application No. PCT/US2009/041432, dated Oct. 26, 2010, 7 pages.
PCT International Preliminary Report on Patentability and Written Opinion for PCT International Application No. PCT/US2010/049471, dated Mar. 27, 2012, 7 pages.
PCT International Preliminary Report on Patentability and Written Opinion for PCT International Application No. PCT/US2011/038253, dated Dec. 4, 2012, 6 pages.
PCT International Preliminary Report on Patentability for PCT International Application No. PCT/US2010/023586, dated Aug. 16, 2011, 6 pages.
PCT International Preliminary Report on Patentability for PCT International Application No. PCT/US2011/028897, dated Mar. 26, 2013, 7 pages.
PCT International Preliminary Report on Patentability for PCT International Application No. PCT/US2011/029441, dated Mar. 26, 2013. 7 pages.
PCT International Preliminary Report on Patentability for PCT International Application No. PCT/US2015/057934, dated May 11, 2017, 14 pages.
PCT International Search Report and Written Opinion for PCT International Application No. PCT/US2009/041432, dated Aug. 11, 2009, 11 pages.
PCT International Search Report and Written Opinion for PCT International Application No. PCT/US2010/023586, dated Aug. 4, 2010, 4 pages.
PCT International Search Report and Written Opinion for PCT International Application No. PCT/US2010/049471, dated Nov. 18, 2010, 11 pages.
PCT International Search Report and Written Opinion for PCT International Application No. PCT/US2011/028897, dated Aug. 1, 2011, 6 pages.
PCT International Search Report and Written Opinion for PCT International Application No. PCT/US2011/029441, dated Aug. 1, 2011, 5 pages.
PCT International Search Report and Written Opinion for PCT International Application No. PCT/US2011/038253, dated Jul. 29, 2011, 4 pages.
PCT International Search Report and Written Opinion for PCT International Application No. PCT/US2017/028251, dated Oct. 16, 2017, 22 pages.
PCT International Search Report and Written Opinion for PCT International Application No. PCT/US2017/028251, dated Sep. 13, 2017, 22 pages.
PCT International Search Report and Written Opinion in International Application No. PCT/US2021/021880, dated Sep. 21, 2021, 20 pages.
Resolution No. 48031 for CO Patent Application No. 10-121.513, rec'd Oct. 7, 2014 (8 pages) (English translation).
Taiwanese Office Action in TW Appln. No. 110108759, dated Dec. 22, 2021, 36 pages (with English translation).
Ukraine Patent Office, First Examination Report for UA Patent Application No. 2010 13030, dated Mar. 2, 2013.

(56) References Cited

OTHER PUBLICATIONS

Ukraine Patent Office, First Office Action for UA Application No. a 2011 10568.
Ukraine Patent Office, Second Office Action for UA Patent Application No. 2011 10568, dated Aug. 11, 2014.
Vietnam Patent Office, First Examination Report for VN Patent Application No. 1- 2010-02939, dated Apr. 19, 2012.
Vietnam Patent Office, Second Examination Report for VN Patent Application No. 1-2010-02939, dated Jul. 26, 2012.
"Medical Microbiology," Fourth Edition, Baron (ed.), University of Texas Medical Branch at Galveston, 1996, Chapters 59 and 72, 38 pages.
"Molecular Nuclear Medicine," Second Edition, Wang (ed.), Union Medical College of China, 2004, pp. 417-419 (with English translation).
[No Author Listed], "Definitive Rules for Nomenclature of Organic Chemistry," Journal of the American Chemistry Society, Nov. 1, 1960, 82(21):5545-5574.
Assiri et al., "Epidemiological, Demographic, and Clinical Characteristics of 47 Cases of Middle East Respiratory Syndrome Coronavirus Disease From Saudi Arabia: A Descriptive Study," The Lancet Infectious Diseases, Sep. 2013, 13(9):752-61.
Austin, "An Introduction to Propensity Score Methods for Reducing the Effects of Confounding in Observational Studies," Multivariate behavioral research, May 2011, 46(3): 399-424.
Barnes, "Corticosteroids: The drugs to beat," European Journal of Pharmacology, Mar. 8, 2006, 533(1-3):2-14.
Beaucourt et al., "Ribavirin: a drug active against many viruses with multiple effects on virus replication and propagation. Molecular basis of ribavirin resistance," Current Opinions in Virology, May 2014, 8:10-15.
Bhimraj et al., "Infectious Diseases Society of America guidelines on the treatment and management of patients with COVID-19," Clinical Infectious Diseases, Apr. 27, 2020, 20 pages.
Bonilauri et al., "Animal Coronaviruses and SARS-COV-2 in Animals, What Do We Actually Know?," Life, Feb. 2021, 11(2): 1-17.
Bornholdt et al., "A Two-Antibody Pan-Ebolavirus Cocktail Confers Broad Therapeutic Protection in Ferrets and Nonhuman Primates," Cell Host Microbe, Jan. 2019, 25(1): 49-58, e1-e5.
Brannan et al., "Post-exposure immunotherapy for two ebolaviruses and Marburg virus in nonhuman primates," Nature Communications, Jan. 2019, 10: 105, 10 pages.
Center for Disease Control and Prevention (CDC) [online], "Animals & COVID-19," COVID-19, last updated Apr. 7, 2023, retrieved on Aug. 29, 2023, retrieved from URL: <https://www.cdc.gov/coronavirus/2019-ncov/daily-life-coping/animals.html>, 4 pages.
Center for Disease Control and Prevention (CDC) [online], "Classifications & Definitions," COVID-19, last updated Mar. 20, 2023, retrieved on Aug. 29, 2023, retrieved from URL: <https://www.cdc.gov/coronavirus/2019-ncov/variants/variant-classifications.html>, 6 pages.
Center for Disease Control and Prevention (CDC) [online], "COVID Data Tracker," last updated Aug. 24, 2023, retrieved on Aug. 25, 2023, retrieved from URL <https://covid.cdc.gov/covid-data-tracker/#datatracker-home>, 5 pages.
Center for Disease Control and Prevention (CDC) [online], "SARS-CoV-2 variant classifications and definitions," last updated Mar. 20, 2023, retrieved on Aug. 25, 2023, retrieved from URL <https://www.cdc.gov/coronavirus/2019-ncov/variants/variant-classifications.html>, 6 pages.
Charytan et al., "Decreasing Incidence of Acute Kidney Injury in Patients with COVID-19 Critical Illness in New York City," Kidney International Reports, Apr. 2021, 6(4):916-27.
Chinese Office Action in CN Appln. No. 202180019951.1, dated Dec. 28, 2023, 25 pages (with English translation).
Choe et al., "Exploration for the effect of renal function and renal replacement therapy on pharmacokinetics of remdesivir and GS-441524 in patients with COVID-19: A limited case series," Clinical and Translational Science, Nov. 20, 2021, 15(3):732-740.
Choi et al., "Clinical Presentation and Outcomes of Middle East Respiratory Syndrome in the Republic of Korea," Infection & Chemotherapy, Jun. 2016, 48(2): 118-26.
ClinicalTrials.gov [online], "Study of Obeldesivir in Nonhospitalized Participants With COVID-19 (Oaktree)," NCT05715528, last updated Oct. 19, 2023, retrieved on Oct. 19, 2023, retrieved from URL<https://clinicaltrials.gov/study/NCT05715528?term=NCT05715528&rank=1>, 13 pages.
ClinicalTrials.gov [online], "Study of Obeldesivir in Participants With COVID-19 Who Have a High Risk of Developing Serious or Severe Illness (Birch)," Gilead Sciences, Trial Identifier: NCT05603143, last updated Aug. 3, 2023, retrieved on Aug. 23, 2023, retrieved from URL: <https://classic.clinicaltrials.gov/ct2/show/record/NCT05603143>, 8 pages.
Coffin et al., "Persistent Marburg Virus Infection in the Testes of Nonhuman Primate Survivors," Cell Host & Microbe, Sep. 2018, 24(1): 405-416.
Complexity Science Hub Vienna [online], "SARS-ANI VIS: A Global Open Access Dataset of Reported SARS-CoV-2 Events in Animals," last updated Jul. 12, 2023, retrieved on Aug. 29, 2023, retrieved from URL: <https://vis.csh.ac.at/sars-ani/#variants>, 2 pages.
Cross et al., Combination therapy protects macaques against advanced Marburg virus disease. Nature Communications, Mar. 2021, 12(1): 1891, 10 pages.
Davis et al., "Dose Optimization of Obeldesivir for COVID-19 Treatment in Patients With Renal Impairment Using Population Pharmacokinetic Modeling," Presented at the Fourteenth American Conference on Pharmacometrics (ACoP14), Nov. 5-8, 2023, National Harbor, MD, USA, 1 page.
De Wit et al., "SARS and MERS: Recent Insights Into Emerging Coronaviruses," Nature Review, Jun. 2016; 14: 523-34.
Eastman et al., "Remdesivir: A Review of Its Discovery and Development Leading to Emergency Use Authorization for Treatment of COVID-19," ACS Central Science, May 4, 2020; 6(5): 672-83.
ERA-EDTA Council et al., "Chronic kidney disease is a key risk factor for severe COVID-19: a call to action by the ERA-EDTA," Nephrology Dialysis Transplantation, Jan. 2021, 36(1): 87-94.
European Centre for Disease Prevention and Control (ECDC) [online], "SARS-CoV-2 variants of concern as of Aug. 24, 2023," last updated Aug. 24, 2023, retrieved on Aug. 29, 2023, retrieved from URL: <https://www.ecdc.europa.eu/en/covid-19/variants-concern>, 18 pages.
European Medicines Agency, "New vaccine for prevention of Ebola virus disease recommended for approval in the European Union," Press Release, May 29, 2020, 3 pages.
European Medicines Agency, "Summary on compassionate use: Remdesivir Gilead," Procedure No. EMEA/H/K/005622/CU, Apr. 3, 2020, 45 pages.
Feldmann et al., "Chapter 32: Filoviridae: Marburg and Ebola Viruses," in Fields Virology, Sixth Edition, May 2013, 1: 36 pages.
Feldmann et al., "Ebola," New England Journal of Medicine, May 2020, 382: 1832-42.
Flythe et al., "Characteristics and Outcomes of Individuals With Pre-existing Kidney Disease and COVID-19 Admitted to Intensive Care Units in the United States," American Journal of Kidney Diseases, Feb. 2021, 77(2): 190-203.
Food and Drug Administration (FDA), "Estimating the Maximum Safe Starting Dose in Initial Clinical Trials for Therapeutics in Adult Healthy Volunteers," Jul. 2005, 30 pages.
Food and Drug Administration (FDA), "Fact Sheet for Healthcare Providers: Emergency Use Authorization for Lagevriotm™(molnupiravir) Capsules," FDA Emergency Use Authorization, published Dec. 2021, 21 pages.
Food and Drug Administration (FDA), "Highlights of Prescribing Information for PAXLOVID™," revised May 2023, 51 pages.
Fuse, "Organic Synthesis Using Microflow Reactor," Journal of Synthetic Organic Chemistry Japan, 2012, 70(2): 177-178 (with English abstract).
Garnett et al., "Scientific white paper on concentration-QTc modeling," J. Pharmacokinet Pharmacodyn., Jun. 2018, 45(3):383-397.

(56) References Cited

OTHER PUBLICATIONS

Geisbert et al., "Considerations in the Use of Nonhuman Primate Models of Ebola Virus and Marburg Virus Infection," The Journal of Infectious Diseases, Oct. 2015, 212(Suppl. 2), S91-97.
Geisbert et al., "Single-injection vaccine protects nonhuman primates against infection with Marburg virus and three species of Ebola virus," Journal of Virology, Jul. 2009, 83(14): 7296-7304.
Gilead Sciences, Inc., "Veklury 100 mg powder for concentrate for solution for infusion," Package Leaflet, last revised Jun. 2023, 12 pages.
Gilead Sciences, Inc., "VEKLURY® (remdesivir) Full Prescribing Information" last revised Jul. 2023, 44 pages.
Goldman et al., "Remdesivir for 5 or 10 Days in Patients with Severe Covid-19," New England Journal of Medicine, May 2020, 383(19), 1827-37.
Gupta et al., "Factors Associated With Death in Critically Ill Patients With Coronavirus Disease 2019 in the US," JAMA Internal Medicine, Nov. 2020, 180(11): 1436-47.
Han et al., "Genetic, antigenic and pathogenic characterization of avian coronaviruses isolated from pheasants (*Phasianus colchicus*) in China," Veterinary Microbiology, Nov. 2019, 240: 1-14.
Harbeson et al., "Deuterium in Drug Discovery and Development," Annual Reports in Medicinal Chemistry, Dec. 31, 2011, 46:403-417.
Harvey et al., "Association of SARS-CoV-2 Seropositive Antibody Test With Risk of Future Infection," JAMA Internal Medicine, Feb. 24, 2021; 181(5): 672-679.
Henry et al., "Chronic kidney disease is associated with severe coronavirus disease 2019 (COVID-19) infection," International urology and nephrology, Jun. 2020, 52(6): 1193-4.
Herbert et al., "Development of an antibody cocktail for treatment of Sudan virus infection," Proceedings of the National Academy of Sciences, Feb. 2020, 117: 3768-78.
Hop et al., "Plasma-pooling methods to increase throughput for in vivo pharmacokinetic screening," Journal of Pharmaceutical Sciences, Jul. 1998, 87(7):901-903.
Hoste et al., "Assessment of renal function in recently admitted critically ill patients with normal serum creatinine," Nephrology Dialysis Transplantation, Apr. 2005, 20(4): 747-53.
Hsu et al., COVID-19 Among US Dialysis Patients: Risk Factors and Outcomes From a National Dialysis Provider, American Journal of Kidney Disease, May 2021, 77(5):748-56.
Japanese Office Action in JP Appln. No. 2022-553075, dated Sep. 27, 2023, 8 pages (with English translation).
Julander et al., "Remdesivir efficacy against yellow fever in a hamster model," Antiviral Research, Jul. 2022, 203:105331.
Khbou et al., "Coronaviruses in farm animals: Epidemiology and public health implications," Veterinary Medicine and Science, Sep. 2020, 7(2): 322-347.
Kim et al., "Detection of bovine coronavirus in nasal swab of non-captive wild water deer, Korea," Transboundary and Emerging Diseases, Mar. 2018, 65(3): 627-631.
Ksiazek et al., "A Novel Coronavirus Associated with Severe Acute Respiratory Syndrome," New England Journal of Medicine, May 2003, 348(20): 1953-66.
Languon et al., "Filovirus Disease Outbreaks: A Chronological Overview," Virology: Research and Treatment, Jun. 2019, 10: 1-12.
Levey et al., "Using standardized serum creatinine values in the modification of diet in renal disease study equation for estimating glomerular filtration rate," Annals of Internal Medicine, Aug. 15, 2006, 145(4):247-254.
Li et al., "Remdesivir Metabolite GS-441524 Effectively Inhibits SARS-CoV-2 Infection in Mouse Models," Journal of Medicinal Chemistry, Feb. 2021, 65(4): 2785-2793.
Lo et al., "Remdesivir (GS-5734) protects African green monkeys from Nipah virus challenge," Science Translational Medicine, May 29, 2019, 11(494):1-6.
Malin et al., "Remdesivir against COVID-19 and Other Viral Diseases," Clinical Microbiology Reviews, Oct. 14, 2020, 34(1):e00162-20.

Markham, "REGN-EB3: First Approval," Drugs, Jan. 2021, 81: 175-178.
McGuigan et al., "Application of Phosphoramidate Pronucleotide Technology to Abacavir Leads to a Significant Enhancement of Antiviral Potency", J. Med. Chem. 2005, 48(10):3504-3515.
National Institute of Diabetes and Digestive and Kidney Diseases (NIDDK), "2009 CKD-EPI Creatinine Calculator," Chronic Kidney Disease Epidemiology Collaboration (CKD-EPI) equation, last reviewed Dec. 2022, retrieved from URL <https://www.niddk.nih.gov/health-information/professionals/clinical-tools-patient-management/kidney-disease/laboratory-evaluation/glomerular-filtration-rate-calculators/historical>, 2 pages.
Nguyen et al., "Favipiravir pharmacokinetics in Ebola-Infected patients of the JIKI trial reveals concentrations lower than targeted," PLoS Neglected Tropical Diseases, Feb. 2017, 11(2), 18 pages.
Office Action in CA Appln. No. 3169340, dated Oct. 20, 2023, 4 pages.
Ozturk et al., "Mortality analysis of COVID-19 infection in chronic kidney disease, haemodialysis and renal transplant patients compared with patients without kidney disease: a nationwide analysis from Turkey," Nephrology Dialysis Transplantation, Dec. 2020, 35(12): 2083-95.
Patel et al., "Analysis of MarketScan Data for Immunosuppressive Conditions and Hospitalizations for Acute Respiratory Illness, United States," Emerging Infectious Diseases, Apr. 29, 2020; 26(8): 1720-30.
Peart Akindele et al., "Effect of remdesivir post-exposure prophylaxis and treatment on pathogenesis of measles in rhesus macaques," Scientific Reports, Apr. 20, 2023, 13:6463.
Pitts et al., "Efficacy in Multiple SARS-CoV-2 Animal Models Supports Phase 3 Dose Selection for Obeldesivir," presented at IDWeek, Boston, MA, USA, Oct. 11-15, 2023, Abstract 539.
Porter et al., "Remdesivir (GS-5734) Is Efficacious in Cynomolgus Macaques Infected With Marburg Virus," The Journal of Infectious Diseases, Jun. 2020, 222(11): 1894-1901.
Prasad et al., "Resistance of Cynomolgus Monkeys to Nipah and Hendra Virus Disease Is Associated With Cell-Mediated and Humoral Immunity," The Journal of Infectious Diseases, May 2020, 221(Suppl. 4): S436-447.
Radoshitzky et al., "Expanded profiling of Remdesivir as a broad-spectrum antiviral and low potential for interaction with other medications in vitro," Scientific Reports, Feb. 23, 2023, 13:3131.
Rahim et al., "Postexposure Protective Efficacy of T-705 (Favipiravir) Against Sudan Virus Infection in Guinea Pigs," The Journal of Infectious Diseases, Jul. 2018, 218(Suppl. 5): S649-S657.
Rasmussen et al., "Nucleoside analog GS-441524: pharmacokinetics in different species, safety, and potential effectiveness against Covid-19," Pharmacol. Res. Perspect., Apr. 2022, 10(2):e00945.
Ronco et al., "Kidney Involvement in COVID-19 and Rationale for Extracorporeal Therapies," Nature Reviews Nephrology, Apr. 2020, 16: 308-310.
Schindell et al., "Persistence and Sexual Transmission of Filoviruses," Viruses, Dec. 2018, 10(12), 22 pages.
Sendi et al., "First-generation oral antivirals against SARS-CoV-2," Clin. Microbiol. Infect., Sep. 2022, 28(9):1230-1235.
Shetty et al., "COVID-19-Associated Glomerular Disease," Journal of the American Society of Nephrology, Jan. 2021, 32(1): 33-40.
The Recovery Collaborative Group, "Dexamethasone in Hospitalized Patients with Covid-19," New England Journal of Medicine, Feb. 2020, 384(8): 693-704.
Thi et al., "Rescue of non-human primates from advanced Sudan ebolavirus infection with lipid encapsulated siRNA," Nature Microbiology, Aug. 2016, 1: 16142, 21 pages.
U.S. Department of Agriculture (USDA) [online], "Confirmed Cases of SARS-CoV-2 in Animals in the United States," last updated Aug. 29, 2023, retrieved on Aug. 29, 2023, retrieved from URL: <https://www.aphis.usda.gov/aphis/dashboards/tableau/sars-dashboard>, 1 page.
U.S. Department of Health and Human Services (HHS) [online], "Most common forms based on Pango lineage designations," last updated Aug. 25, 2023, retrieved on Aug. 29, 2023, retrieved from URL: <https://cov.lanl.gov/components/sequence/COV/pangocommonforms.comp>, 264 pages.

(56) References Cited

OTHER PUBLICATIONS

U.S. Food and Drug Administration (FDA), "First FDA-approved vaccine for the prevention of Ebola virus disease, marking a critical milestone in public health preparedness and response," Press Release, Dec. 19, 2019, 3 pages.
U.S. Food and Drug Administration (FDA), "Regulatory Classification of Pharmaceutical Co-Crystals Guidance for Industry," U.S. Department of Health and Human Services, Center for Drug Evaluation and Research (CDER), Feb. 2018, 7 pages.
Vandesompele et al., "Accurate normalization of real-time quantitative RT-PCR data by geometric averaging of multiple internal control genes," Genome Biology, Jun. 2002, 3(7): 1-12.
Warfield et al., "Homologous and heterologous protection of non-human primates by Ebola and Sudan virus-like particles," PLoS ONE, Mar. 2015, 10(3): 16 pages.
Wec et al., "Development of a Human Antibody Cocktail that Deploys Multiple Functions to Confer Pan-Ebolavirus Protection," Cell Host Microbe, Jan. 2019, 25(1): 39-48, e1-e5.
Williamson et al., "Factors associated with COVID-19-related death using OpenSAFELY," Nature, Aug. 2020, 584(7821): 430-6.
World Health Organization (WHO) [online], "Tracking SARS-CoV-2 variants," last updated Aug. 17, 2023, retrieved on Aug. 25, 2023, retrieved from URL <https://www.who.int/en/activities/tracking-SARS-CoV-2-variants>, 11 pages.
World Health Organization (WHO), "Ebola haemorrhagic fever in Zaire, 1976: Report of an International Commission," Bulletin of the World Health Organization, 1978, 56(2): 271-293.
World Health Organization (Who), "WHO Coronavirus (COVID-19) Dashboard," 2020, retrieved on Oct. 19, 2023, retrieved from URL <https://covid19.who.int/>, 1 page.
Wu et al., "AKI and Collapsing Glomerulopathy Associated with COVID-19 and APOL1 High-Risk Genotype," Journal of the American Society of Nephrology, Aug. 2020, 31(8):1688-95.
Zeng et al., "Identification and pathological characterization of persistent asymptomatic Ebola virus infection in rhesus monkeys," Nature Microbiology, Jul. 2017, 2(1), 11 pages.
Zhang et al., "A bacterial artificial chromosome (BAC)-vectored noninfectious replicon of SARS-CoV-2", Antiviral Research, Jan. 2021, 185(1), 9 pages.
U.S. Appl. No. 13/189,373, filed Jul. 22, 2011, Richard L. Makman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.
U.S. Appl. No. 18/128,850, filed Mar. 30, 2023, Tomas Cihlar.
U.S. Appl. No. 18/540,002, filed Dec. 14, 2023, Tomas Cihlar.
U.S. Appl. No. 17/222,125, filed Apr. 5, 2021, Scott Ellis.
U.S. Appl. No. 18/202,751, filed May 26, 2023, Scott Ellis.
U.S. Appl. No. 17/158,391, filed Jan. 26, 2021, Tomas Cihlar.
U.S. Appl. No. 18/131,106, filed Apr. 5, 2023, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 18/241,303, filed Sep. 1, 2023, Nate Larson.
U.S. Appl. No. 15/919,750, filed Mar. 12, 2018, Michael Joseph Perron.
U.S. Appl. No. 16/852,102, filed Apr. 17, 2020, Michael Joseph Perron.
U.S. Appl. No. 17/578,682, filed Jan. 19, 2022, Michael Joseph Perron.
U.S. Appl. No. 17/895,123, filed Aug. 25, 2022, Michael Joseph Perron.
U.S. Appl. No. 18/133,612, filed Apr. 12, 2023, Michael Joseph Perron.
U.S. Appl. No. 18/519,194, filed Nov. 27, 2023, Michael Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 15/267,433, filed Sep. 16, 2016, Michael O'Neil, Hanrahan Clarke.
U.S. Appl. No. 16/265,016, filed Feb. 1, 2019, Michael O'Neil, Hanrahan Clarke.
U.S. Appl. No. 16/863,533, filed Apr. 30, 2020, Michael O'Neil, Hanrahan Clarke.
U.S. Appl. No. 17/222,066, filed Apr. 5, 2021, Michael O'Neil, Hanrahan Clarke.
U.S. Appl. No. 17/748,400, filed May 19, 2022, Michael O'Neil, Hanrahan Clarke.
U.S. Appl. No. 18/402,949, filed Jan. 3, 2024, Michael O'Neil, Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 18/134,792, filed Apr. 14, 2023, Byoung Kwon Chun.
U.S. Appl. No. 18/523,984, filed Nov. 20, 2023, Byoung Kwon Chun.
U.S. Appl. No. 13/813,886, filed Jun. 25, 2013, Aesop Cho.
U.S. Appl. No. 14/746,430, filed Jun. 22, 2015, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2020, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 18/286,971, filed Oct. 13, 2023, Stacy Bremner.
U.S. Appl. No. 17/458,023, filed Aug. 26, 2021, Elaine Bunyan.
U.S. Appl. No. 18/098,950, filed Jan. 19, 2023, Elaine Bunyan.
U.S. Appl. No. 18/410,236, filed Jan. 11, 2023, Elaine Bunyan.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 18/237,152, filed Aug. 25, 2023, Mark J. Bartlett.
U.S. Appl. No. 17/355,813, filed Jun. 23, 2021, Daniel H. Byun.
U.S. Appl. No. 18/544,561, filed Dec. 19, 2023, Daniel H. Byun.
U.S. Appl. No. 18/205,745, filed Jun. 5. 2023, Roy Maxim Bannister.
U.S. Appl. No. 18/243,812, filed Sep. 8, 2023, Casey B. Davis.
U.S. Appl. No. 18/394,488, filed Dec. 22, 2023, Casey B. Davis.
U.S. Appl. No. 18/512,088, filed Nov. 17, 2023, John Philip Bilello.
U.S. Appl. No. 18/215,881, filed Jun. 29, 2023, Kassibla E. Dempah.
U.S. Appl. No. 18/384,060, filed Oct. 26, 2023, Kimberly T. Barrett.
U.S. Appl. No. 18/215,217, filed Jun. 28, 2023, Kassibla E. Dempah.

METHODS OF PREPARING 1'-CYANO NUCLEOSIDES

CROSS-REFERENCES TO RELATED APPLICATIONS

This application is a divisional of U.S. Ser. No. 17/198,829, filed Mar. 11, 2021, which claims priority to the U.S. Provisional Patent Application No. 62/988,661, filed Mar. 12, 2020, and each application is hereby incorporated by reference in its entirety.

BACKGROUND

The compound (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile is an important synthetic intermediate (see e.g. WO2016/069825). There continues to be a need for methods of preparing this intermediate, and other 1'-cyano nucleosides. Additionally there continues to be a need for methods of preparing these compounds at large scale, with good yield, and/or with good purity. The present invention meets this and other needs.

BRIEF SUMMARY

In one embodiment, the present invention provides a method of preparing a compound of Formula (I):

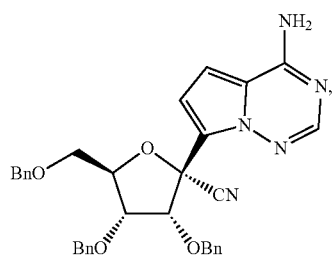

the method comprising: (a) adding a first input mixture to a first flow reactor, wherein the first input mixture comprises a Lewis acid, a Bronsted acid, and a compound of Formula (II-a):

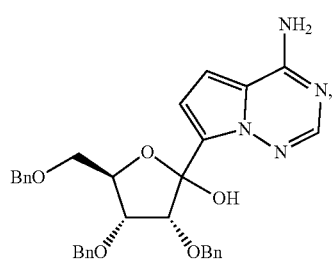

wherein the first flow reactor provides a first output mixture; and (b) adding a second input mixture to a second flow reactor, wherein the second input mixture comprises the first output mixture and a cyanating agent; wherein the second flow reactor provides a second output mixture comprising the compound of Formula (I).

In another embodiment, provided herein is a method of preparing a compound of Formula (II-a):

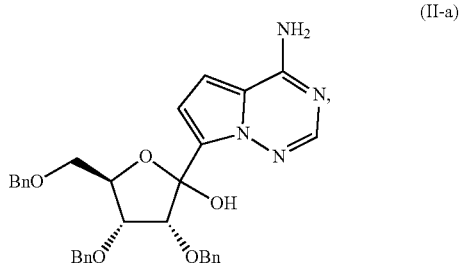 [SMILES: Nc1ncnn2c(C3(O)O[C@H](COCc4ccccc4)[C@@H](OCc4ccccc4)[C@H]3OCc3ccccc3)ccc12]

comprising adding a fifth input mixture to a fifth reactor, wherein the fifth input mixture comprises a compound of Formula (V):

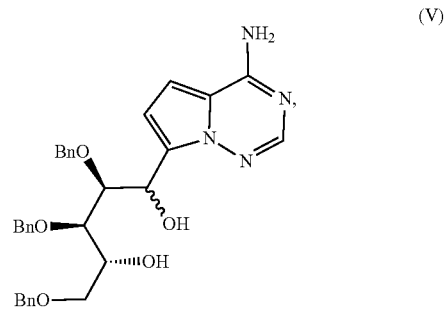 [SMILES: Nc1ncnn2c(C(O)[C@H](OCc3ccccc3)[C@H](OCc3ccccc3)[C@H](O)COCc3ccccc3)ccc12]

an oxidant, and a fifth base, wherein the fifth reactor provides a fifth output mixture comprising the compound of Formula (II-a).

In another embodiment, provided herein is a method of preparing a compound of Formula (VII):

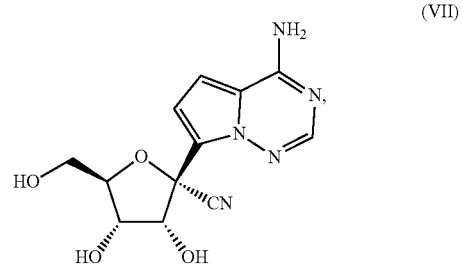 [SMILES: N#C[C@@]1(c2ccc3c(N)ncnn23)O[C@H](CO)[C@@H](O)[C@H]1O]

or a salt thereof, the method comprising adding an eighth input mixture to an eighth flow reactor, wherein the eighth input mixture comprises an eighth Lewis acid and a compound of Formula (I):

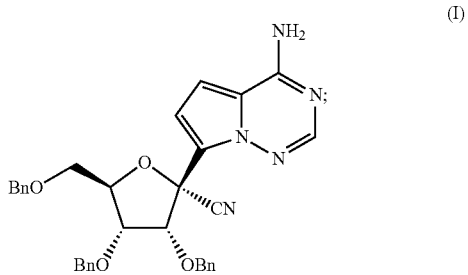 [SMILES: N#C[C@@]1(c2ccc3c(N)ncnn23)O[C@H](COCc2ccccc2)[C@@H](OCc2ccccc2)[C@H]1OCc1ccccc1]

and the eighth flow reactor provides an eighth output mixture comprising the compound of Formula (VII) or salt thereof.

In another embodiment, provided herein is a method of preparing a compound of Formula (VII):

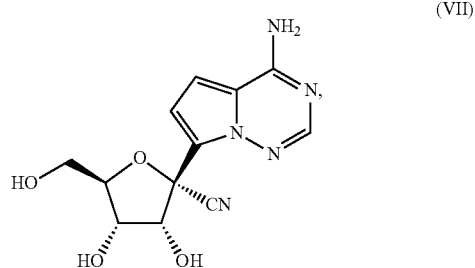 [SMILES: N#C[C@@]1(c2ccc3c(N)ncnn23)O[C@H](CO)[C@@H](O)[C@H]1O]

or a salt thereof, the method comprising combining a compound of Formula (I):

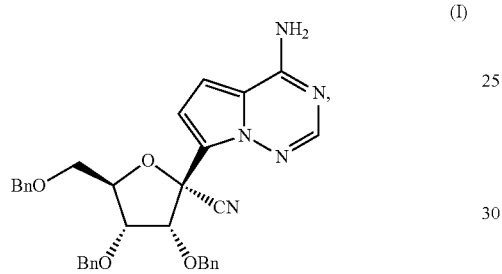

a ninth Lewis acid, and an additive in a ninth reactor to provide a ninth output mixture comprising the compound of Formula (VII) or salt thereof In another embodiment, provided herein is a method of preparing a compound of Formula (VII):

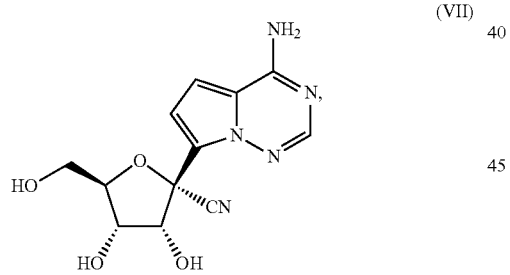

or a salt thereof, the method comprising combining a compound of Formula (I):

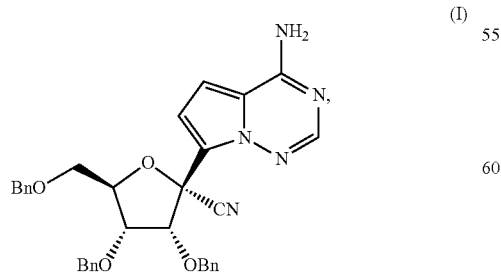

and a tenth Lewis acid in a tenth reactor to provide a tenth output mixture comprising the compound of Formula (VII) or salt thereof, wherein the tenth Lewis acid is selected from the group consisting of aluminum trichloride ($AlCl_3$), aluminum tribromide ($AlBr_3$), titanium(IV) chloride ($TiCl_4$), and tin(IV) chloride ($SnCl_4$).

In another embodiment, provided herein is a method of preparing a compound of Formula (VIII):

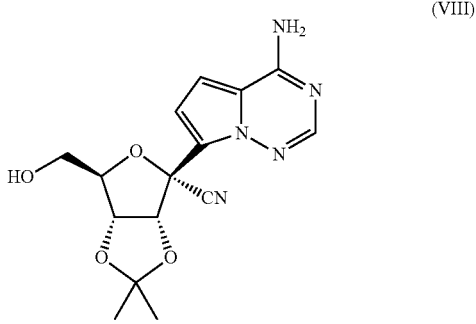 [SMILES: CC1(C)O[C@H]2[C@@H](O1)[C@](C#N)(c1ccc3c(N)ncnn13)O[C@@H]2CO]

or a pharmaceutically acceptable salt thereof, comprising (a) adding an eleventh input mixture to an eleventh reactor, wherein the eleventh input mixture comprises an eleventh acid HX, an eleventh protecting agent, an eleventh solvent, and a compound of Formula (VII):

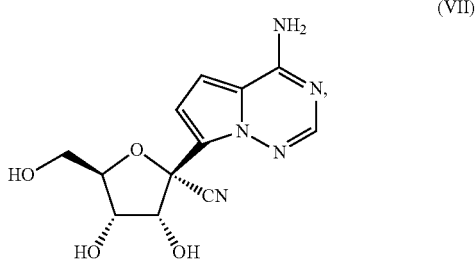 [SMILES: N#C[C@@]1(c2ccc3c(N)ncnn23)O[C@H](CO)[C@@H](O)[C@H]1O]

wherein the eleventh reactor provides an eleventh output mixture comprising an acid salt of Formula (VIII-a):

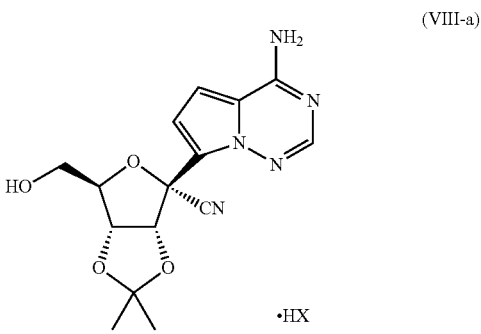

wherein the eleventh acid HX is sulfuric acid, hydrochloric acid, phosphoric acid, benzoic acid, oxalic acid, methanesulfonic acid, benzenesulfonic acid, camphorsulfonic acid, naphthalenesulfonic acid, 1-hydroxy-2-naphthoic acid, 1,5-naphthalenedisulfonic acid, maleic acid, ethanesulfonic acid, p-toluenesulfonic acid, or oxalic acid; the eleventh protecting agent is acetone, 2-methoxypropene, 2,2-dimethoxypropane, an alkyl acetal, or a vinyl ether; and =the eleventh solvent is dichloromethane, methyl acetate, ethyl acetate, isopropyl acetate, tetrahydrofuran, 2-methyltetrahydrofuran, or acetonitrile, or a combination thereof and (b) adding a twelfth input mixture to a twelfth reactor, wherein the twelfth input mixture comprises the eleventh output mixture, a twelfth base, and a twelfth solvent; wherein the twelfth reactor provides a twelfth output mixture comprising the compound of Formula (VIII-a); the twelfth base is sodium bicarbonate, sodium carbonate, potassium bicarbonate, potassium carbonate, sodium acetate, potassium acetate, calcium acetate, or calcium hydroxide; and the twelfth solvent is methanol, ethanol, isopropanol, or water, or a combination thereof In another embodiment, provided herein is a method of preparing a compound of Formula (X):

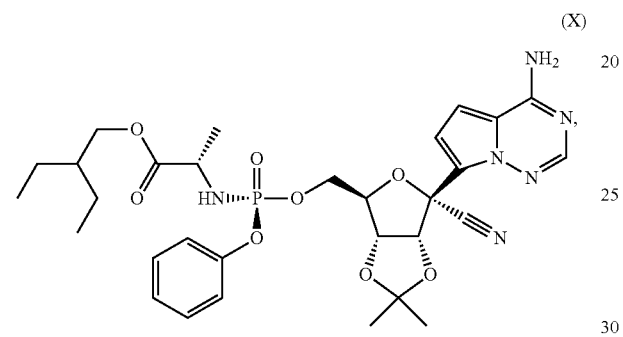

comprising adding a thirteenth input mixture to a thirteenth reactor, wherein the thirteenth input mixture comprises a compound of Formula (VIII):

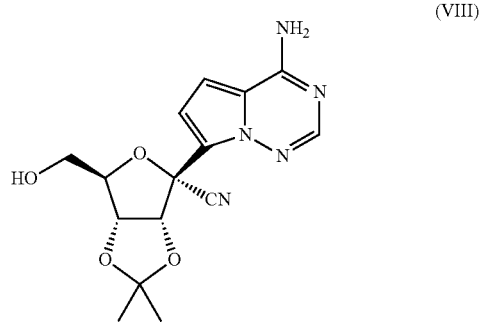 [SMILES: CC1(C)O[C@H]2[C@@H](O1)[C@](C#N)(c1ccc3c(N)ncnn13)O[C@@H]2CO]

or a pharmaceutically acceptable salt thereof, magnesium chloride, diisopropylethylamine, a thirteenth solvent, and a compound of Formula (IX):

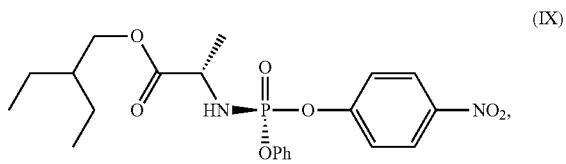 [SMILES: CCC(CC)COC(=O)[C@H](C)N[P@](=O)(Oc1ccccc1)Oc1ccc([N+](=O)[O-])cc1]

wherein the thirteenth reactor provides an thirteenth output mixture comprising the compound of Formula (X); and the thirteenth solvent is dichloromethane, tetrahydrofuran, or 2-methyltetrahydrofuran, or a combination thereof.

DETAILED DESCRIPTION

I. General

Figure 1:
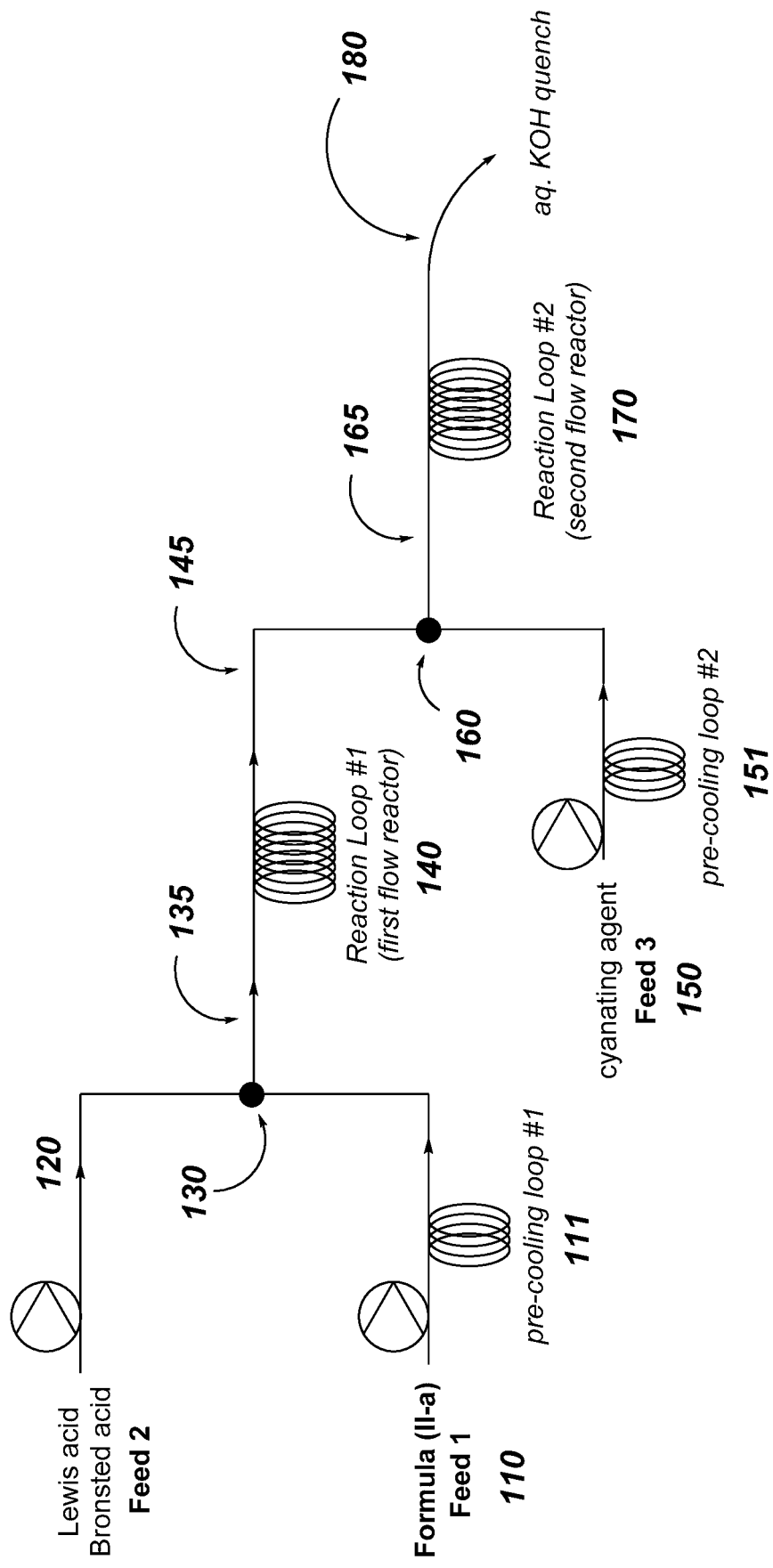
FIG. 1 shows a flow schematic of the method of preparing a compound of Formula (I) as described in Example 7.

The present disclosure describes methods of preparing 1'-cyano nucleosides. The methods described herein relate to efficient, scalable processes that can be performed at any scale, e.g., 1 kg or higher. In some embodiments, the method comprises preparing in a flow reactor a compound of Formula (I):

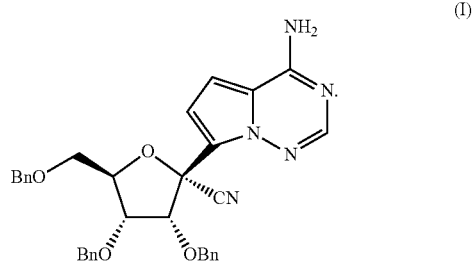

II. Definitions

"About" when referring to a value includes the stated value ±10% of the stated value. For example, about 50% includes a range of from 45% to 55%, while about 20 molar equivalents includes a range of from 18 to 22 molar equivalents. Accordingly, when referring to a range, "about" refers to each of the stated values ±10% of the stated value of each end of the range. For instance, a ratio of from about 1 to about 3 (weight/weight) includes a range of from 0.9 to 3.3.

"Flow reactor" or "tube reactor" refers to a vessel to which chemicals, reagents and solvent are continuously added as a feed mixture, usually at steady state, and configured so that conversion of the chemicals, reagents, and other dependent variables are functions of position and residence time within the reactor. For example, the fluids can flow through the flow reactor as if they were solid plugs or pistons, and reaction time is the same for all flowing material at any given cross section. While material is continuously added to the flow reactor, product is continuously produced via an output mixture until the feed mixture is exhausted, i.e., there is no feed mixture remaining. For example, with respect to the flow schematic shown in FIG. 1, the first flow reactor is represented by the reaction loop 140. With respect to the flow schematic shown in FIG. 1, the second flow reactor is represented by the reaction loop 170.

"Continuously adding" refers to providing a source of chemicals, reagents and solvent as a flowing stream to the reactor in order to provide a stream of product.

"Exhausted" refers to a time point in which the feed mixture of chemicals, reagents and solvent has been completely delivered to a flow reactor.

"Input mixture" as used herein refers to a mixture of one or more reagents and/or solvents that enters a reactor. The reactor can be a batch reactor or a flow reactor.

"First input mixture" as used herein refers to a mixture of one or more reagents and/or solvents that enters the first flow reactor. For example, with respect to the flow schematic shown in FIG. 1, the first input mixture is represented by the stream 135 entering the first flow reactor.

"Second input mixture" as used herein refers to a mixture of one or more reagents and/or solvents that enters the second flow reactor. For example, with respect to the flow schematic shown in FIG. 1, the second input mixture is represented by the stream 165 entering the second flow reactor.

"Output mixture" as used herein refers to a mixture of one or more reagents and/or solvents that exits a reactor. The reactor can be a batch reactor or a flow reactor.

A "first output mixture" as used herein refers to a mixture of one or more compounds and/or solvents that exits the first flow reactor. For example, with respect to the flow schematic shown in FIG. 1, the first output mixture is represented by the stream 145 exiting the first flow reactor.

A "second output mixture" as used herein refers to a mixture of one or more compounds and/or solvents that exits the second flow reactor. For example, with respect to the flow schematic shown in FIG. 1, the second output mixture is represented by the stream 180 exiting the second flow reactor.

"Residence time" in a reactor refers to the period of time one or more components spend on average in a flow reactor. The residence time is a function of flow rate and equipment dimensions.

A "feed mixture" refers to a mixture of reagents and/or solvent prior to input in a flow reactor. Because a chemical reaction can be concentration and temperature dependent, the concentration and temperature of reagents can be prepared prior to combination and/or reaction as an input mixture in a flow reactor. For example, in embodiments illustrated by FIG. 1, a "first feed mixture" comprises the compound of Formula (II-a) represented as stream 110. In embodiments illustrated by FIG. 1, a "second feed mixture" comprises a Lewis acid and a Bronsted acid mixed and provided in a stream 120. In embodiments illustrated by FIG. 1, a "third feed mixture" comprises a cyanating agent mixed and provided in a stream 150.

"Lewis acid" refers to a chemical group capable of accepting an electron pair from a second chemical group capable of donating an electron pair. Lewis acids can be inorganic compounds including boron salts, such as boron trifluoride, or aluminum salts, such as aluminum trichloride; organic compound salts, such as trimethylsilyl trifluoromethanesulfonate (TMSOTf); or metal complexes containing organic and/or inorganic ligands, such as indium(III) chloride or dichlorodiisopropoxytitanium(IV).

"Bronsted acid", "Bronsted acid", or "Bronsted-Lowry acid" refers to an acid capable of donating a proton and forming the conjugate base. Examples of Bronsted acids include inorganic acids such as hydrogen chloride or hydrogen tetrafluoroborate; and organic acids, e.g., carboxylic acids such as trifluoroacetic acid (TFA), or sulfonic acids such as trifluoromethanesulfonic acid.

"Cyanating agent" refers to an agent capable of installing a cyano group (-CN) on a corresponding compound. Cyanating agents include inorganic cyanides, e.g., sodium cyanide, potassium cyanide, tetrabutylammonium cyanide, and organic cyanides such as trialkylsilyl cyanides, e.g., trimethylsilyl cyanide (TMSCN) or tert-butyldimethylsilyl cyanide (TBSCN).

When referring to molar equivalents, "relative" refers to the ratio of the molar amounts of a first component compared to the molar amounts of a second component. For example, 2.0 molar equivalents of trifluoroacetic acid (TFA) relative to the compound of Formula (II-a) refers to an embodiment where there are two times the number of molecules of TFA compared to the molecules of the compound of Formula (II-a).

An amount of a first component "relative to" an amount of a second component in weight refers to the ratio of the weight of the first component and the weight of the second component. For example, 20% (w/w) of trimethylsilyl cyanide (TMSCN) relative to dichloromethane (DCM) refers to a solution of 2 kg TMSCN in 10 kg DCM.

"Volumes" refers to the number of liters (L) of a solvent per kilogram (kg) of a component. For example, 15 volumes of dichloromethane refers to 15 liters per kilogram of the compound of Formula (II-a). As dichloromethane has a density of 1.33 g/mL, 15 volumes corresponds to 20 kg of dichloromethane per 1 kg of the compound of Formula (II-a). Similarly, 8 volumes of water corresponds to 8 kg of water per 1 kg of the compound Formula (II-a). Thus, a reaction involving 250 kg of the compound Formula (II-a) and 15 volumes of dichloromethane includes 3,750 L of dichloromethane.

III. Methods Of Making

The present disclosure describes methods of making
(1) the compound of Formula I, (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile,
(2) the compound of Formula II-a, (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol,
(3) the compound of Formula VII, (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile,
(4) the compound of Formula VIII, (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile, and
(5) the compound of Formula X, 2-ethylbutyl ((S)-(3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)-L-alaninate.

A. Formula (I) From Formula (II-A)

Provided herein are methods of preparing compounds described herein. Provided herein are methods of preparing the compound of Formula (I), (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile:

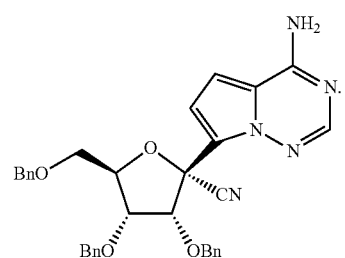

In one embodiment, the present disclosure provides a method of preparing a compound of Formula (I):

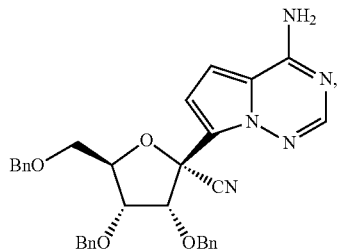

the method comprising: (a) adding a first input mixture to a first flow reactor, wherein the first input mixture comprises a Lewis acid, a Bronsted acid, and a compound of Formula (II-a):

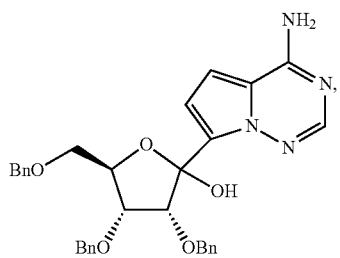

wherein the first flow reactor provides a first output mixture; and (b) adding a second input mixture to a second flow reactor, wherein the second input mixture comprises the first output mixture and a cyanating agent; wherein the second flow reactor provides a second output mixture comprising the compound of Formula (I).

The compound of Formula (I) having the structure:

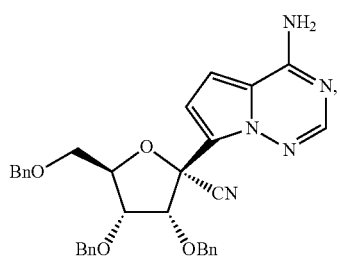

is also known as (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile.

The compound of Formula (II-a) having the structure:

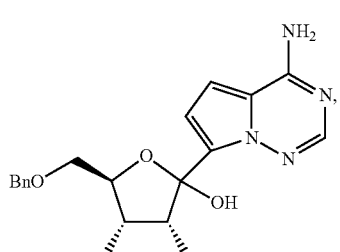

is also known as (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol.

As is generally understood in the art, the compound of Formula (II-a) exists in an equilibrium with a compound of Formula (II-b):

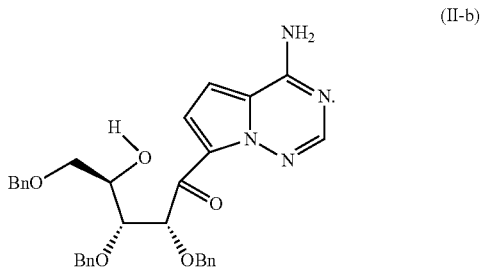

Accordingly, as used herein, the compound of Formula (II-a) when recited alone is understood to mean the compound of Formula (II-a) and/or the compound of Formula (II-b) or any combination of the two species.

In some embodiments, the method of preparing the compound of Formula (I) further comprises a solvent. In some embodiments, the first input mixture, the second input mixture, and/or the third input mixture comprises a solvent. Any suitable solvent can be used in the method of preparing a compound of Formula (I). In some embodiments, the solvent can include esters (e.g., ethyl acetate, isopropyl acetate, n-propyl acetate, butyl acetate, isobutyl acetate), ethers (e.g., diethyl ether, methyl tert-butyl ether, tetrahydrofuran, 2-methyltetrahydrofuran, 1,4-dioxane), aromatic solvents (e.g., toluene, benzene, xylenes), polar aprotic solvents (e.g., N,N-dimethylformamide, N,N-dimethylacetamide, N-methylpyrrolidinone, dimethylsulfoxide), chlorinated solvents (e.g., dichloromethane, chloroform, dichloroethane, chlorobenzene), nitriles (e.g., acetonitrile, propionitrile, butyronitrile), or a combination thereof In some embodiments, the solvent is dichloromethane, chloroform, dichloroethane, or chlorobenzene, or a combination thereof. In some embodiments, the solvent is dichloromethane (DCM).

Any suitable Lewis acid can be used in the method of preparing a compound of Formula (I). In some embodiments, the Lewis acid is tert-butyldimethylsilyl trifluoromethanesulfonate (TBSOTf), triethylsilyl trifluoromethanesulfonate (TESOTf), boron trifluoride ($BF_3$), boron trifluoride etherate ($BF_3$-$OEt_2$), boron trichloride ($BCl_3$), boron trifluoride tetrahydrofuran complex ($BF_3$-THF), magnesium dichloride ($MgCl_2$), magnesium dibromide ($MgBr_2$), magnesium dibromide etherate ($MgBr_2$-$OEt_2$), zinc dichloride ($ZnCl_2$), zinc dibromide ($ZnBr_2$), lithium chloride (LiCl), lithium bromide (LiBr), lithium iodide (LiI), aluminum trichloride ($AlCl_3$), aluminum tribromide ($AlBr_3$), aluminum triiodide ($AlI_3$), dimethylsilyl bis(trifluoromethanesulfonate) ($Me_2Si(OTf)_2$), diethylsilyl bis(trifluoromethanesulfonate) ($Et_2Si(OTf)_2$), dipropylsilyl bis(trifluoromethanesulfonate) ($Pr_2Si(OTf)_2$), diisopropylsilyl bis(trifluoromethanesulfonate) ($iPr_2Si(OTf)_2$), di-tert-butylsilyl bis(trifluoromethanesulfonate) ($(tBu)_2Si(OTf)_2$), tris(pentafluorophenyl)borane ($(C_6F_5)_3B$), trichloromethylsilane ($MeSiCl_3$), dichlorodimethylsilane ($Me_2SiCl_2$), tetrachlorosilane ($SiCl_4$), trimethylsilyl trifluoromethanesulfonate (TMSOTf), trimethylsilyl chloride (TMSCl), trimethylsilyl iodide (TMSI), trimethylsilyl bromide (TMSBr), tert-butyldimethylsilyl chloride (TBSCl), tert-butyldimethylsilyl bromide (TBSBr), tert-butyldimethylsilyl iodide (TBSI), triethylsilyl chloride (TESCl), triethylsilyl bromide (TESBr), triethylsilyl iodide (TESI), samarium(III) chloride (SmCl$_3$), samarium(III) bromide (SmBr$_3$), samarium(II) iodide (SmI$_2$), samarium(III) iodide (SmI$_3$), scandium(III) iodide (ScI$_3$), scandium(III) bromide (ScBr$_3$), scandium(III) iodide (ScI$_3$), samarium(III) trifluoromethanesulfonate (Sm(OTf)$_3$), scandium(III) trifluoromethanesulfonate (Sc(OTf)$_3$), titanium(IV) chloride (TiCl$_4$), titanium(IV) isopropoxide (Ti(OiPr)$_4$), chlorotriisopropoxytitanium(IV) (Ti(OiPr)$_3$Cl), dichlorodiisopropoxytitanium(IV) (Ti(OiPr)$_2$Cl$_2$), trichloroisopropoxytitanium(IV) (Ti(OiPr)Cl$_3$), zinc tetrafluoroborate (Zn(BF$_4$)$_2$), lithium tetrafluoroborate (LiBF$_4$), magnesium tetrafluoroborate (Mg(BF$_4$)$_2$), zirconium chloride (ZrCl$_4$), iron(II) chloride (FeCl$_2$), iron(III) chloride (FeCl$_3$), iron(II) bromide (FeBr$_2$), iron(III) bromide (FeBr$_3$), iron(II) iodide (FeI$_2$), iron(III) iodide (FeI$_3$), copper(I) trifluoromethanesulfonate (Cu(OTf)), 4-toluenesulfonyl chloride, benzenesulfonyl chloride, 4-toluenesulfonyl triflate, benzenesulfonyl triflate, methylsulfonyl chloride, methylsulfonic anhydride, indium(III) chloride (InCl$_3$), indium(III) bromide (InBr$_3$), indium(III) iodide (InI$_3$), indium(III) trifluoromethanesulfonate (In(OTf)$_3$), magnesium sulfate (MgSO$_4$), or sodium sulfate (Na$_2$SO$_4$); or a combination thereof.

In some embodiments, the Lewis acid is a trialkylsilyl Lewis acid. In some embodiments, the Lewis acid is trimethylsilyl trifluoromethanesulfonate (TMSOTf), trimethylsilyl chloride (TMSCl), trimethylsilyl iodide (TMSI), trimethylsilyl bromide (TMSBr), tert-butyldimethylsilyl chloride (TBSCl), tert-butyldimethylsilyl bromide (TBSBr), tert-butyldimethylsilyl iodide (TBSI), triethylsilyl chloride (TESCl), triethylsilyl bromide (TESBr), triethylsilyl iodide (TESI), tert-butyldimethylsilyl trifluoromethanesulfonate (TBSOTf, or triethylsilyl trifluoromethanesulfonate (TESOTf). In some embodiments, the Lewis acid is trimethylsilyl trifluoromethanesulfonate (TMSOTf).

The Lewis acid can be present in any suitable amount. For example, the Lewis acid can be present in an amount of at least 1 molar equivalent relative to the compound of Formula (II-a), such as about 2, about 3, about 4, about 5, about 6, about 7, about 8, about 9, or about 10 molar equivalents. In some embodiments, the Lewis acid can be present in an amount of from about 1.0 to about 10.0 molar equivalents relative to the compound of Formula (II-a). The Lewis acid can also be present in an amount of from about 3.0 to about 9.0 molar equivalents relative to the compound of Formula (II-a), such as from about 4.0 to about 8.0 molar equivalents. In some embodiments, the Lewis acid can be present in an amount of from about 5.0 to about 7.0 molar equivalents relative to the compound of Formula (II-a). In some embodiments, the Lewis acid can be present in an amount of about 6.0 molar equivalents relative to the compound of Formula (II-a).

In some embodiments, the Lewis acid is TMSOTf. In some embodiments, the second input mixture comprises TMSOTf The TMSOTf can be present in any suitable amount. For example, TMSOTf can be present in an amount of at least 1 molar equivalent relative to the compound of Formula (II-a), such as about 2, about 3, about 4, about 5, about 6, about 7, about 8, about 9, or about 10 molar equivalents. TMSOTf can also be present in an amount of from about 1.0 to about 10.0 molar equivalents relative to the compound of Formula (II-a). In some embodiments, the TMSOTf is present in an amount of from about 4.0 to about 8.0, or from about 3.0 to about 9.0, molar equivalents relative to the compound of Formula (II-a). In some embodiments, TMSOTf is present in an amount of from about 5.0 to about 7.0 molar equivalents relative to the compound of Formula (II-a). In some embodiments, TMSOTf is present in an amount of about 6.0 molar equivalents relative to the compound of Formula (II-a).

Any suitable Bronsted acid can be used in the method of preparing a compound of Formula (I) described herein. The Bronsted acid can be benzenesulfonic acid, hydrogen chloride, hydrogen bromide, hydrogen iodide, 4-toluenesulfonic acid, triflic acid, trifluoroacetic acid, 4-nitrobenzoic acid, methanesulfonic acid, sulfuric acid, phosphoric acid, acetic acid, formic acid, trifluoroacetic acid (TFA), trifluoromethanesulfonic acid, 4-fluorobenzoic acid, pivalic acid, hydrogen tetrafluoroborate (HBF$_4$), nitric acid, 4-chlorobenzoic acid, pentafluorophenol, hydrogen hexafluorophosphate (HPF$_6$), camphorsulfonic acid; or a combination thereof. In some embodiments, the Bronsted acid is trifluoroacetic acid (TFA), trifluoromethanesulfonic acid, 4-fluorobenzoic acid, pivalic acid, hydrogen tetrafluoroborate (HBF$_4$), nitric acid, 4-chlorobenzoic acid, pentafluorophenol, or hydrogen hexafluorophosphate (HPF$_6$). In some embodiments, the Bronsted acid is trifluoroacetic acid.

The Bronsted acid can be present in any suitable amount. For example, the Bronsted acid can be present in an amount of at least 0.5 molar equivalents relative to the compound of Formula (II-a), such as about 0.6, about 0.7, about 0.8, about 0.9, about 1.0, about 1.1, about 1.2, about 1.3, about 1.4, or about 1.5 molar equivalents. In some embodiments, the Bronsted acid is present in an amount of from about 0.5 to about 1.5 molar equivalents. In some embodiments, the Bronsted acid is present in an amount of from about 0.7 to about 1.3 molar equivalents. In some embodiments, the Bronsted acid is present in an amount of from about 0.8 to about 1.2 molar equivalents. In some embodiments, the Bronsted acid is present in an amount of about 1.0 molar equivalents relative to the compound of Formula (II-a).

In some embodiments, the Bronsted acid is trifluoroacetic acid (TFA). The trifluoroacetic acid can be present in any suitable amount. For example, the trifluoroacetic acid can be present in an amount of at least 0.5 molar equivalents relative to the compound of Formula (II-a), such as about 0.6, about 0.7, about 0.8, about 0.9, about 1.0, about 1.1, about 1.2, about 1.3, about 1.4, or about 1.5 molar equivalents. In some embodiments, the trifluoroacetic acid is present in an amount of from about 0.7 to about 1.3, from about 0.9 to about 1.1, or from about 0.6 to about 1.4 molar equivalents relative to the compound of Formula (II-a). In some embodiments, the trifluoroacetic acid is present in an amount of from about 0.5 to about 1.5 molar equivalents relative to the compound of Formula (II-a). In some embodiments, the trifluoroacetic acid is present in an amount of from about 0.8 to about 1.2 molar equivalents relative to the compound of Formula (II-a). In some embodiments, the trifluoroacetic acid is present in an amount of about 1.0 molar equivalents relative to the compound of Formula (II-a).

Any suitable cyanating agent can be used in the method of preparing a compound of Formula (I). In some embodiments, the cyanating agent is trimethylsilyl cyanide (TMSCN), tert-butyldimethylsilyl cyanide (TBSCN), triethylsilyl cyanide (TESCN), hydrogen cyanide (HCN), potassium cyanide (KCN), sodium cyanide (NaCN), 4-toluenesulfonyl cyanide, copper(I) cyanide (CuCN), copper(I) cyanide-lithium chloride (CuCN-LiCl), lithium cyanide (LiCN), zinc cyanide (Zn(CN)$_2$), potassium ferrocyanide (K$_4$[Fe(CN)$_6$]), tetrabutylammonium cyanide, tetramethylammonium cyanide, tetraethylammonium cyanide, tetraalkylammonium cyanide with alkyl independently being methyl, ethyl, propyl, isopropyl, butyl, isobutyl, tert-butyl, pentyl, or hexyl, tributyltin cyanide, trimethyltin cyanide, triethyltin cyanide, tripropyltin cyanide, trialkyltin cyanide with alkyl independently being methyl, ethyl, propyl, isopropyl, butyl, isobutyl, tert-butyl, pentyl, or hexyl, 2-hydroxy-2-methylpropanenitrile; or a combination thereof.

In some embodiments, the cyanating agent is trimethylsilyl cyanide (TMSCN), tert-butyldimethylsilyl cyanide (TBSCN), triethylsilyl cyanide (TESCN), tetrabutylammonium cyanide, tetramethylammonium cyanide, or tetraethylammonium cyanide. In some embodiments, the cyanating agent is TMSCN.

The cyanating agent can be present in any suitable amount. For example, the cyanating agent can be present in an amount of at least 1 molar equivalents relative to the compound of Formula (II-a), such as about 2, about 3, about 4, about 5, about 6, about 7, about 8, about 9, or about 10 molar equivalents. In some embodiments, the cyanating agent can be present in an amount of from about 1.0 to about 10.0 molar equivalents relative to the compound of Formula (II-a). The cyanating agent can also be present in an amount of from about 3.0 to about 9.0 molar equivalents relative to the compound of Formula (II-a), such as from about 4.0 to about 8.0 molar equivalents. In some embodiments, the cyanating agent can be present in an amount of from about 5.0 to about 7.0 molar equivalents relative to the compound of Formula (II-a). In some embodiments, the cyanating agent is present in an amount of about 6.0 molar equivalents relative to the compound of Formula (II-a).

In some embodiments, the cyanating agent is TMSCN. In some embodiments, the second input mixture comprises TMSCN. The TMSCN can be present in any suitable amount. For example, TMSCN can be present in an amount of at least 1 molar equivalent relative to the compound of Formula (II-a), such as about 2, about 3, about 4, about 5, about 6, about 7, about 8, about 9, or about 10 molar equivalents. In some embodiments, the TMSCN can also be present in an amount of from about 1.0 to about 10.0 molar equivalents relative to the compound of Formula (II-a). In some embodiments, the TMSCN is present in an amount of from about 4.0 to about 8.0, or from about 3.0 to about 9.0, molar equivalents relative to the compound of Formula (II-a). In some embodiments, TMSCN is present in an amount of from about 5.0 to about 7.0 molar equivalents relative to the compound of Formula (II-a). In some embodiments, the TMSCN is present in an amount of about 6.0 molar equivalents relative to the compound of Formula (II-a).

In some embodiments, the Lewis acid is trifluoromethanesulfonate (TMSOTf), the Bronsted acid is trifluoroacetic acid (TFA), the solvent is dichloromethane, and the cyanating agent is trimethylsilyl cyanide (TMSCN).

In some embodiments, the method of preparing a compound of Formula (I):

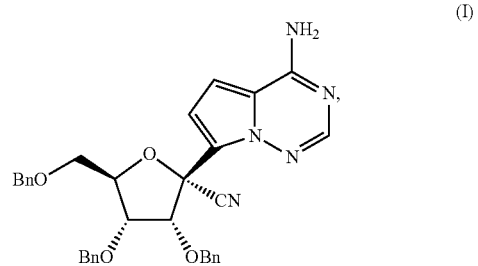

comprises: (a) adding a first input mixture to a first flow reactor, wherein the first input mixture comprises trimethylsilyl trifluoromethanesulfonate (TMSOTf), trifluoroacetic acid (TFA), dichloromethane (DCM), and a compound of Formula (II-a):

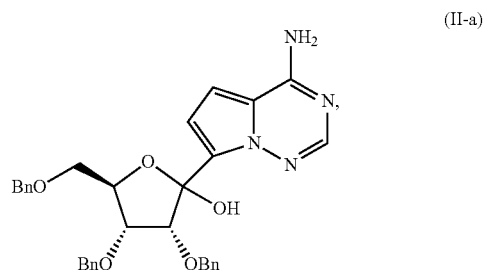

wherein the first flow reactor provides a first output mixture; and (b) adding a second input mixture to a second flow reactor, wherein the second input mixture comprises the first output mixture and trimethylsilyl cyanide (TMSCN); wherein the second flow reactor provides a second output mixture comprising the compound of Formula (I).

The method of the present disclosure can be used to prepare the compound of Formula (I) from the compound of Formula (II-a) in any desired quantity, for example, from gram to kilogram quantities. Because the method described herein is a continuous flow method, the method can be used to prepare any quantity of the compound of Formula (I), including amounts greater than the specific amounts described herein. In some embodiments, the method comprises at least 5 g, 10 g, 15 g, 20 g, 25 g, 30 g, 35 g, 40 g, 45 g, 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 250 kg, 280 kg, 300 kg, 400 kg, 500 kg, or at least 1000 kg or more of the compound of Formula (II-a). In some embodiments, the method comprises from about 50 g to about 1000 kg, e.g., from about 50 g to about 300 kg, of the compound of Formula (II-a). In some embodiments, the method includes at least 1 kg of the compound of Formula (II-a). In some embodiments, the method includes at least 100 kg of the compound of Formula (II-a). For example, the method can comprise at least 280 kg of the compound of Formula (II-a). In some embodiments, the method comprises from about 200 g to about 300 kg of the compound of Formula (II-a). In some embodiments, the method comprises from about 250 g to about 300 kg of the compound of Formula (II-a).

The method of preparing the compound of Formula (I) described herein comprises use of flow reactors, e.g., a first flow reactor and a second flow reactor. In some embodiments, the method comprises continuously adding the first input mixture to the first flow reactor until the first input mixture is exhausted. In some embodiments, the method comprises continuously adding the second input mixture to the second flow reactor until the first output mixture is exhausted.

The first input mixture can include a number of components that can be combined from one or more feed mixtures prior to adding to the first flow reactor. For example, the first input mixture can include a first feed mixture, e.g., Feed 1 in FIG. 1, comprising the compound of Formula (II-a) and a solvent such as dichloromethane. The compound of Formula (II-a) can be present in the solvent in any suitable amount, such as, but not limited to, from about 3% to about 30% (w/w), or about 3%, about 4%, about 5%, about 6%, about 7%, about 8%, about 9%, about 10%, about 15%, about 20%, about 25%, or about 30% of the compound of Formula (II-a) relative to the solvent. In some embodiments, the compound of Formula (II-a) is present in a solution of from about 3% to about 10% (w/w) relative to the dichloromethane. In some embodiments, the compound of Formula (II-a) can be present in a solution of about 5% (w/w) relative to the dichloromethane.

The first input mixture can also include a second feed mixture, e.g., Feed 2 in FIG. 1, comprising a Lewis acid and a solvent such as dichloromethane. The Lewis acid, such as TMSOTf, can be present in any suitable amount such as, but not limited to, from about 10% to about 60% (w/w) or from about 20% to about 50% (w/w), or about 20%, about 25%, about 30%, about 35%, about 40%, about 45%, or about 50% of the Lewis acid relative to the solvent. In some embodiments, the Lewis acid is present in an amount of from about 30% to about 50% (w/w) relative to the solvent. In some embodiments, the Lewis acid is present in an amount of about 40% (w/w) relative to the solvent.

The second feed mixture also includes a Bronsted acid. The Bronsted acid, such as trifluoroacetic acid, can be present in any suitable amount such as, but not limited to, from about 1% to about 5% (w/w), e.g., about 1%, about 2%, about 2.5%, about 3%, about 3.5%, about 4%, about 4.5%, or about 5%, of the trifluoroacetic acid relative to the solvent. In some embodiments, the second feed mixture further comprises from about 2% to about 5% (w/w) of the trifluoroacetic acid relative to dichloromethane. Alternatively, the solvent of the second feed mixture can be present in an amount from about 1 to about 10 volumes, from about 1 to about 8 volumes, from about 2 to about 7 volumes, from about 3 to about 6 volumes, or from about 4 to about 5 volumes. In some embodiments, the solvent in the second feed mixture can be present in an amount of about 1, or 2, 3, 4, 5, 6, 7, 8, 9, or about 10 volumes. In some embodiments, the solvent in the second feed mixture can be present in an amount of about 4.0, or 4.1, 4.2, 4.3, 4.4, 4.5, 4.6, 4.7, 4.8, 4.9, or about 5.0 volumes. In some embodiments, the solvent of the second feed mixture can be present in an amount of about 4.4 volumes. The volumes can be calculated relative to any component in the method. In some embodiments, the volumes of solvent in the second feed mixture are relative to the compound of Formula (II-a).

In some embodiments, the method of preparing the compound of Formula (I) provided herein comprises combining a first feed mixture comprising from about 3% to about 7% (w/w) of the compound of Formula (II-a) relative to dichloromethane, and a second feed mixture comprising from about 30% to about 50% (w/w) of the TMSOTf relative to dichloromethane and from about 2% to about 5% (w/w) of the trifluoroacetic acid relative to dichloromethane, thus forming the first input mixture. Alternatively, the solvent of the first feed mixture can be present in an amount from about 1 to about 50 volumes, from about 5 to about 15 volumes, from about 10 to about 20 volumes, from about 12 to about 18 volumes, or from about 14 to about 16 volumes. In some embodiments, the solvent in the first feed mixture can be present in an amount of about 10, or 11, 12, 13, 14, 15, 16, 17, 18, 19, or about 20 volumes. In some embodiments, the solvent of the first feed mixture can be present in an amount of about 15 volumes. The volumes can be calculated relative to any component in the method. In some embodiments, the volumes of solvent in the first feed mixture are relative to the compound of Formula (II-a).

In some embodiments, the method of preparing the compound of Formula (I) provided herein further comprises combining a third feed mixture, e.g., Feed 3 in FIG. 1, and the first output mixture, thus forming the second input mixture. In some embodiments, the third feed mixture comprises the cyanating agent and a solvent. In some embodiments, the method comprises combining the first output mixture and a third feed mixture comprising from about 10% to about 50% (w/w) of the TMSCN relative to dichloromethane, thus forming the second input mixture. In some embodiments, the method comprises combining the first output mixture and a third feed mixture comprising from about 10% to about 30% (w/w) of the TMSCN relative to dichloromethane, thus forming the second input mixture. Alternatively, the solvent of the third feed mixture can be present in an amount from about 1 to about 10 volumes, from about 1 to about 8 volumes, from about 2 to about 7 volumes, from about 3 to about 6 volumes, or from about 4 to about 5 volumes. In some embodiments, the solvent in the third feed mixture can be present in an amount of about 1, or 2, 3, 4, 5, 6, 7, 8, 9, or about 10 volumes. In some embodiments, the solvent in the third feed mixture can be present in an amount of about 4.0, or 4.1, 4.2, 4.3, 4.4, 4.5, 4.6, 4.7, 4.8, 4.9, or about 5.0 volumes. In some embodiments, the solvent of the third feed mixture can be present in an amount of about 4.5 volumes. The volumes can be calculated relative to any component in the method. In some embodiments, the volumes of solvent in the third feed mixture are relative to the compound of Formula (II-a).

In some embodiments, the third feed mixture comprises from about 10% to about 50% (w/w) of the TMSCN relative to dichloromethane. In some embodiments, the third feed mixture comprises from about 10% to about 30% (w/w) of the TMSCN relative to dichloromethane. In some embodiments, the third feed mixture comprises about 10%, about 15%, about 20%, about 25%, about 30%, about 35%, about 40%, about 45%, or about 50%, of the TMSCN relative to dichloromethane.

The TMSCN in the third feed mixture can be present in any suitable amount. For example, TMSCN can be present in an amount of at least 1 molar equivalent relative to the compound of Formula (II-a), such as about 1, about 2, about 3, about 4, about 5, about 6, about 7, about 8, about 9, or about 10 molar equivalents. TMSCN can also be present in an amount of from about 3.0 to about 9.0 molar equivalents relative to the compound of Formula (II-a), such as from about 4.0 to about 8.0 molar equivalents. In some embodiments, TMSCN can be present in an amount of from about 5.0 to about 7.0 molar equivalents relative to the compound of Formula (II-a). In some embodiments, TMSCN is present in an amount of about 6.0 molar equivalents relative to the compound of Formula (II-a).

The feed mixtures can be provided to the reactors in an appropriate flow rate to prepare the compound of Formula (I). Flow rate can change based on equipment dimensions. For example, addition of the first input mixture to the first flow reactor can be performed at any rate suitable to provide a first output mixture. Similarly, addition of the second input mixture to the second flow reactor can be performed at any rate suitable to provide a second output mixture.

The residence time of the first input mixture in the first flow reactor is any time sufficient to provide a first output mixture. In some embodiments, the residence time of the first input mixture in the first flow reactor is from about 0.1 to about 30 minutes, such as about 0.1, about 0.2, about 0.3, about 0.4, about 0.5, about 0.6, about 0.7, about 0.8, about 0.9, about 1, about 2, about 3, about 4, or about 5 minutes.

In some embodiments, the residence time in the first flow reactor is from about 0.1 to about 10 minutes. In some embodiments, the residence time of the first input mixture in the first flow reactor is from about 0.1 to about 20 minutes, from about 0.1 to about 10 minutes, from about 0.1 to about 5 minutes, from about 0.2 to about 5 minutes, or from about 0.3 to about 0.7 minutes. In some embodiments, the residence time of the first input mixture in the first flow reactor is about 0.5 minute.

The residence time of the second input mixture in the second flow reactor is any time sufficient to provide a second output mixture. In some embodiments, the residence time of the second input mixture in the second flow reactor is from about 0.1 to about 30 minutes, such as about 0.5, about 0.6, about 0.7, about 0.8, about 0.9, about 1, about 2, about 3, about 4, about 5, about 6, about 7, about 8, about 9, or about 10 minutes. In some embodiments, the residence time of the second input mixture in the second flow reactor is from about 0.1 to about 10 minutes. In some embodiments, the residence time of the second input mixture in the second flow reactor is from about 0.5 to about 10 minutes, from about 0.2 to about 20 minutes, from about 0.5 to about 5 minutes, from about 0.4 to about 10 minutes, or from about 1 to about 3 minutes. In some embodiments, the residence time of the second input mixture in the second flow reactor is about 2 minutes.

The method of preparing the compound of Formula (I) can be performed at any suitable temperature. For example, the temperature can be from about −120° C. to about 20° C., e.g., from about −60° C. to about 0° C., such as at about −60° C., about −50° C., about −40° C., about −30° C., about −20° C., about −10° C. In some embodiments, the temperature is from about −40° C. to about −20° C. In some embodiments, the first flow reactor and the second flow reactor are each independently maintained at a temperature of from about −40° C. to about −20° C. In some embodiments, the first flow reactor is maintained at a temperature of from about −40° C. to about −20° C. In some embodiments, the second flow reactor is maintained at a temperature of from about −40° C. to about −20° C. In some embodiments, the first flow reactor and the second flow reactor are each independently maintained at a temperature of from about −35° C. to about −25° C. In some embodiments, the first flow reactor and the second flow reactor are both maintained at a temperature of about −30° C.

The temperature of the feed mixtures can be adjusted according to the reaction and equipment used as appropriate for effective conversion to the product at a desired yield and purity. The temperature of one or more of the feed mixtures can be the same or different. In some embodiments, the temperature of one or more feed mixture is adjusted to a comparable temperature as the first flow reactor and/or the second flow reactor prior to forming the first input mixture and/or the second input mixture. Accordingly, the temperature of the first feed mixture, the second feed mixture, the third feed mixture, and/or the first output mixture can be from about −120° C. to about 30° C., e.g., from about −60° C. to about 0° C., such as at about −60 ° C., about −50° C., about −40° C., about −30° C., about −20° C., about −10° C. In some embodiments, the temperature is from about −40° C. to about −20° C.

In some embodiments, the first feed mixture, the third feed mixture, and/or the first output mixture are each independently adjusted to a temperature of from about −40° C. to about −20° C., from about −35° C. to about −25° C., such as about −30° C.

In some embodiments, the first feed mixture is cooled to about −35° C. to about −25° C., such as about −30° C. prior to mixing with the second feed mixture to obtain the first input mixture. In some embodiments, the method comprises cooling the first feed mixture to a temperature of from about −35° C. to about −25° C. prior to combining with the second feed mixture. In some embodiments, the temperature of the second feed mixture prior to combining with the first feed mixture is from about 20° C. to about 30° C., e.g. about 22° C. In some embodiments, the temperature of the second feed mixture is from about 17° C. to about 27° C. prior to combining with the first feed mixture.

In some embodiments, the first feed mixture is cooled to from about −35° C. to about 25° C., such as about −30° C., and mixed with the second feed mixture to obtain the first input mixture, wherein the temperature of the second feed mixture is from about 20° C. to about 30° C., e.g., about 22° C.

In some embodiments, the method comprises cooling the third feed mixture to about 35° C. to about −25° C. prior to combining with the first output mixture. In some embodiments, the third feed mixture is cooled to about −35° C. to about −25° C., such as about −30° C., prior to mixing with the first output mixture to obtain the second input mixture.

An illustrative diagram of embodiments of the method of preparing the compound of Formula (I) from the compound of Formula (II-a) described herein is shown in FIG. 1. The first feed mixture (Feed 1) (110) comprises the compound of Formula (II-a) which can be mixed in a suitable solvent such as DCM. Feed 1 is fed into a pre-cooling loop #1 (111) maintained at a first temperature, before combining with the second feed mixture (Feed 2) (120) at intersection #1 (130) to form a first input mixture (135). The second feed mixture (Feed 2) comprises a Lewis acid and a Bronsted acid, such as TMSOTf and TFA, that can be mixed in a suitable solvent such as DCM and maintained at a second temperature. The first input mixture is fed into the first flow reactor (140) maintained at a third temperature during a first residence time to provide a first output mixture (145). The third feed mixture (Feed 3) (150) comprising a cyanating agent, such as TMSCN, mixed in a suitable solvent, such as DCM, is fed into a pre-cooling loop #2 (151) maintained at a fourth temperature. The first output mixture 145 and the third feed mixture from pre-cooling loop 151 are combined at intersection #2 (160) to form a second input mixture (165). The second input mixture is fed into the second flow reactor (170) maintained at a fifth temperature during a second residence time to provide a second output mixture (180). The second output mixture 180 comprising the compound of Formula (I) is then fed into an aqueous potassium hydroxide solution maintained at a sixth temperature for workup.

In some embodiments, the first temperature is from about −60° C. to about 0° C. In some embodiments, the first temperature is from about −40° C. to about −20° C. In some embodiments, the first temperature is from about −35° C. to about −25° C. In some embodiments, the first temperature is about −40° C., about −30° C., about −20° C., or about −10° C. In some embodiments, the first temperature is about −30° C.

In some embodiments, the second temperature is from about 0° C. to about 30° C. In some embodiments, the second temperature is from about 15° C. to about 25° C. In some embodiments, the second temperature is from about 17° C. to about 27° C. In some embodiments, the second temperature is about 0° C., about 10° C., about 20° C., or about 30° C. In some embodiments, the second temperature is about 22° C.

In some embodiments, the third temperature is from about −60° C. to about 0° C. In some embodiments, the third temperature is from about −40° C. to about −20° C. In some embodiments, the third temperature is from about −35° C. to about −25° C. In some embodiments, the third temperature is about −40° C., about −30° C., about −20° C., or about −10° C. In some embodiments, the third temperature is about −30° C.

In some embodiments, the fourth temperature is from about −60° C. to about 0° C. In some embodiments, the fourth temperature is from about −40° C. to about −20° C. In some embodiments, the fourth temperature is from about −35° C. to about −25° C. In some embodiments, the fourth temperature is about −40° C., about −30° C., about −20° C., or about −10° C. In some embodiments, the fourth temperature is about −30° C.

In some embodiments, the fifth temperature is from about −60° C. to about 0° C. In some embodiments, the fifth temperature is from about −40° C. to about −20° C. In some embodiments, the fifth temperature is from about −35° C. to about −25° C. In some embodiments, the fifth temperature is about −40° C., about −30° C., about −20° C., or about −10° C. In some embodiments, the fifth temperature is about −30° C.

In some embodiments, the sixth temperature is from about −60° C. to about 0° C. In some embodiments, the sixth temperature is from about −20° C. to about 0° C. In some embodiments, the sixth temperature is from about −15° C. to about −5° C. In some embodiments, the sixth temperature is about −30° C., about −20° C., about −10° C., or about 0° C. In some embodiments, the sixth temperature is about −10° C.

The method of the present invention can be performed at any suitable pressure. For example, the method can be at atmospheric pressure. The first input mixture and/or the second input mixture can be also be exposed to any suitable environment, such as atmospheric gases, or inert gases such as nitrogen or argon.

The method can further comprise isolating the compound of Formula (I) from the second output mixture. In some embodiments, the method further comprises isolating the compound of Formula (I) from the second output mixture. Such isolation methods can include suitable workup or extraction conditions, such as extraction with one or more organic solvents, or washing with an aqueous solution, e.g., a sodium chloride solution. In some embodiments, the method comprises adding the second output mixture to a solution of aqueous potassium hydroxide to form a biphasic mixture comprising an organic layer.

The temperature of adding the second output mixture to a solution of potassium hydroxide can be at any suitable temperature. For example, the temperature of adding the second output mixture to a solution of potassium hydroxide can be from about −20° C. to about 0° C., such as at about −20° C., about −15° C., about −10° C., about −5° C., or about 0° C. In some embodiments, the temperature can be from about −15° C. to about −5° C. In some embodiments, the temperature of adding the second output mixture to a solution of potassium hydroxide is at about −10° C.

In some embodiments, the biphasic mixture can include a second organic solvent for solubility purposes, for ease of distillation, or other purposes. The second organic solvent added to the biphasic mixture can be any suitable organic solvent, including, but not limited to, dichloromethane and other halogenated solvents, as well as diethyl ether, tetrahydrofuran, isopropanol, hexanes, benzene, toluene, and other non-halogenated solvents. In some embodiments, the second organic solvent is isopropanol. In some embodiments, the method comprises adding isopropanol to the biphasic mixture.

In some embodiments, the method comprises isolating the organic layer from the biphasic mixture.

In some embodiments, the method comprises adding toluene to the organic layer. The organic layer can be co-distilled with toluene to precipitate the compound of Formula (I).

In some embodiments, the method comprises concentrating the organic layer.

In some embodiments, the compound of Formula (I) is collected and dried under vacuum. The temperature of the drying can be at any suitable temperature that is not expected to compromise the quality of the compound. In some embodiments, the drying temperature is from about 20° C. to about 80° C., such as about 20° C., about 30° C., about 40° C., about 50° C., about 60° C., about 70° C., or about 80° C. In some embodiments, the drying temperature is about 60° C. In some embodiments, the drying temperature is from about 55° C. to about 65° C. In some embodiments, the drying temperature is from about 50° C. to about 70° C.

The method of the present disclosure can provide the compound of Formula (I) in any suitable yield. For example, the compound of Formula (I) can be prepared in a yield of at least 50%, 55%, 60%, 65%, 70%, 75%, 80%, 85%, 90%, 95%, 97%, 98%, or at least 99%. In some embodiments, the yield of the compound of Formula (I) is from about 60% to about 100%. In some embodiments, the yield of the compound of Formula (I) is from about 60% to about 90%. In some embodiments, the yield of the compound of Formula (I) is from about 70% to about 80% or from about 75% to about 85%. In some embodiments, the yield of the compound of Formula (I) is from about 70% to about 95%. In some embodiments, the yield of the compound of Formula (I) is from about 70% to about 90%. In some embodiments, the yield of the compound of Formula (I) is from about 75% to about 90%. In some embodiments, the yield of the compound of Formula (I) is from about 75% to about 95%. In some embodiments, the yield of the compound of Formula (I) is from about 80% to about 95%. In some embodiments, the yield of the compound of Formula (I) is from about 80% to about 90%. In some embodiments, the yield of the compound of Formula (I) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (I) is about 78%. In some embodiments, the yield of the compound of Formula (I) is from about 70% to about 80%. In some embodiments, the yield of the compound of Formula (I) is from about 70% to about 90%.

The method of the present disclosure can provide the compound of Formula (I) in any suitable purity. For example, the compound of Formula (I) can be prepared in a purity of from about 90% to about 100%, such as from about 95% to about 100% or from about 98% to about 100%. In some embodiments, the purity of the compound of Formula (I) is from about 98% to about 100%. In some embodiments, the compound of Formula (I) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (I) is prepared in a purity of about 99.9%. In some embodiments, the compound of Formula (I) is prepared in a purity of from about 95% to about 99.999%, from about 98% to about 99.999%, from about 98% to about 99.99%, or from about 99% to about 99.99%.

B. Formula (II-A)

Also provided herein are methods of preparing the compound of Formula (II-a), (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol:

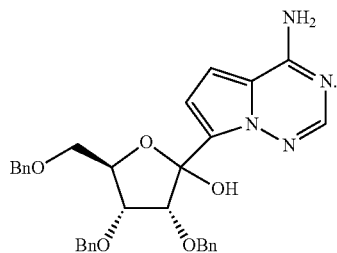 [SMILES: Nc1ncnn2c(C3(O)O[C@H](COCc4ccccc4)[C@@H](OCc4ccccc4)[C@H]3OCc3ccccc3)ccc12]

In some embodiments, the method of preparing a compound of Formula (I) further comprises preparing a compound of Formula (II-a) by any method described herein.

1. Formula (II-a) from Formula (III)

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

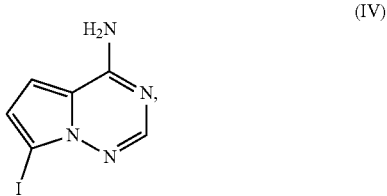 [SMILES: Nc1ncnn2c(I)ccc12]

wherein the third reactor provides a third output mixture; and (d) adding a fourth input mixture to a fourth reactor, wherein the fourth input mixture comprises the third output mixture, a fourth catalyst, a fourth additive, and a compound of Formula (III):

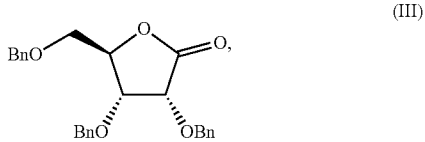 [SMILES: O=C1O[C@H](COCc2ccccc2)[C@@H](OCc2ccccc2)[C@H]1OCc1ccccc1]

wherein the fourth reactor provides a fourth output mixture comprising the compound of Formula (II-a).

Any suitable fourth catalyst can be used in the method to prepare the compound of Formula (II-a). In some embodiments, the fourth catalyst is a lanthanide salt. In some embodiments, the fourth catalyst is selected from the group consisting of $NdCl_3$, $YCl_3$, $CeCl_3$, and $LaCl_3$. In some embodiments, the fourth catalyst is $NdCl_3$ or $CeCl_3$. In some embodiments, the fourth catalyst is $CeCl_3$. In some embodiments, the fourth catalyst is $NdCl_3$.

Any suitable form of the fourth catalyst can be used in the method to prepare the compound of Formula (II-a). For example, the fourth catalyst can be a hydrate or solvate form thereof. In some embodiments, the fourth catalyst is anhydrous. In some embodiments, the fourth catalyst is a solvate. Representative solvate forms of the fourth catalyst include, but are not limited to, an ether solvent. The solvate form of the fourth catalyst can include the solvate in any suitable molar ratio, for example, solvate, disolvate, trisolvate, etc. In some embodiments, the fourth catalyst is a THF solvate. In some embodiments, the fourth catalyst is a hydrate. The hydrate forms of the fourth catalyst can be in any suitable molar ratio, for example, monohydrate, dihydrate, trihydrate, tetrahydrate, pentahydrate, or hexahydrate. In some embodiments, the fourth catalyst is a hexahydrate.

In some embodiments, the fourth additive is a tetraalkylammonium salt, such as a tetramethylammonium salt, tetraethylammonium salt, or tetra-n-butylammonium salt. In some embodiments, the fourth additive is a tetra-n-butylammonium salt, such as tetra-n-butylammonium chloride ($n-Bu_4NCl$ or $Bu_4NCl$), tetra-n-butylammonium bromide ($n-Bu4NBr$ or $Bu_4NBr$), or tetra-n-butylammonium iodide ($n-Bu_4NI$ or $Bu_4NI$). In some embodiments, the fourth additive is tetra-n-butylammonium chloride ($n-Bu_4NCl$). In some embodiments, the fourth additive is tetra-n-butylammonium bromide ($n-Bu_4NBr$).

In some embodiments, the fourth catalyst is neodymium chloride (NdCl), and the fourth additive is tetra-n-butylammonium chloride ($n-Bu_4NCl$). In some embodiments, the fourth catalyst is neodymium chloride ($NdCl_3$), and the fourth additive is tetra-n-butylammonium bromide ($n-Bu_4NBr$). In some embodiments, the fourth catalyst is neodymium chloride tetrahydrofuran solvate ($NdCl_3$.THF), and the fourth additive is tetra-n-butylammonium chloride ($n-Bu_4NCl$). In some embodiments, the fourth catalyst is neodymium chloride tetrahydrofuran solvate ($NdCl_3$.THF), and the fourth additive is tetra-n-butylammonium bromide ($n-Bu_4NBr$). In some embodiments, the fourth catalyst is neodymium chloride hexahydrate ($NdCl_3$. $6H_2O$), and the fourth additive is tetra-n-butylammonium chloride ($n-Bu_4NCl$). In some embodiments, the fourth catalyst is neodymium chloride hexahydrate ($NdCl_3$. $6H_2O$), and the fourth additive is tetra-n-butylammonium bromide ($n-Bu_4NBr$). In some embodiments, the fourth catalyst is cerium chloride ($CeCl_3$), and the fourth additive is tetra-n-butylammonium chloride ($n-Bu_4NCl$). In some embodiments, the fourth catalyst is cerium chloride ($CeCl_3$), and the fourth additive is tetra-n-butylammonium bromide ($n-Bu_4NBr$).

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

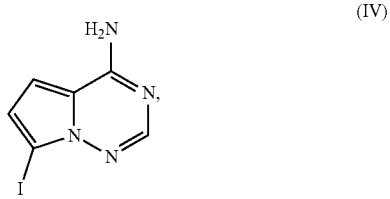 [SMILES: Nc1ncnn2c(I)ccc12]

wherein the third reactor provides a third output mixture; and (d) adding a fourth input mixture to a fourth reactor, wherein the fourth input mixture comprises the third output mixture, neodymium chloride (NdCl₃), tetra-n-butylammonium chloride (n-Bu₄NCl), and a compound of Formula (III):

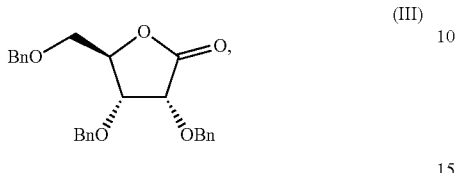

wherein the fourth reactor provides a fourth output mixture comprising the compound of Formula (II-a).

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

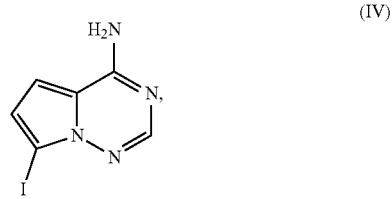 [SMILES: Nc1ncnn2c(I)ccc12]

wherein the third reactor provides a third output mixture; and (d) adding a fourth input mixture to a fourth reactor, wherein the fourth input mixture comprises the third output mixture, neodymium chloride (NdCl₃), tetra-n-butylammonium bromide (n-Bu₄NBr), and a compound of Formula (III):

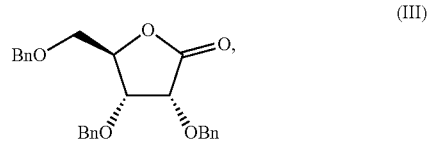 [SMILES: O=C1O[C@H](COCc2ccccc2)[C@@H](OCc2ccccc2)[C@H]1OCc1ccccc1]

wherein the fourth reactor provides a fourth output mixture comprising the compound of Formula (II-a).

Any suitable form of neodymium chloride (NdCl₃) can be used in the method of preparing the compound of Formula (II-a). In some embodiments, the NdCl₃ is anhydrous. In some embodiments, the NdCl₃ is a solvate, for example, with an ether solvent. In some embodiments, the NdCl₃ is neodymium chloride tetrahydrofuran solvate (NdCl₃.THF). In some embodiments, the NdCl₃ is a hydrate. In some embodiments, the NdCl₃ is neodymium chloride hexahydrate (NdCl₃.6H₂O).

Embodiments of the method of preparing the compound of Formula (II-a) using NdCl₃ solvate can also comprise a dehydrating agent. In some embodiments, the dehydrating agent is a trialkyl orthoester, such as trimethyl orthoformate, triethyl orthoformate, triethyl orthoacetate, triethyl orthopropionate, or 3,3,3-triethoxy-1-propyne. In some embodiments, the dehydrating agent is trimethyl orthoformate.

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

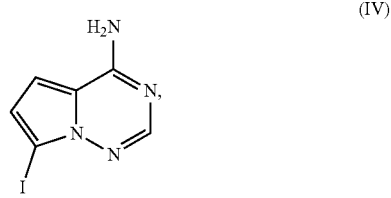 [SMILES: Nc1ncnn2c(I)ccc12]

wherein the third reactor provides a third output mixture; and (d) adding a fourth input mixture to a fourth reactor, wherein the fourth input mixture comprises the third output mixture, neodymium chloride tetrahydrofuran solvate (NdCl₂.THF), tetra-n-butylammonium bromide (n-Bu₄NBr), and a compound of Formula (III):

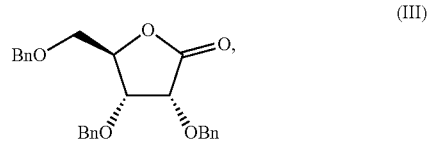 [SMILES: O=C1O[C@H](COCc2ccccc2)[C@@H](OCc2ccccc2)[C@H]1OCc1ccccc1]

wherein the fourth reactor provides a fourth output mixture comprising the compound of Formula (II-a).

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

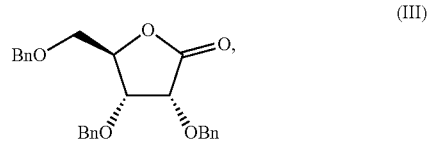 [SMILES: O=C1O[C@H](COCc2ccccc2)[C@@H](OCc2ccccc2)[C@H]1OCc1ccccc1]

wherein the third reactor provides a third output mixture; and (d) adding a fourth input mixture to a fourth reactor, wherein the fourth input mixture comprises the third output mixture, neodymium chloride hexahydrate (NdCl₃. 6H₂O), trimethyl orthoformate, tetra-n-butylammonium bromide (n-Bu₄NBr), and a compound of Formula (III):

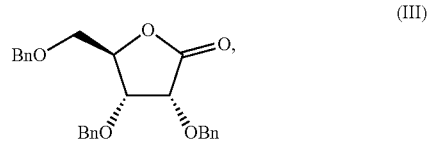 [SMILES: O=C1O[C@H](COCc2ccccc2)[C@@H](OCc2ccccc2)[C@H]1OCc1ccccc1]

wherein the fourth reactor provides a fourth output mixture comprising the compound of Formula (II-a).

In some embodiments, the method further comprises: (c) adding a third input mixture to a third reactor, wherein the third input mixture comprises trimethylsilyl chloride (TMSCl), isopropylmagnesium chloride (iPrMgCl), phenylmagnesium chloride (PhMgCl), tetrahydrofuran (THF), and a compound of Formula (IV):

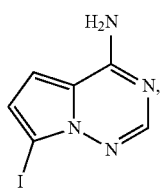
(IV)

wherein the third reactor provides a third output mixture; and (d) adding a fourth input mixture to a fourth reactor, wherein the fourth input mixture comprises the third output mixture, cerium chloride (CeCl$_3$), tetra-n-butylammonium bromide (n-Bu$_4$NBr), and a compound of Formula (III):

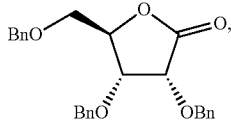
(III)

wherein the fourth reactor provides a fourth output mixture comprising the compound of Formula (II-a).

The method of the present disclosure is amenable to synthesis of gram to kilogram quantities of the compound of Formula (II-a) from the compound of Formula (III). In some embodiments, the fourth input mixture comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (III). In some embodiments, the fourth input mixture comprises at least 1 kg of the compound of Formula (III). In some embodiments, the fourth input mixture comprises from about 50 g to about 100 kg, e.g., from about 50 g to about 20 kg, or from about 30 g to about 20 kg, of the compound of Formula (III). In some embodiments, the fourth input mixture comprises from about 5 kg to about 15 kg of the compound of Formula (III). For example, in some embodiments, the fourth input mixture comprises about 10 kg of the compound of Formula (III).

The compound of Formula (III) having the structure:

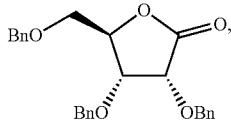
(III)

is also known as (3R,4R,5R)-3,4-bis(benzyloxy)-5-((benzyloxy)methyl)dihydrofuran-2(3H)-one.

The compound of Formula (IV) having the structure:

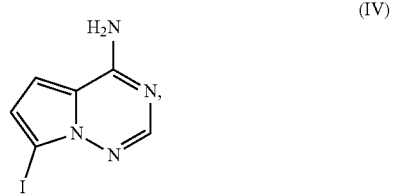 [SMILES: Nc1ncnn2c(I)ccc12]
(IV)

is also known as 7-iodopyrrolo[2,1-f][1,2,4]triazin-4-amine.

2. Formula (II-a) from Formula (V)

In some embodiments, the present disclosure provides a method of preparing a compound of Formula (II-a):

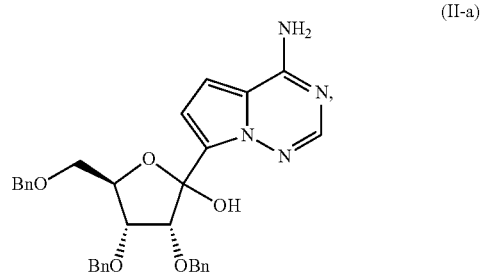 [SMILES: Nc1ncnn2c(C3(O)O[C@H](COCc4ccccc4)[C@@H](OCc4ccccc4)[C@H]3OCc3ccccc3)ccc12]
(II-a)

comprising adding a fifth input mixture to a fifth reactor, wherein the fifth input mixture comprises a compound of Formula (V):

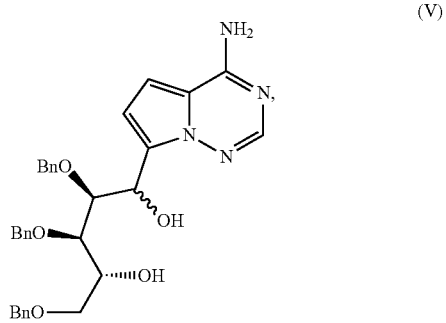 [SMILES: Nc1ncnn2c(C(O)[C@H](OCc3ccccc3)[C@H](OCc3ccccc3)[C@H](O)COCc3ccccc3)ccc12]
(V)

an oxidant, and a fifth base, wherein the fifth reactor provides a fifth output mixture comprising the compound of Formula (II-a).

In some embodiments, the oxidant is (2,2,6,6-tetramethylpiperidin-1-yl)oxyl, 9-azabicyclo[3.3.1]nonane N-oxyl, iodobenzene dichloride, iodobenzene diacetate, sodium hypochlorite, 1,1,1-tris(acetyloxy)-1,1-dihydro-1,2-benziodoxol-3-(1H)-one, dimethyl sulfoxide/pyridine sulfur trioxide, manganese oxide, 2,3-dichloro-5,6-dicyanobenzoquinone, or N-methylmorpholine-N-oxide/tetrapropylammonium perruthenate, or a combination thereof. In some embodiments, the oxidant is (2,2,6,6-tetramethylpiperidin-1-yl)oxyl and iodobenzene diacetate.

In some embodiments, the fifth base is sodium bicarbonate, potassium bicarbonate, sodium carbonate, potassium carbonate, sodium dihydrogen phosphate, potassium dihydrogen phosphate, sodium hydrogen phosphate, potassium hydrogen phosphate, sodium phosphate, potassium phosphate, or ammonium acetate, or a combination thereof. In some embodiments, the fifth base is potassium hydrogen phosphate.

In some embodiments, the fifth input mixture further comprises a fifth solvent selected from the group consisting of dichloromethane, dichloroethane, chloroform, toluene, trifluorotoluene, water, sulfolane, dimethylformamide, N-methylpyrrolidine, dimethyl sulfoxide, methyl acetate, isopropyl acetate, ethyl acetate, and acetonitrile, or a combination thereof. In some embodiments, the fifth solvent is acetonitrile.

In some embodiments, the oxidant is (2,2,6,6-tetramethylpiperidin-1-yl)oxyl and iodobenzene diacetate; the fifth base is potassium hydrogen phosphate; and the fifth solvent is acetonitrile.

The method of preparing the compound of Formula (II-a) can be performed at any suitable temperature. For example, the fifth reactor can be maintained at a temperature of from about −10° C. to about 60° C., or from about 0° C. to about 30° C., or from about 10° C. to about 30° C., such as at about 10° C., about 15° C., about 20° C., about 25° C., or about 30° C. In some embodiments, the fifth reactor is maintained at a temperature of from about −10° C. to about 60° C. In some embodiments, the fifth reactor is maintained at a temperature of from about 10° C. to about 30° C. In some embodiments, the fifth reactor is maintained at a temperature of about 20° C.

In some embodiments, the method further comprises preparing the compound of Formula (V), the method comprising: (a) adding a sixth input mixture to a sixth reactor, wherein the sixth input mixture comprises an amine-protecting agent, a sixth base, and a compound of Formula (IV):

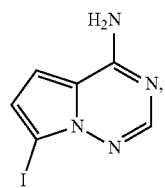

(IV)

wherein the sixth reactor provides an sixth output mixture; (b) adding a seventh input mixture to a seventh reactor, wherein the seventh input mixture comprises the sixth output mixture, a seventh transmetallating agent, and a compound of Formula (VI):

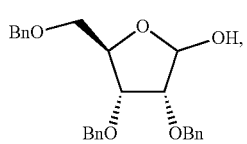

(VI)

wherein the seventh reactor provides a seventh output mixture comprising a compound of Formula (V).

In some embodiments, the amine-protecting agent is chlorotrimethylsilane, chlorotriethylsilane, tert-butyldimethylchlorosilane, tert-butyldiphenylchlorosilane, 1,2-bis(chlorodimethylsilyl) ethane, trifluoroacetic anhydride, or di-(tert-butyl) dicarbonate. In some embodiments, the amine-protecting agent is chlorotrimethylsilane.

In some embodiments, the sixth base is phenylmagnesium chloride, phenylmagnesium bromide, phenylmagnesium iodide, isopropylmagnesium chloride, isopropylmagnesium bromide, tert-butylmagnesium chloride, phenyllithium, methyllithium, isopropyllithium, tert-butyllithium, sodium hydride, potassium hydride, or calcium hydride, or a combination thereof. In some embodiments, the sixth base is phenylmagnesium chloride.

In some embodiments, the sixth input mixture further comprises a sixth solvent selected from the group consisting of tetrahydrofuran (THF), 2-methyltetrahydrofuran, tert-butyl methyl ether, diisopropyl ether, cyclopentyl methyl ether, and toluene, or a combination thereof. In some embodiments, the sixth solvent is tetrahydrofuran (THF).

In some embodiments, the amine-protecting agent is chlorotrimethylsilane; the sixth base is phenylmagnesium chloride; and the sixth solvent is tetrahydrofuran (THF).

The method of preparing the compound of Formula (II-a) can be performed at any suitable temperature. For example, the sixth reactor can be maintained at a temperature of from about −70° C. to about 40° C., or from about −30° C. to about 30° C., or from about −20° C. to about 10° C., such as at about −20° C., about −10° C., about 0° C., or about 10° C. In some embodiments, the sixth reactor is maintained at a temperature of from about −70° C. to about 40° C. In some embodiments, the sixth reactor is maintained at a temperature of from about −20° C. to about 10° C.

In some embodiments, the seventh transmetallating agent is phenylmagnesium chloride, phenylmagnesium bromide, phenylmagnesium iodide, isopropylmagnesium chloride, isopropylmagnesium bromide, tert-butylmagnesium chloride, tert-butylmagnesium bromide, phenyllithium, methyllithium, isopropyllithium, or tert-butyllithium, or a combination thereof. In some embodiments, the seventh transmetallating agent is isopropylmagnesium chloride.

In some embodiments, the seventh input mixture further comprises a seventh solvent selected from the group consisting of tetrahydrofuran (THF), 2-methyltetrahydrofuran, tert-butyl methyl ether, diisopropyl ether, cyclopentyl methyl ether, and toluene, or a combination thereof. In some embodiments, the seventh solvent is tetrahydrofuran (THF).

In some embodiments, the seventh transmetallating agent is isopropylmagnesium chloride; and the seventh solvent is tetrahydrofuran (THF).

The method of preparing the compound of Formula (II-a) can be performed at any suitable temperature. For example, the seventh reactor can be maintained at a temperature of from about −70° C. to about 40° C., or from about −30° C. to about 30° C., or from about −30° C. to about −10° C., such as at about −30° C., about −25° C., about −20° C., or about −10° C. In some embodiments, the seventh reactor is maintained at a temperature of from about −70° C. to about 40° C. In some embodiments, the seventh reactor is maintained at a temperature of from about −30° C. to about −10° C. In some embodiments, the seventh reactor is maintained at a temperature of about −20° C.

The method of the present disclosure is amenable to synthesis of gram to kilogram quantities of the compound of Formula (II-a) from the compound of Formula (V). In some embodiments, the sixth input mixture comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (V). In some embodiments, the sixth input mixture comprises at least 1 kg of the compound of Formula (V). In some embodiments, the sixth input mixture comprises from about 50 g to about 100 kg, e.g., from about 50 g to about 20 kg, or from about 30 g to about 20 kg, of the compound of Formula (V). In some embodiments, the sixth input mixture comprises from about 5 kg to about 15 kg of the compound of Formula (V). For example, in some embodiments, the sixth input mixture comprises about 10 kg of the compound of Formula (V).

The methods of the present disclosure can provide the compound of Formula (II-a) from the compound of Formula (III) or the compound of Formula (V) in any suitable yield. For example, the compound of Formula (II-a) can be prepared in a yield of at least 50%, 55%, 60%, 65%, 70%, 75%, 80%, 85%, 90%, 95%, 97%, 98%, or at least 99%. In some embodiments, the yield of Formula (II-a) is from about 60% to about 100%. In some embodiments, the yield of Formula (II-a) is from about 70% to about 80% or from about 75% to about 85%. In some embodiments, the yield of Formula (II-a) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of Formula (II-a) is about 79%. In some embodiments, the yield of Formula (II-a) is from about 70% to about 90%. In some embodiments, the yield of Formula (II-a) is from about 70% to about 80%. In some embodiments, the yield of Formula (II-a) is from about 75% to about 85%.

The methods of the present disclosure can provide the compound of Formula (II-a) from the compound of Formula (III) or the compound of Formula (V) in any suitable purity. For example, the compound of Formula (II-a) can be prepared in a purity of from about 90% to about 100%, such as from about 95% to about 100% or from about 98% to about 100%. In some embodiments, the purity of the compound of Formula (II-a) is from about 98% to about 100%. In some embodiments, the compound of Formula (II-a) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (II-a) is prepared in a purity of about 99.92%. In some embodiments, the compound of Formula (II-a) is prepared in a purity of from about 95% to about 99.999%, from about 98% to about 99.999%, from about 98% to about 99.99%, or from about 99% to about 99.99%.

C. Formula (Vii) From Formula (I)

Further provided herein are methods of preparing a compound of Formula (VII), (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile:

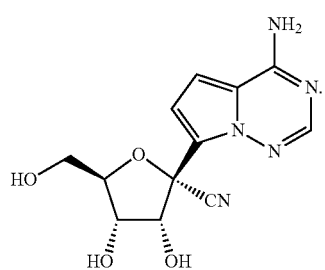

(VII)

The compound of Formula VII can be prepared by a variety of methods described below.

1. Flow Reactor Method

In some embodiments, the present disclosure provides a method of preparing a compound of Formula (VII):

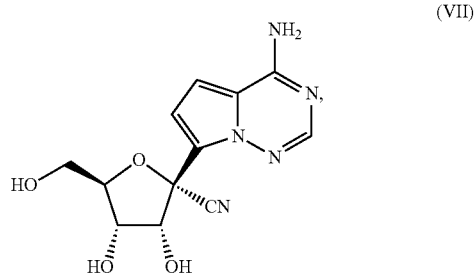 [SMILES: N#C[C@@]1(c2ccc3c(N)ncnn23)O[C@H](CO)[C@@H](O)[C@H]1O]

(VII)

or a salt thereof, the method comprising adding an eighth input mixture to an eighth flow reactor, wherein the eighth input mixture comprises an eighth Lewis acid and a compound of Formula (I):

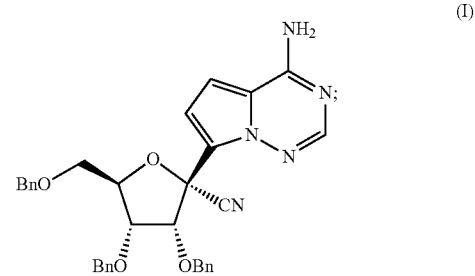 [SMILES: N#C[C@@]1(c2ccc3c(N)ncnn23)O[C@H](COCc2ccccc2)[C@@H](OCc2ccccc2)[C@H]1OCc1ccccc1]

(I)

and the eighth flow reactor provides an eighth output mixture comprising the compound of Formula (VII) or salt thereof.

In some embodiments, the eighth input mixture further comprises an eighth solvent selected from the group consisting of dichloromethane, chloroform, dichloroethane, chlorobenzene, toluene, ethyl acetate (EtOAc), isopropyl acetate (iPrOAc), acetonitrile, tetrahydrofuran (THF), 2-methyltetrahydrofuran, and a combination thereof. In some embodiments, the eighth solvent is dichloromethane.

In some embodiments, the eighth Lewis acid is boron trichloride ($BCl_3$), boron trifluoride ($BF_3$), boron trifluoride diethyl etherate ($BF_3.OEt_2$), boron trifluoride tetrahydrofuran complex ($BF_3.THF$), boron trichloride dimethylsulfide complex ($BCl_3.SMe_2$), or 2-chloro-1,3,2-benzodioxaborole. In some embodiments, the eighth Lewis acid is boron trichloride ($BCl_3$).

The method of preparing the compound of Formula (VII) can be performed at any suitable temperature. For example, the compound of Formula (I) can be cooled to a temperature of from about −20° C. to about 30° C., or from about −10° C. to about 30° C., or from about −10° C. to about 20° C., such as at about −10° C., about −5° C., about 0° C., about 5° C., or about 10° C. In some embodiments, the method further comprises cooling the compound of Formula (I) to a temperature of from about −10° C. to about 20° C. prior to combining with the eighth Lewis acid. In some embodiments, the method comprises cooling the compound of Formula (I) to about 0° C. prior to combining with the eighth Lewis acid.

The method of preparing the compound of Formula (VII) can be performed at any suitable temperature. For example, the eighth Lewis acid can be cooled to a temperature of from about −20° C. to about 20° C., or from about −10° C. to about 20° C., or from about −10° C. to about 10° C., such as at about −10° C., about −5° C., about 0° C., about 5° C., or about 10° C. In some embodiments, the method further comprises cooling the eighth Lewis acid to a temperature of from about −10° C. to about 20° C. prior to combining with the compound of Formula (I). In some embodiments, the method further comprises cooling the eighth Lewis acid to about 0° C. prior to combining with the compound of Formula (I).

The eighth Lewis acid can be present in any suitable concentration. For example, the eighth Lewis acid can be present at a concentration of from 0.1 M to 10 M, or from 0.1 M to 5 M, or from 0.1 M to 2 M, such as about 0.5 M, 0.6, 0.7, 0.8, 0.9, 1, 1.1, 1.2, 1.3, 1.4, or about 1.5 M. In some embodiments, the eighth Lewis acid is at a concentration of from about 0.1 M to about 5 M. In some embodiments, the eighth Lewis acid is at a concentration of from about 0.9 M to about 1.1 M. In some embodiments, the eighth Lewis acid is at a concentration of about 1 M.

In some embodiments, the method comprises combining the compound of Formula (I), and the eighth Lewis acid $BCl_3$ at the concentration of about 1 M in the eighth solvent dichloromethane, to form the eighth input mixture.

In some embodiments, the method comprises continuously adding the eighth input mixture to the eighth flow reactor until the eighth input mixture is exhausted.

In some embodiments, the method comprises a residence time of the eighth input mixture, wherein the residence time of the eighth input mixture in the eighth flow reactor is from about 0.1 to about 10 minutes. In some embodiments, the residence time of the eighth input mixture in the eighth flow reactor is from about 0.5 to about 3 minutes. In some embodiments, the residence time of the eighth input mixture in the eighth flow reactor is from about 135 seconds.

The method of preparing the compound of Formula (VII) can be performed at any suitable temperature. For example, the eighth flow reactor can be maintained at a temperature of from about −20° C. to about 30° C., or from about −10° C. to about 30° C., or from about −10° C. to about 20° C., such as at about −10° C., about −5° C., about 0° C., about 5° C., or about 10° C. In some embodiments, the eighth flow reactor is maintained at a temperature of from about −10° C. to about 20° C. In some embodiments, the eighth flow reactor is maintained at a temperature of about 0° C.

In some embodiments, the method further comprises combining the eighth output mixture and an eighth protic solvent selected from the group consisting of water, methanol, ethanol, n-propanol, isopropanol, n-butanol, tert-butanol, and a combination thereof. In some embodiments, the eighth protic solvent is methanol.

In some embodiments, the method further comprises combining the eighth output mixture with an eighth base. In some embodiments, the eighth base is selected from group consisting of triethylamine, sodium carbonate, potassium carbonate, sodium hydroxide, and potassium hydroxide. In some embodiments, the eighth base is potassium carbonate.

Figure 2:
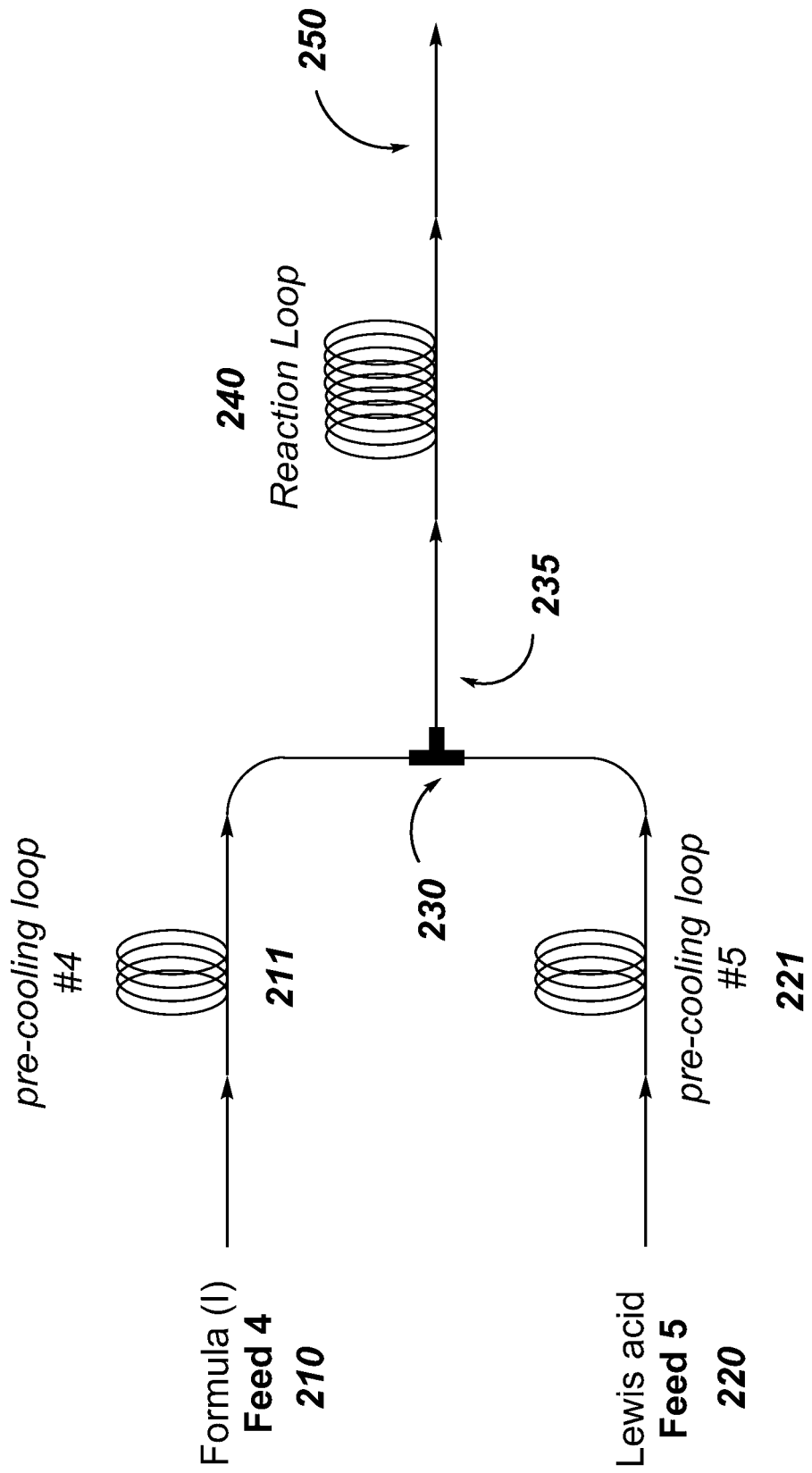
FIG. 2 shows a flow schematic of the method of preparing a compound of Formula (VII) as described in Example 13.

An illustrative diagram of embodiments of the flow reactor method of preparing the compound of Formula (VII) from the compound of Formula (I) described herein is shown in FIG. 2. The fourth feed mixture (Feed 4) (210) comprises the compound of Formula (I) which can be mixed in a suitable solvent such as DCM. Feed 4 is fed into a pre-cooling loop #4 (211) maintained at a seventh temperature. The fifth feed mixture (Feed 5) (220) comprises an eighth Lewis acid, such as $BCl_3$, that can be mixed in a suitable solvent such as DCM. Feed 5 is fed into a pre-cooling loop #5 (221) maintained at the seventh temperature. Feed 4 and Feed 5 are combined at intersection #3 (230) to form an eighth input mixture (235). The eighth input mixture is fed into an eighth flow reactor (240) maintained at an eighth temperature during a third residence time to provide an eighth output mixture (250). The eighth output mixture comprising the compound of Formula (VII) is then fed into an eighth protic solvent, such as methanol. This mixture can undergo workup with an aqueous base, such as potassium carbonate, to provide the compound of Formula (VII).

2. Lewis Acid and Additive Method

In some embodiments, the present disclosure provides a method of preparing a compound of Formula (VII):

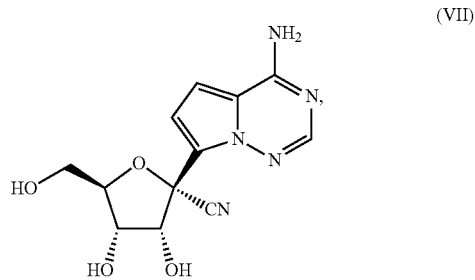 [SMILES: N#C[C@@]1(c2ccc3c(N)ncnn23)O[C@H](CO)[C@@H](O)[C@H]1O]

(VII)

or a salt thereof, the method comprising combining a compound of Formula (I):

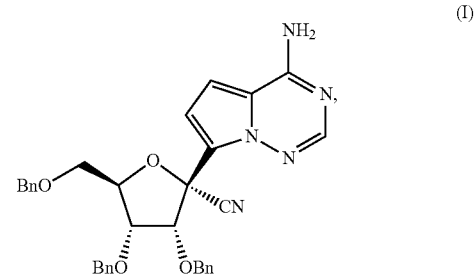 [SMILES: N#C[C@@]1(c2ccc3c(N)ncnn23)O[C@H](COCc2ccccc2)[C@@H](OCc2ccccc2)[C@H]1OCc1ccccc1]

(I)

a ninth Lewis acid, and an additive in a ninth reactor to provide a ninth output mixture comprising the compound of Formula (VII) or salt thereof In some embodiments, the method further comprises a ninth solvent selected from the group consisting of dichloromethane, toluene, ethyl acetate (EtOAc), isopropyl acetate (iPrOAc), acetonitrile, and a combination thereof. In some embodiments, the ninth solvent is dichloromethane.

In some embodiments, the ninth Lewis acid is boron trichloride ($BCl_3$), boron tribromide ($BBr_3$), or boron trifluoride etherate/sodium iodide ($BF_3.OEt_2$/NaI). In some embodiments, the ninth Lewis acid is boron trichloride ($BCl_3$).

The ninth Lewis acid can be present in any suitable amount. For example, the ninth Lewis acid can be present in an amount of at least 1 molar equivalent relative to the compound of Formula (I), such as about 2, about 3, about 4, about 5, about 6, about 7, about 8, about 9, or about 10 molar equivalents. In some embodiments, the ninth Lewis acid is present in an amount of from about 2.0 to about 6.0 molar equivalents relative to the compound of Formula (I). In some embodiments, the ninth Lewis acid is present in an amount of from about 3.0 to about 4.0 molar equivalents relative to the compound of Formula (I). In some embodiments, the ninth Lewis acid is present in an amount of about 3.6 molar equivalents relative to the compound of Formula (I).

In some embodiments, the additive is selected from the group consisting of trialkylborate, triarylborate, methanol, ethanol, isopropanol, and a combination thereof. The trialkylborate can be trimethylborate, triethylborate, triisopropyl borate, tri-n-butylborate, tri(tert-butyl)borate, and the like. The triarylborate can be triphenylborate, tri(o-tolyl)borate, and the like. In some embodiments, the additive is selected from the group consisting of trimethylborate (B(OMe)$_3$), triethylborate (B(OEt)$_3$), triisopropylborate (B(OiPr)$_3$), tri-n-butylborate (B(OBu)$_3$), triphenylborate (B(OPh)$_3$), methanol, ethanol, isopropanol, and a combination thereof. In some embodiments, the additive is trimethylborate (B(OMe)$_3$).

The additive can be present in any suitable amount. For example, the additive can be present in an amount of at least 1 molar equivalent relative to the compound of Formula (I), such as about 2, about 3, about 4, about 5, about 6, about 7, about 8, about 9, or about 10 molar equivalents. In some embodiments, the additive is present in an amount of from about 1.0 to about 4.0 molar equivalents relative to the compound of Formula (I). In some embodiments, the additive is present in an amount of from about 1.5 to about 2.5 molar equivalents relative to the compound of Formula (I). In some embodiments, the additive is present in an amount of about 1.8 molar equivalents relative to the compound of Formula (I).

The ninth Lewis acid, the additive, and the compound of Formula (I) can be combined in any suitable order. For example, the ninth Lewis acid and the additive can be combined with the compound of Formula (I) directly, or combined prior to combining with the compound of Formula (I). Alternatively, one of the ninth Lewis acid and the additive can be combined with the compound of Formula (I) before the other is combined. In some embodiments, the method further comprises combining the ninth Lewis acid and the additive prior to the combining with the compound of Formula (I).

The method of preparing the compound of Formula (VII) can be performed at any suitable temperature. For example, the combining of the ninth Lewis acid and the additive can be at a temperature of from about 0° C. to about 50° C., or from about 10° C. to about 40° C., or from about 10° C. to about 30° C., such as at about 10° C., about 15° C., about 20° C., about 25° C., or about 30° C. In some embodiments, the combining of the ninth Lewis acid and the additive is performed at a temperature of from about 0° C. to about 40° C. In some embodiments, the combining of the ninth Lewis acid and the additive is performed at a temperature of from about 10° C. to about 30° C.

The ninth Lewis acid can be present in any suitable amount. For example, the ninth Lewis acid can be present in an amount of at least 1 molar equivalent relative to the compound of Formula (I), such as about 2, about 3, about 4, about 5, about 6, about 7, about 8, about 9, or about 10 molar equivalents. In some embodiments, the method comprises combining the compound of Formula (I), the ninth Lewis acid boron trichloride (BCl$_3$) in an amount from about 3.0 to about 4.0 molar equivalents relative to the compound of Formula (I), and the additive trimethylborate (B(OMe)$_3$) in an amount from about 1.5 to about 2.5 molar equivalents relative to the compound of Formula (I), in the ninth reactor. In some embodiments, the method comprises combining the compound of Formula (I), the ninth Lewis acid boron trichloride (BCl$_3$) in an amount of about 3.6 molar equivalents relative to the compound of Formula (I), and the additive trimethylborate (B(OMe)$_3$) in an amount of about 1.8 molar equivalents relative to the compound of Formula (I), in the ninth reactor.

The method of preparing the compound of Formula (VII) can be performed at any suitable temperature. For example, the ninth reactor can be maintained at a temperature of from about −20° C. to about 40° C., or from about −10° C. to about 30° C., or from about 0° C. to about 30° C., such as at about 0° C., about 5° C., about 10° C., about 15° C., or about 20° C. In some embodiments, the ninth reactor is maintained at a temperature of from about −20° C. to about 40° C. In some embodiments, the ninth reactor is maintained at a temperature of about 20° C.

In some embodiments, the method further comprises combining the ninth output mixture and a ninth protic solvent selected from the group consisting of water, methanol, ethanol, n-propanol, isopropanol, n-butanol, tert-butanol, and a combination thereof. In some embodiments, the ninth protic solvent is methanol.

In some embodiments, the method further comprises combining the ninth output mixture with a ninth base. In some embodiments, the ninth base is potassium carbonate.

3. Lewis Acid Method

In some embodiments, the present disclosure provides a method of preparing a compound of Formula (VII):

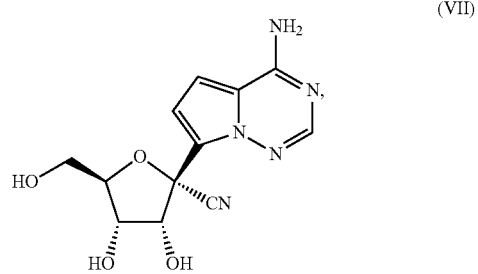 [SMILES: N#C[C@@]1(c2ccc3c(N)ncnn23)O[C@H](CO)[C@@H](O)[C@H]1O]

(VII)

or a salt thereof, the method comprising combining a compound of Formula (I):

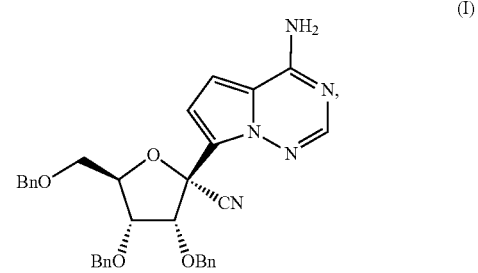 [SMILES: N#C[C@@]1(c2ccc3c(N)ncnn23)O[C@H](COCc2ccccc2)[C@@H](OCc2ccccc2)[C@H]1OCc1ccccc1]

(I)

and a tenth Lewis acid in a tenth reactor to provide a tenth output mixture comprising the compound of Formula (VII) or salt thereof, wherein the tenth Lewis acid is selected from the group consisting of aluminum trichloride ($AlCl_3$), aluminum tribromide ($AlBr_3$), titanium(IV) chloride ($TiCl_4$), and tin(IV) chloride ($SnCl_4$).

In some embodiments, the method further comprises a tenth solvent selected from the group consisting of dichloromethane, anisole, toluene, chlorobenzene, nitrobenzene, trifluorotoluene, tetrahydrofuran (THF), acetone, isopropyl acetate (iPrOAc), acetonitrile, acetic acid, and a combination thereof. In some embodiments, the tenth solvent is dichloromethane, anisole, or a combination thereof.

In some embodiments, the tenth Lewis acid is aluminum trichloride ($AlCl_3$).

In some embodiments, the method further comprises a tenth additive selected from the group consisting of tetrabutylammonium chloride, tetrabutylammonium bisulfite, lithium chloride, magnesium chloride, and a combination thereof In some embodiments, the method further comprises combining the tenth Lewis acid and the tenth solvent prior to combining with the compound of Formula (I).

The tenth Lewis acid can be present in any suitable amount. For example, the tenth Lewis acid can be present in an amount of at least 1 molar equivalent relative to the compound of Formula (I), such as about 2, about 3, about 4, about 5, about 6, about 7, about 8, about 9, or about 10 molar equivalents. In some embodiments, the method further comprises combining the compound of Formula (I) and the tenth Lewis acid aluminum trichloride ($AlCl_3$) in an amount of from about 3.0 to about 5.0 molar equivalents relative to the compound of Formula (I), in the tenth reactor. In some embodiments, the method further comprises combining the compound of Formula (I) and the tenth Lewis acid aluminum trichloride ($AlCl_3$) in an amount of about 4.0 molar equivalents relative to the compound of Formula (I), in the tenth reactor.

The method of preparing the compound of Formula (VII) can be performed at any suitable temperature. For example, the tenth reactor can be maintained at a temperature of from about 0° C. to about 150° C., or from about 0° C. to about 100° C., or from about 0° C. to about 50° C., such as at about 10° C., about 15° C., about 20° C., about 25° C., or about 30° C. In some embodiments, the tenth reactor is maintained at a temperature of from about 0° C. to about 150° C. In some embodiments, the tenth reactor is maintained at a temperature of about 20° C.

In some embodiments, the method further comprises combining the tenth output mixture and a tenth protic solvent selected from the group consisting of water, methanol, ethanol, n-propanol, isopropanol, n-butanol, tert-butanol, and a combination thereof. In some embodiments, the tenth protic solvent is methanol.

In some embodiments, the method further comprises combining the tenth output mixture with a tenth base. In some embodiments, the tenth base is potassium carbonate.

In some embodiments, any of the methods described above further comprises isolating the compound of Formula (VII) or salt thereof The methods of the present disclosure are amenable to synthesis of gram to kilogram quantities of the compound of Formula (VII) from the compound of Formula (I). In some embodiments, the method comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (I). In some embodiments, the method comprises at least 1 kg of the compound of Formula (I). In some embodiments, the method comprises from about 50 g to about 100 kg, e.g., from about 50 g to about 20 kg, or from about 30 g to about 20 kg, of the compound of Formula (I). In some embodiments, the method comprises from about 5 kg to about 15 kg of the compound of Formula (I). For example, in some embodiments, the method comprises about 10 kg of the compound of Formula (I).

The methods of the present disclosure can provide the compound of Formula (VII) in any suitable yield. For example, the compound of Formula (VII) can be prepared in a yield of at least 50%, 55%, 60%, 65%, 70%, 75%, 80%, 85%, 90%, 95%, 97%, 98%, or at least 99%. In some embodiments, the yield of the compound of Formula (VII) is from about 50% to about 100%. In some embodiments, the yield of the compound of Formula (VII) is from about 50% to about 90%. In some embodiments, the yield of the compound of Formula (VII) is from about 50% to about 80%. In some embodiments, the yield of the compound of Formula (VII) is from about 60% to about 100%. In some embodiments, the yield of the compound of Formula (VII) is from about 60% to about 90%. In some embodiments, the yield of the compound of Formula (VII) is from about 70% to about 80% or from about 75% to about 85%. In some embodiments, the yield of the compound of Formula (VII) is from about 70% to about 95%. In some embodiments, the yield of the compound of Formula (VII) is from about 70% to about 90%. In some embodiments, the yield of the compound of Formula (VII) is from about 75% to about 90%. In some embodiments, the yield of the compound of Formula (VII) is from about 75% to about 95%. In some embodiments, the yield of the compound of Formula (VII) is from about 80% to about 95%. In some embodiments, the yield of the compound of Formula (VII) is from about 80% to about 90%. In some embodiments, the yield of the compound of Formula (VII) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (VII) is about 78%. In some embodiments, the yield of the compound of Formula (VII) is from about 70% to about 80%. In some embodiments, the yield of the compound of Formula (VII) is from about 70% to about 90%.

The methods of the present disclosure can provide the compound of Formula (VII) in any suitable purity. For example, the compound of Formula (VII) can be prepared in a purity of from about 90% to about 100%, such as from about 95% to about 100% or from about 98% to about 100%. In some embodiments, the purity of the compound of Formula (VII) is from about 98% to about 100%. In some embodiments, the compound of Formula (VII) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (VII) is prepared in a purity of about 99.9%. In some embodiments, the compound of Formula (VII) is prepared in a purity of from about 95% to about 99.999%, from about 98% to about 99.999%, from about 98% to about 99.99%, or from about 99% to about 99.99%.

In some embodiments, the methods of preparing a compound of Formula (VII) further comprises preparing a compound of Formula (I) by any method described herein.

D. Formula (VIII) From Formula (VII)

Further provided herein are methods of preparing a compound of Formula (VIII), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile:

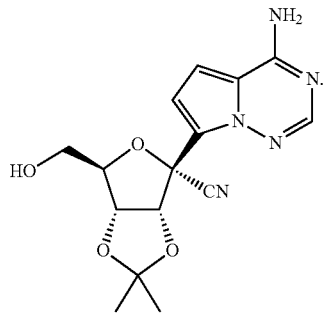
(VIII)

In some embodiments, the present disclosure provides a method of preparing a compound of Formula (VIII):

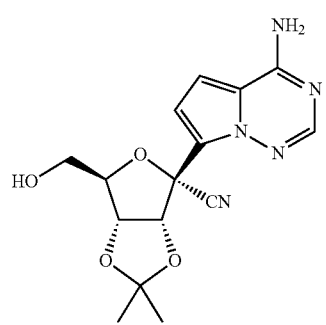
(VIII)

or a pharmaceutically acceptable salt thereof, comprising:

(a) adding an eleventh input mixture to an eleventh reactor, wherein the eleventh input mixture comprises an eleventh acid HX, an eleventh protecting agent, an eleventh solvent, and a compound of Formula (VII):

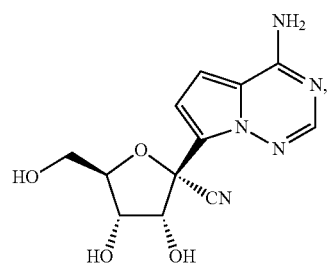
(VII)

wherein the eleventh reactor provides an eleventh output mixture comprising an acid salt of Formula (VIII-a):

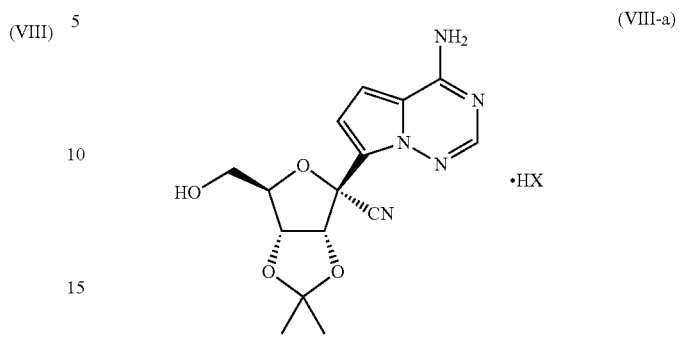
(VIII-a)

wherein the eleventh acid HX is sulfuric acid, hydrochloric acid, phosphoric acid, benzoic acid, oxalic acid, methanesulfonic acid, benzenesulfonic acid, camphorsulfonic acid, naphthalenesulfonic acid, 1-hydroxy-2-naphthoic acid, 1,5-naphthalenedisulfonic acid, maleic acid, ethanesulfonic acid, p-toluenesulfonic acid, or oxalic acid; the eleventh protecting agent is acetone, 2-methoxypropene, or 2,2-dimethoxypropane; and the eleventh solvent is dichloromethane, methyl acetate, ethyl acetate, isopropyl acetate, tetrahydrofuran, 2-methyltetrahydrofuran, or acetonitrile, or a combination thereof and (b) adding a twelfth input mixture to a twelfth reactor, wherein the twelfth input mixture comprises the eleventh output mixture, a twelfth base, and a twelfth solvent; wherein the twelfth reactor provides a twelfth output mixture comprising the compound of Formula (VIII-a); the twelfth base is sodium bicarbonate, sodium carbonate, potassium bicarbonate, potassium carbonate, sodium acetate, potassium acetate, calcium acetate, or calcium hydroxide; and the twelfth solvent is methanol, ethanol, isopropanol, or water, or a combination thereof In some embodiments, the eleventh acid HX is sulfuric acid.

In some embodiments, the eleventh protecting agent is 2,2-dimethoxypropane.

In some embodiments, the eleventh solvent is isopropyl acetate.

In some embodiments, the eleventh acid HX is sulfuric acid; the eleventh protecting agent is 2,2-dimethoxypropane; and the eleventh solvent is isopropyl acetate.

In some embodiments, the twelfth base is potassium acetate.

In some embodiments, the twelfth solvent is methanol.

In some embodiments, the twelfth base is potassium acetate; and the twelfth solvent is methanol.

The method of preparing the compound of Formula (VIII) can be performed at any suitable temperature. For example, the eleventh reactor can be maintained at a temperature of from about 0° C. to about 60° C., or from about 10° C. to about 50° C., or from about 20° C. to about 40° C., such as at about 20° C., about 25° C., about 30° C., about 35° C., or about 40° C. In some embodiments, the eleventh reactor is maintained at a temperature of from about 0° C. to about 60° C. In some embodiments, the eleventh reactor is maintained at a temperature of from about 20° C. to about 40° C.

The method of the present disclosure is amenable to synthesis of gram to kilogram quantities of the compound of Formula (VIII) from the compound of Formula (VII). In some embodiments, the eleventh input mixture comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (VII). In some embodiments, the eleventh input mixture comprises at least 1 kg of the compound of Formula (VII). In some embodiments, the eleventh input mixture comprises from about 50 g to about 100 kg, e.g., from about 50 g to about 20 kg, or from about 30 g to about 20 kg, of the compound of Formula (VII). In some embodiments, the eleventh input mixture comprises from about 5 kg to about 15 kg of the compound of Formula (VII). For example, in some embodiments, the eleventh input mixture comprises about 10 kg of the compound of Formula (VII).

The method of the present disclosure can provide the compound of Formula (VIII) in any suitable yield. For example, the compound of Formula (VIII) can be prepared in a yield of at least 50%, 55%, 60%, 65%, 70%, 75%, 80%, 85%, 90%, 95%, 97%, 98%, or at least 99%. In some embodiments, the yield of the compound of Formula (VIII) is from about 60% to about 100%. In some embodiments, the yield of the compound of Formula (VIII) is from about 60% to about 90%. In some embodiments, the yield of the compound of Formula (VIII) is from about 70% to about 80% or from about 75% to about 85%. In some embodiments, the yield of the compound of Formula (VIII) is from about 70% to about 95%. In some embodiments, the yield of the compound of Formula (VIII) is from about 70% to about 90%. In some embodiments, the yield of the compound of Formula (VIII) is from about 75% to about 90%. In some embodiments, the yield of the compound of Formula (VIII) is from about 75% to about 95%. In some embodiments, the yield of the compound of Formula (VIII) is from about 80% to about 95%. In some embodiments, the yield of the compound of Formula (VIII) is from about 80% to about 90%. In some embodiments, the yield of the compound of Formula (VIII) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (VIII) is about 78%. In some embodiments, the yield of the compound of Formula (VIII) is from about 70% to about 80%. In some embodiments, the yield of the compound of Formula (VIII) is from about 70% to about 90%.

The method of the present disclosure can provide the compound of Formula (VIII) in any suitable purity. For example, the compound of Formula (VIII) can be prepared in a purity of from about 90% to about 100%, such as from about 95% to about 100% or from about 98% to about 100%. In some embodiments, the purity of the compound of Formula (VIII) is from about 98% to about 100%. In some embodiments, the compound of Formula (VIII) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (VIII) is prepared in a purity of about 99.9%. In some embodiments, the compound of Formula (VIII) is prepared in a purity of from about 95% to about 99.999%, from about 98% to about 99.999%, from about 98% to about 99.99%, or from about 99% to about 99.99%.

In some embodiments, the method of preparing a compound of Formula (VIII) further comprises preparing a compound of Formula (VII) by any method described herein.

E. Formula (X) From Formula (VIII)

Further provided herein are methods of preparing a compound of Formula (X), 2-ethylbutyl ((S)-(((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)-L-alaninate:

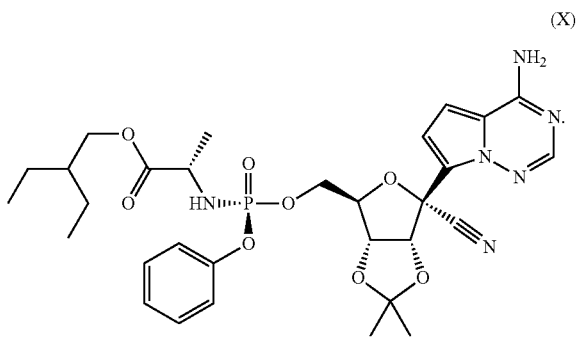 [SMILES: CCC(CC)COC(=O)[C@H](C)N[P@](=O)(OC[C@H]1O[C@@](C#N)(c2ccc3c(N)ncnn23)[C@@H]2OC(C)(C)O[C@@H]21)Oc1ccccc1]

(X)

In some embodiments, the present disclosure provides a method of preparing a compound of Formula (X):

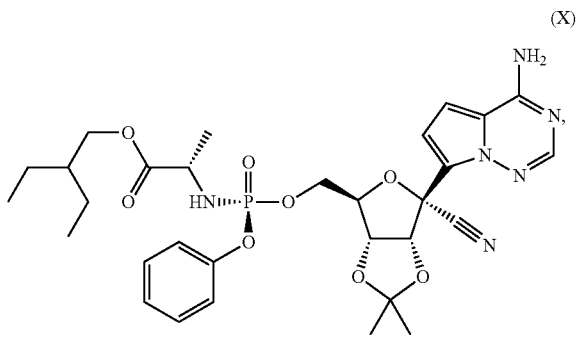 [SMILES: CCC(CC)COC(=O)[C@H](C)N[P@](=O)(OC[C@H]1O[C@@](C#N)(c2ccc3c(N)ncnn23)[C@@H]2OC(C)(C)O[C@@H]21)Oc1ccccc1]

(X)

comprising adding a thirteenth input mixture to a thirteenth reactor, wherein the thirteenth input mixture comprises a compound of Formula (VIII):

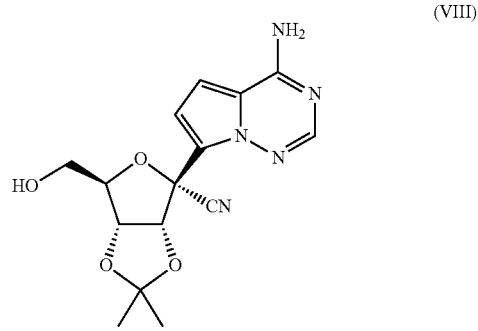 [SMILES: CC1(C)O[C@H]2[C@@H](O1)[C@](C#N)(c1ccc3c(N)ncnn13)O[C@@H]2CO]

(VIII)

or a pharmaceutically acceptable salt thereof, magnesium chloride, diisopropylethylamine, a thirteenth solvent, and a compound of Formula (IX):

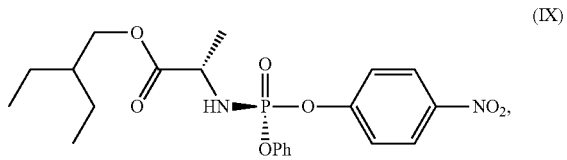

wherein the thirteenth reactor provides an thirteenth output mixture comprising the compound of Formula (X); and the thirteenth solvent is dichloromethane, tetrahydrofuran, or 2-methyltetrahydrofuran, or a combination thereof.

In some embodiments, the thirteenth solvent is tetrahydrofuran.

The method of preparing the compound of Formula (X) can be performed at any suitable temperature. For example, the thirteenth reactor can be maintained at a temperature of from about 0° C. to about 50° C., or from about 10° C. to about 40° C., or from about 10° C. to about 30° C., such as at about 10° C., about 15° C., about 20° C., about 25° C., or about 30° C. In some embodiments, the thirteenth reactor is maintained at a temperature of from about 10° C. to about 30° C.

The method of the present disclosure is amenable to synthesis of gram to kilogram quantities of the compound of Formula (X) from the compound of Formula (VIII). In some embodiments, the method comprises at least 50 g, 100 g, 200 g, 300 g, 400 g, 500 g, 600 g, 700 g, 800 g, 900 g, 1 kg, 2 kg, 3 kg, 4 kg, 5 kg, 10 kg, 20 kg, 30 kg, 40 kg, 50 kg, 100 kg, 200 kg, 500 kg, or at least 1000 kg or more of the compound of Formula (VIII). In some embodiments, the method comprises at least 1 kg of the compound of Formula (VIII). In some embodiments, the method comprises from about 50 g to about 100 kg, e.g., from about 50 g to about 20 kg, or from about 30 g to about 20 kg, of the compound of Formula (VIII). In some embodiments, the method comprises from about 5 kg to about 15 kg of the compound of Formula (VIII). For example, in some embodiments, the method comprises about 10 kg of the compound of Formula (VIII).

The method of the present disclosure can provide the compound of Formula (X) in any suitable yield. For example, the compound of Formula (X) can be prepared in a yield of at least 50%, 55%, 60%, 65%, 70%, 75%, 80%, 85%, 90%, 95%, 97%, 98%, or at least 99%. In some embodiments, the yield of the compound of Formula (X) is from about 60% to about 100%. In some embodiments, the yield of the compound of Formula (X) is from about 60% to about 90%. In some embodiments, the yield of the compound of Formula (X) is from about 70% to about 80% or from about 75% to about 85%. In some embodiments, the yield of the compound of Formula (X) is from about 70% to about 95%. In some embodiments, the yield of the compound of Formula (X) is from about 70% to about 90%. In some embodiments, the yield of the compound of Formula (X) is from about 75% to about 90%. In some embodiments, the yield of the compound of Formula (X) is from about 75% to about 95%. In some embodiments, the yield of the compound of Formula (X) is from about 80% to about 95%. In some embodiments, the yield of the compound of Formula (X) is from about 80% to about 90%. In some embodiments, the yield of the compound of Formula (X) is about 60%, about 70%, about 72%, about 74%, about 75%, about 76%, about 78%, about 80%, about 82%, about 84%, about 85%, about 86%, about 88%, about 90%, about 95%, about 97%, about 98%, or about 99%. In some embodiments, the yield of the compound of Formula (X) is about 78%. In some embodiments, the yield of the compound of Formula (X) is from about 70% to about 80%. In some embodiments, the yield of the compound of Formula (X) is from about 70% to about 90%.

The method of the present disclosure can provide the compound of Formula (X) in any suitable purity. For example, the compound of Formula (X) can be prepared in a purity of from about 90% to about 100%, such as from about 95% to about 100% or from about 98% to about 100%. In some embodiments, the purity of the compound of Formula (X) is from about 98% to about 100%. In some embodiments, the compound of Formula (X) is prepared in a purity of about 90%, about 95%, about 96%, about 97%, about 98%, about 99%, about 99.9%, about 99.99%, about 99.999%, about 99.9999%, or about 99.99999%. In some embodiments, the compound of Formula (X) is prepared in a purity of about 99.9%. In some embodiments, the compound of Formula (X) is prepared in a purity of from about 95% to about 99.999%, from about 98% to about 99.999%, from about 98% to about 99.99%, or from about 99% to about 99.99%.

In some embodiments, the method of preparing a compound of Formula (X) further comprises preparing a compound of Formula (VIII) by any method described herein.

IV. EXAMPLES

Example 1. Synthesis of the Compound of Formula (II-a)

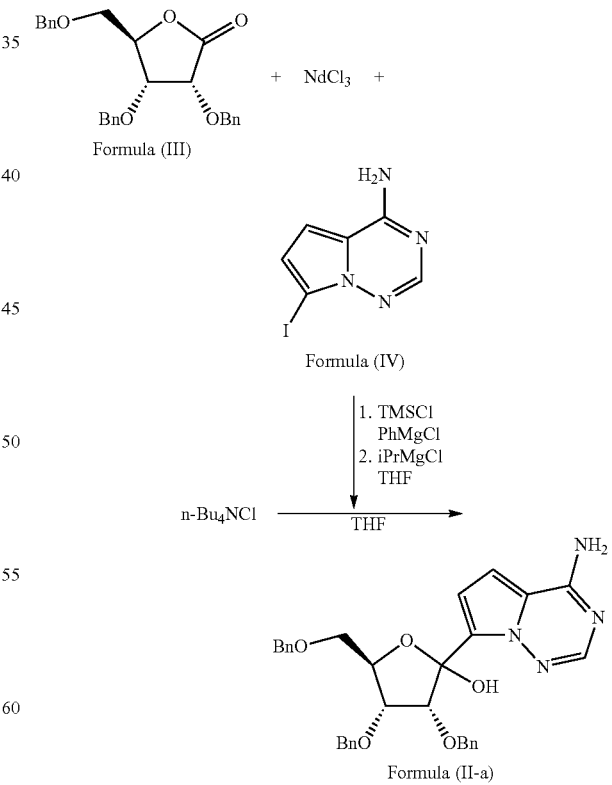

A cylindrical reactor equipped with a retreat-curve overhead agitator, thermocouple, and $N_2$ bubbler was charged anhydrous $NdCl_3$ (60.00 g, 239 mol, 1.00 equiv), n-$Bu_4NCl$ (71.51 g, 239 mmol, 1.00 equiv), and THF (900 g). The resulting mixture was concentrated to about 450 mL at ambient pressure under an $N_2$ pad using a 90° C. jacket temperature. THF (500 g) was charged and the distillation was repeated (twice). The mixture was cooled to 22° C. and the compound of Formula (III) (100.02 g, 239 mmol, 1.00 equiv) was charged. After 30 min the mixture was cooled to −20° C. and held. In a separate reaction flask, the compound of Formula (IV) (68.52 g, 264 mmol, 1.10 equiv) and THF (601 g) were combined and cooled to 0° C. TMSCl (28.64 g, 264 mmol, 1.10 equiv) was added slowly and, after about 30 min the mixture was cooled to 10° C. PhMgCl (2.0 M in THF, 270.00 g, 5.18 mmol, 2.17 equiv) was added slowly and the mixture was agitated for about 30 min and cooled to −20° C. i-PrMgCl (2.0 M in THF, 131.13 g, 269 mmol, 1.13 equiv) was added slowly. After about 2 h, the Grignard reaction mixture was transferred into the lactone/$NdCl_3$/n-$Bu_4$NCl/THF mixture via cannula and the mixture was agitated at about −20° C. After about 16 h, a solution of acetic acid (100 g) in water (440 g) was added and the mixture was warmed to 22° C. i-PrOAc (331 g) was added and the layers were separated. The organic layer was washed with 10% $KHCO_3$ (aq) (2×500 g) and 10% NaCl (aq) (500 g). The organic layer was concentrated to about 450 mL and i-PrOAc (870 g) was charged. The organic mixture was washed with water (2×500 g) and concentrated to about 450 mL. i-PrOAc (435 g) was charged and the mixture was concentrated to about 450 mL. The mixture was filtered and residues were rinsed forward with i-PrOAc (129 g). The filtrate was concentrated to about 250 mL and MTBE (549 g) was charged and the mixture was adjusted to 22° C. Seed crystals (0.15 g) were charged, followed by n-heptane (230 mL) and the mixture was cooled to 0° C. The solids were isolated by filtration and rinsed forward with a mixture of MTBE (113 g) and n-heptane (30 g). The resulting solids were dried under vacuum at 35° C. to afford the compound of Formula (II-a) (79% yield and 99.92% purity).

Example 2. Alternate Synthesis of the Compound of Formula (II-a)

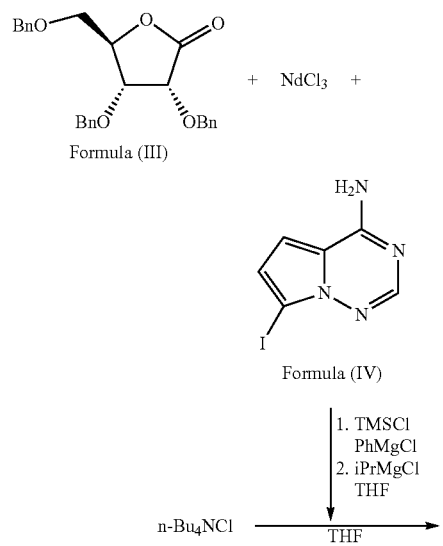

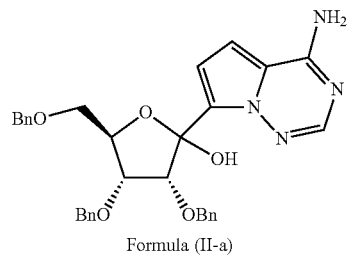

Formula (II-a)

Anhydrous $NdCl_3$ (1.0 equiv), n-$Bu_4$NCl (1.0 equiv), and THF (3.7 g/mmol) are charged under an inert atmosphere. The resulting mixture is concentrated to about half volume at ambient pressure and elevated temperature. THF (1 volume) is charged and the distillation is repeated (twice). The mixture is cooled to room temperature and the compound of Formula (III) (1.0 equiv) is charged. After 30 min the mixture is cooled to −20° C. and held. In a separate reaction flask, the compound of Formula (IV) (1.1 equiv) and THF (8.8 g/mmol) are combined and cooled to 0° C. TMSCl (1.1 equiv) is added slowly and, after about 30 min the mixture is cooled to −10° C. PhMgCl solution in THF (2.17 equiv) is added slowly and the mixture is agitated for about 30 min and cooled to −20° C. i-PrMgCl in THF (1.13 equiv) is added slowly. After about 2 h, the Grignard reaction mixture is transferred into the compound of Formula III/$NdCl_3$/n-$Bu_4$NCl/THF mixture via cannula and the mixture is agitated at about −20° C. After about 16 h, a solution of acetic acid (0.4 g/mmol) in water (1.8 g/mmol) is added and the mixture is warmed to room temperature. i-PrOAc is added and the layers separated. The organic layer is washed with 10% KHCO3 (aq) and 10% NaCl (aq). The organic layer is concentrated to about half volume and i-PrOAc is charged. The organic mixture is washed with water twice and concentrated to about half volume. i-PrOAc is charged and the mixture concentrated to about half volume. The mixture is filtered and residues rinsed forward with i-PrOAc. The filtrate is concentrated to about ¼ volume and MTBE is charged and the mixture adjusted to room temperature. Seed crystals are charged, followed by n-heptane, and the mixture cooled to 0° C. The solids are isolated by filtration and rinsed forward with a mixture of MTBE and n-heptane. The resulting solids are dried under vacuum to afford the compound of Formula (II-a).

Example 3. Synthesis of the Compound of Formula (II-a) with Tetrabutylammonium Bromide

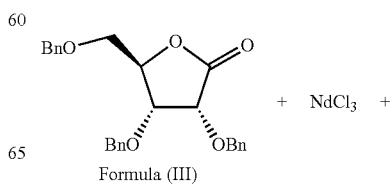

Formula (III)

-continued

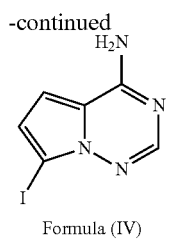

Formula (IV)

1. TMSCl
   PhMgCl
2. iPrMgCl
   THF n-Bu₄NBr ——THF——→

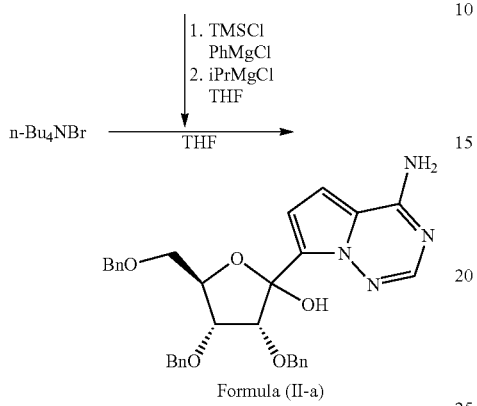

Formula (II-a)

To a reactor was charged anhydrous NdCl₃ (169 kg, 674 mol, 1.00 equiv), n-Bu₄NBr (217 kg, 673 mol, 1.00 equiv), and THF (2865 L). The resulting mixture was concentrated to about 1270 L at ambient pressure under an N₂ pad with a jacket temperature of about 90° C. THF (2865 L) was charged and the distillation was repeated. The mixture was cooled to about 22° C. and the compound of Formula (III) (282 kg, 674 mol, 1.00 equiv) was charged. After about 30 min the mixture was cooled to about −20° C. and held. In a separate reactor, the compound of Formula (IV) (195 kg, 750 mol, 1.11 equiv) and THF (1432 L) were combined and cooled to about 0° C. TMSCl (81.8 kg, 753 mol, 1.12 equiv) was added slowly and, after about 30 min the mixture was cooled to about −10° C. PhMgCl (2.0 M in THF, 761 kg, 1463 mol, 2.17 equiv) was added slowly and the mixture was agitated for about 30 min and cooled to about −20° C. i-PrMgCl (2.0 M in THF, 372 kg, 763 mol, 1.13 equiv) was added slowly. After about 4 h, the Grignard reaction mixture was transferred into the compound of Formula (III)/NdCl₃/n-Bu₄NBr/THF mixture and the mixture was agitated at about −20° C. After about 9 h, a solution of acetic acid (282 kg) in water (1100 L) was added and the mixture was warmed to about 22° C. i-PrOAc (931 kg) was added and the layers were separated. The organic layer was washed sequentially with 10% KHCO3 (aq) (2×1322 L) and a solution of NaCl (141 kg) in water (1269 L). The organic layer was concentrated to about 1270 L and i-PrOAc (2453 kg) was charged. The organic mixture was washed with water (1410 L), filtered and the layers were separated. The organic layer was washed with water (1410 L) and concentrated to about 1270 L. i-PrOAc (2453 kg) was charged and the mixture was concentrated to about 1270 L. The mixture was filtered and residues were rinsed forward with i-PrOAc (367 kg). The filtrate was concentrated to about 845 L and MTBE (1551 kg) was charged and the mixture was adjusted to about 22° C. Seed crystals (0.28 kg) were charged, followed by n-heptane (451 kg) and the mixture was cooled to 0° C. The solids were isolated by filtration and rinsed forward with a mixture of MTBE (310 kg) and n-heptane (85 kg). The resulting solids were dried under vacuum at about 35° C. to afford the compound of Formula (II-a) (86% yield and 98.23% purity).

Example 4. Synthesis of the Compound of Formula (II-a) with Cerium Chloride

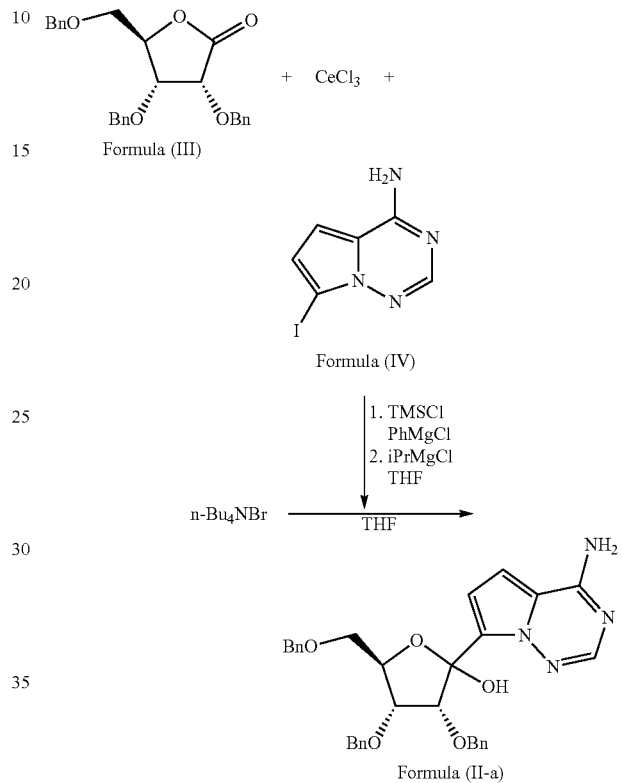

A cylindrical reactor equipped with a retreat-curve overhead agitator, thermocouple, and N₂ bubbler was charged with anhydrous CeCl₃ (12.03 g, 48.8 mmol, 1.02 equiv), n-Bu₄NBr (15.40 g, 47.8 mmol, 1.00 equiv), and THF (180 g). The resulting mixture was concentrated to about 90 mL at ambient pressure under a N₂ pad with a jacket temperature of about 90° C. THF (180 g) was charged and the distillation was repeated. The mixture was cooled to about 22° C. and the compound of Formula (III) (20.03 g, 47.9 mmol, 1.00 equiv) was charged. After about 30 min the mixture was cooled to about −20° C. and held. In a separate reaction flask, the compound of Formula (IV) (13.82 g, 53.2 mol, 1.11 equiv) and THF (90 g) were combined and cooled to about 0° C. TMSCl (5.80 g, 53.4 mmol, 1.12 equiv) was added slowly and, after about 30 min the mixture was cooled to about −10° C. PhMgCl (2.0 M in THF, 54.26 g, 104 mmol, 2.18 equiv) was added slowly and the mixture was agitated for about 30 min and cooled to about −20° C. i-PrMgCl (2.0 M in THF, 26.58 g, 55.0 mol, 1.10 equiv) was added slowly. After about 1 h, the Grignard reaction mixture was transferred into the compound of Formula (III)/CeCl₃/n-Bu₄NBr/THF mixture and the mixture was agitated at about −20° C. After about 15 h, a solution of acetic acid (20.40 g) in water (88 g) was added and the mixture was warmed to about 22° C. i-PrOAc (66 g) was added, the mixture was filtered through a pad of diatomaceous earth and the pad was rinsed with i-PrOAc (28 g). The layers of the biphasic filtrate were separated and the organic layer was washed sequentially with 10% KHCO3 (aq) (2×100 g) and 10% NaCl(aq) (101 g). The organic layer was concentrated to about 60 mL and i-PrOAc (175 g) and water (100 g) were charged. The mixture was filtered through a pad of diatomaceous earth, and the pad was rinsed i-PrOAc (26 g). The layers of the biphasic filtrate were separated and the organic layer was washed with water (100 g). The organic layer concentrated to about 90 mL, and i-PrOAc (175 g) was charged. The mixture was concentrated to about 90 mL and the concentrated mixture was filtered and residues were rinsed forward with i-PrOAc (28 g). The filtrate was concentrated to about 60 mL, MTBE (110 g) was charged and the mixture was adjusted to about 22° C. Seed crystals (0.022 g) were charged, followed by n-heptane (33 g) and the mixture was cooled to 0° C. The solids were isolated by filtration and rinsed forward with a mixture of MTBE (22 g) and n-heptane (6 g). The resulting solids were dried under vacuum at about 35° C. to afford the compound of Formula (II-a) (69% yield and 97.08% purity).

Example 5. Synthesis of the Compound of Formula (II-a) with Neodymium Chloride-Tetrahydrofuran Solvate

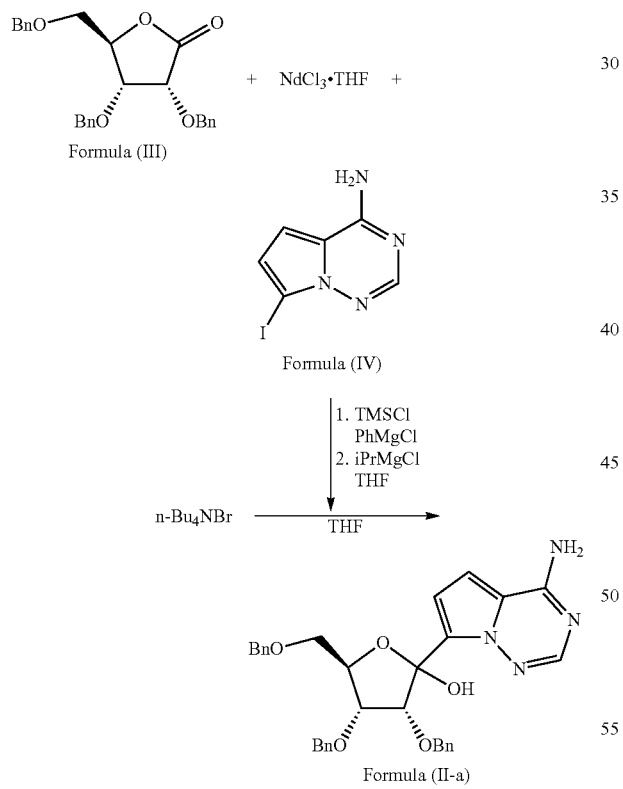

A cylindrical reactor equipped with a retreat-curve overhead agitator, thermocouple, and $N_2$ bubbler was charged with $NdCl_3 \cdot 6H_2O$ (8.74 g, 24.3 mmol, 1.02 equiv) and THF (35 g). Thionyl chloride (23.3 g, 196 mmol, 8.17 equiv) was added slowly and the mixture was agitated for about 1 h. A mixture of anhydrous $NdCl_3$ (0.11 g) in THF (1 g) was added and the mixture was agitated for about 4 h. The mixture was filtered and the solid $NdCl_3 \cdot THF$ was combined with n-$Bu_4NBr$ (7.70 g, 239 mmol, 1.00 equiv) and THF (91 g) in a cylindrical reactor. The resulting mixture was concentrated to about 45 mL at ambient pressure under a $N_2$ pad with a jacket temperature of about 90° C. THF (91 g) was charged and the distillation was repeated. The mixture was cooled to about 22° C. and the compound of Formula (III) (10.0 g, 23.9 mmol, 1.00 equiv) was charged. After about 30 min the mixture was cooled to about −20° C. and held. In a separate reactor, the compound of Formula (IV) (6.91 g, 26.6 mmol, 1.11 equiv) and THF (45 g) were combined and cooled to about 0° C. TMSCl (2.91 g, 26.8 mmol, 1.12 equiv) was added slowly and, after about 30 min the mixture was cooled to about −10° C. PhMgCl (2.0 M in THF, 27.0 g, 52.0 mmol, 2.17 equiv) was added slowly and the mixture was agitated for about 30 min and cooled to about −20° C. i-PrMgCl (2.0 M in THF, 13.5 g, 27.6 mmol, 1.15 equiv) was added slowly. After about 3 h, the Grignard reaction mixture was transferred into the compound of Formula (III)/$NdCl_3THF$/n-$Bu_4NBr$/THF mixture and the mixture was agitated at about −20° C. After about 17 h, a solution of acetic acid (10.7 g) in water (45 g) was added and the mixture was warmed to about 22° C. i-PrOAc (33 g) was added and the layers were separated. The organic layer was washed sequentially with 10% $KHCO_3$ (aq) (2×51 g) and 10% NaCl(aq) (50 g). i-PrOAc (88 g) was charged and the organic layer was concentrated to about 45 mL. i-PrOAc (87 g) and water (50 g) were charged and the mixture was filtered through a pad of diatomaceous earth. The pad was rinsed with i-PrOAc (13 g) and the layers of the biphasic filtrate were separated. The organic layer was washed with water (50 g) and concentrated to about 45 mL. i-PrOAc (87 g) was charged and the mixture was concentrated to about 30 mL. MTBE (55 g) was charged, followed by seed crystals (0.01 g). n-Heptane (16 g) was charged and the mixture was cooled to 0° C. The mixture was filtered and the solids were rinsed with a mixture of MTBE (12 g) and n-heptane (3 g). The resulting solids were dried under vacuum at about 35° C. to afford the compound of Formula (II-a) (43% yield and 98.53% purity).

Example 6. Synthesis of the Compound of Formula (II-a) with Neodymium Chloride Hydrate

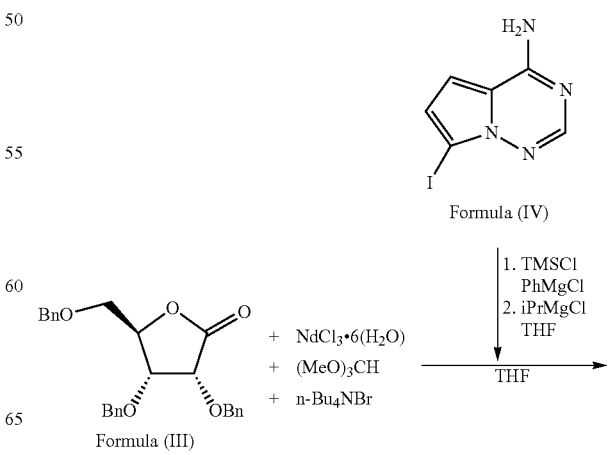

49

-continued

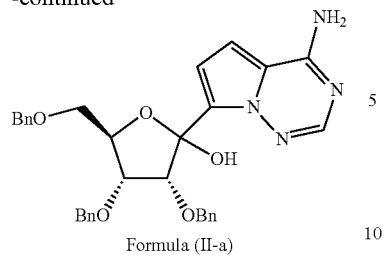

Formula (II-a)

A cylindrical reactor equipped with a retreat-curve overhead agitator, thermocouple, and N₂ bubbler was charged with NdCl₃.6H₂O (17.2 g, 48.1 mmol, 1.17 equiv), THF (180 g) and trimethyl orthoformate (30.7 g, 189 mmol, 7.07 equiv) and the mixture was agitated at about 22° C. for about 2 h. n-Bu₄NBr (15.4 g, 47.8 mmol, 1.17 equiv) was charged and the mixture was concentrated to about 90 mL at ambient pressure under a N₂ pad with a jacket temperature of about 90° C. A sequence of THF (180 g) addition, followed by concentration at ambient pressure under a N₂ pad to about 90 mL was performed three times. The mixture was cooled to about 22° C. and the compound of Formula (III) (17.1 g, 40.9 mmol, 1.00 equiv) was charged. After about 30 min the mixture was cooled to about −20° C. and held. In a separate reactor, the compound of Formula (IV) (11.8 g, 45.4 mmol, 1.11 equiv) and THF (77 g) were combined and cooled to about 0° C. TMSCl (4.97 g, 45.7 mmol, 1.12 equiv) was added slowly and, after about 30 min the mixture was cooled to about −10° C. PhMgCl (2.0 M in THF, 46.5 g, 91.2 mmol, 2.23 equiv) was added slowly and the mixture was agitated for about 30 min and cooled to about −20° C. i-PrMgCl (2.0 M in THF, 22.7 g, 46.5 mmol, 1.14 equiv) was added slowly. After about 4 h, the Grignard reaction mixture was transferred into the compound of Formula (III)/NdCl₃/n-Bu₄NBr/THF mixture and the mixture was agitated at about −20° C. After about 20 h, a solution of acetic acid (17.1 g) in water (76 g) was added and the mixture was warmed to about 22° C. Water (8 g) and i-PrOAc (56 g) was added and the layers were separated. The organic layer was washed sequentially with 10% KHCO₃ (aq) (2×86 g) and 10% NaCl(aq) (86 g). The organic layer was concentrated to about 90 mL and i-PrOAc (149 g) was charged. Water (86 g) was charged and the mixture was filtered through a pad of diatomaceous earth. The pad was rinsed with i-PrOAc (22 g) and the layers of the biphasic filtrate were separated. The organic layer was washed with water (86 g) and concentrated to about 90 mL. i-PrOAc (149 g) was charged and the mixture was concentrated to about 90 mL. The mixture was filtered and residues were rinsed forward with i-PrOAc (22 g). The filtrate was concentrated to about 60 mL and MTBE (94 g) was charged and the mixture was adjusted to about 22° C. Seed crystals (0.02 g) were charged, followed by n-heptane (28 g) and the mixture was cooled to 0° C. The solids were isolated by filtration and rinsed forward with a mixture of MTBE (19 g) and n-heptane (5 g). The resulting solids were dried under vacuum at about 35° C. to afford the compound of Formula (II-a) (65% yield and 86.16% purity).

50

Example 7. Flow Reactor Synthesis of the Compound of Formula (I)

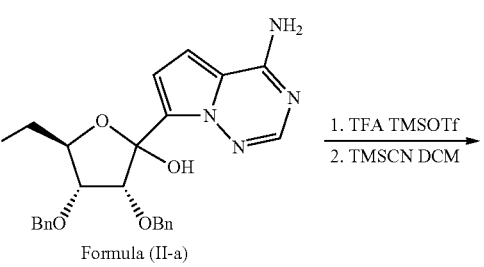

Formula (II-a)

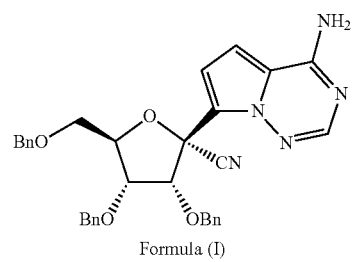

Formula (I)

A reactor was charged with potassium hydroxide (19.7 equiv.) and water (8 volumes). Stock solutions of the compound of Formula (II-a) (250 kg, 1.0 equiv, scaling factor) in dichloromethane (15.0 volumes) (Feed 1), TMSOTf (6.0 equiv) and TFA (1.0 equiv) in dichloromethane (4.4 volumes) (Feed 2), and TMSCN (6.0 equiv) in dichloromethane (4.5 volumes) (Feed 3), were prepared in separate reactors or feed vessels (FIG. 1). Feed 1 was pumped at a flow rate of approximately 504 mL/min through a pre-cooling loop at about −30° C., and Feed 2 was pumped at a flow rate of approximately 207 mL/min. Feeds 1 and 2 were combined in Reaction Loop #1 at about −30° C. for about 30 seconds. The effluent was then combined with Feed 3 (pumping at approximately 189 mL/min through a pre-cooling loop at about −30° C.) in Reaction Loop #2 at about −30° C. for about 2 minutes. The effluent of the combined feeds was collected directly into a vessel containing a solution of aqueous potassium hydroxide at about −10° C. The mixture was adjusted to about 22° C., then 2-propanol was charged and the layers were separated. The organic layer was washed with aqueous sodium chloride twice and concentrated. The resulting solution was filtered. Toluene was charged to the filtrate and the mixture was concentrated. The mixture was heated to about 55° C., then cooled to about 0° C. The resulting slurry was filtered, rinsed with toluene and dried at about 60° C. to afford the compound of Formula (I) in 78% yield with 99.9% purity. ¹H-NMR (400 MHz, DMSO-d6): δ 7.99-7.82 (m, 3H), 7.37-7.23 (m, 15H), 6.88 (d, J=4.5 Hz, 1H), 6.76 (d, J=4.5 Hz,1H), 4.91 (d, J=5.0 Hz, 1H), 4.85 (d, J=11.7 Hz, 1H), 4.77 (d, J=11.7 Hz, 1H), 4.60-4.45 (m, 4H), 4.40 (q, J=4.6 Hz, 1H), 4.12 (t, J=5.4 Hz, 1H), 3.69 (dd, J=11.1, 3.7 Hz, 1H), 3.59 (dd, J=11.1, 4.7 Hz, 1H); δ C-NMR (100 MHz, DMSO-d₆): 8 155.54, 147.86, 138.08, 137.94, 137.32, 128.17, 128.14, 128.11, 127.93, 127.72, 127.52, 127.40, 122.63, 116.78, 116.73, 110.48, 100.81, 81.90, 79.25, 77.61, 76.26, 72.30, 72.27, 71.45, 68.79; HRMS (m/z): [M]+calcd for C₃₃H₃₁N₅O₄, 561.2376; found, 561.2394.

Example 8. Alternate Synthesis of the Compound of Formula (I)

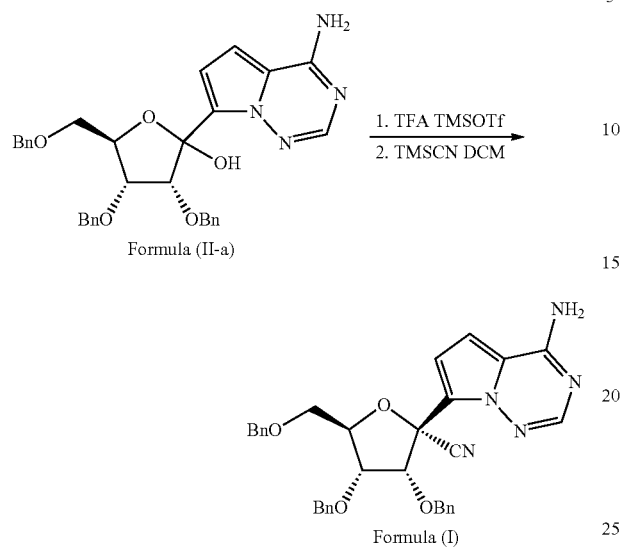

A reactor is charged with potassium hydroxide (19.7 equiv.) and water (8 volumes). Stock solutions of the compound of Formula (II-a) (1.0 equiv, scaling factor) in dichloromethane (15.0 volumes) (Feed 1), TMSOTf (6.0 equiv) and TFA (1.0 equiv) in dichloromethane (4.4 volumes) (Feed 2), and TMSCN (6.0 equiv) in dichloromethane (4.5 volumes) (Feed 3), are prepared in separate reactors or feed vessels (FIG. 1). Feed 1 is pumped through a pre-cooling loop at about −30° C. Feeds 1 and 2 are combined in Reaction Loop #1 at about −30° C. for about 30 seconds. The effluent is then combined with Feed 3 (pumping through a pre-cooling loop at about −30° C.) in Reaction Loop #2 at about −30° C. for about 2 minutes. The effluent of the combined feeds is collected directly into a vessel containing a solution of aqueous potassium hydroxide at about −10° C. The mixture is adjusted to about 22° C., then 2-propanol is charged and the layers separated. The organic layer is washed with aqueous sodium chloride twice and concentrated. The resulting solution is filtered. Toluene is charged to the filtrate and the mixture concentrated. The mixture is heated to about 55° C., then cooled to about 0° C. The resulting slurry is filtered, rinsed with toluene and dried at about 60° C. to afford the compound of Formula (I).

Example 9. Comparative Synthesis of the Compound of Formula (I) without Bronsted Acid Following the same conditions as described in Example 8 above except without trifluoroacetic acid, reaction of the compound of Formula (II-a) at 100-g scale afforded the compound of Formula (I) at 68% isolated yield and 99.4% purity.

Example 10. Synthesis of the Compound of Formula (II-a) from Formula (V)

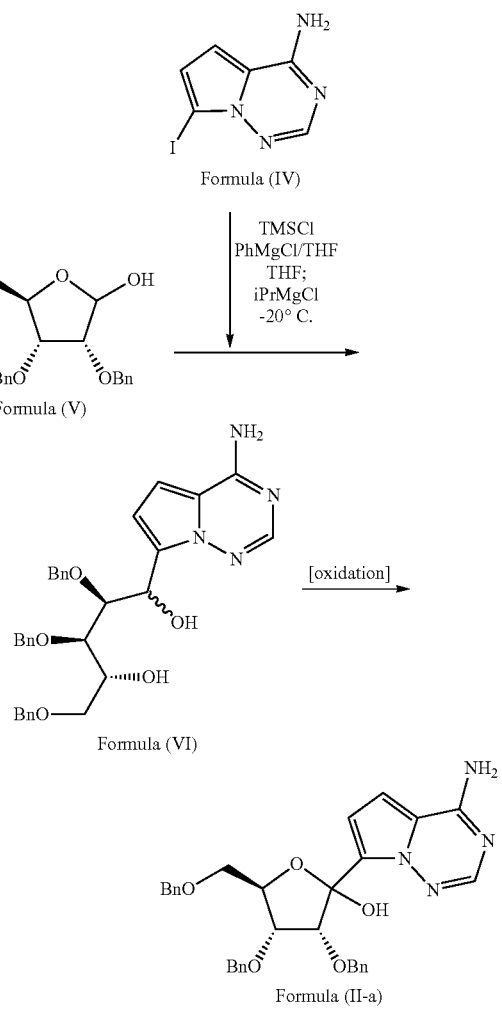

Reactor A was charged with the compound of Formula (IV) (1.2 equiv) and THF (6 volumes) and reactor contents were cooled down to about 0° C. Chlorotrimethylsilane (1.2 equiv) was added to the reaction mixture followed by cooling of the reaction to about −10° C. A solution of phenylmagnesium chloride in THF (2.4 equiv) was added to the mixture, and agitation was continued at about −10° C. The resultant reaction mixture was further cooled to about −20° C. and a solution of isopropylmagnesium chloride in THF (1.0 equiv) was added.

Reactor B was charged with 2,3,5-tri-O-benzyl-D-ribofuranose (Formula (V), 1.0 equiv, scaling factor) and THF (6 volumes) and reactor contents were cooled down to about −20° C. A solution of isopropylmagnesium chloride in THF (1.1 equiv) was added to reactor B. The Grignard reagent generated in reactor A was transferred to reactor B at about −20° C. Reactor and transfer lines were rinsed forward with THF (7 volumes). The reaction mixture was warmed to ambient temperature and the reaction mixture aged for about 17 h. The reaction mixture was then cooled down to about 0° C., and quenched with glacial acetic acid (7.0 equiv) and water (4 volumes). The resulting mixture was extracted with isopropyl acetate (4 volumes). The organic layer was washed twice with 10% w/w potassium bicarbonate solution (5 volumes each time) and finally washed with 10% w/w brine solution (5 volumes). The organic layer was then concentrated to dryness and co-evaporated once with isopropyl acetate (10 volumes) to yield the Formula (VI) compound. Characterization data for the major diastereomer is provided: $^1$H NMR (400 MHz, CD$_3$OD) δ7.67 (s, 1H, Ar-H), 7.38-7.01 (m, 15H, Ar-H), 6.89 (d, J=4.4 Hz, 1H, Ar-H), 6.75 (d, J =4.4 Hz, 1H, Ar-H), 5.55 (d, J=4.0 Hz, 1H, H-1), 4.62 (d, J=11.3 Hz, 1H, Ph-CH$_2$—), 4.53 (d, J=11.3 Hz, 1H, Ph-CH$_2$—), 4.50-4.35 (m, 3H, Ph-CH2—), 4.29 (dd, J=4.3 and 4.3 Hz, 1H, H–2), 4.14 (d, J=11.2 Hz, 1H, Ph-CH$_2$—), 4.09 (ddd, J=3.4 and 5.6 Hz, 1H, H-4), 3.73 (dd, J=5.0 and 5.2 Hz, 1H, H–3), 3.67 (dd, J=3.3 and 10.0 Hz, 1H, H–5a), 3.57 (dd, J=5.8 and 9.9 Hz, 1H, H-5b). 13C NMR (100 MHz, CD$_3$OD) δ155.7, 146.5, 138.3, 138.0, 131.7, 127.92, 127.90, 127.86, 127.77, 127.59, 127.55, 127.21, 127.19, 127.10, 114.1, 109.8, 101.5, 80.1, 79.2, 73.4, 72.9, 72.8, 71.2, 70.3, 66.8. LC-MS analysis on the crude material: m/z=555.5 [M+1].

A reactor was charged with the Formula (VI) compound (1.0 equiv, scaling factor), acetonitrile (52 volumes) and potassium phosphate dibasic (7.0 equiv). Iodobenzene diacetate (3.5 equiv) and (2,2,6,6-tetramethylpiperidin-1-yl)oxyl (TEMPO, 0.2 equiv) were added to the reaction mixture at ambient temperature in one portion and agitation was continued for about 22 h. The reaction mixture was quenched with 3% w/w sodium sulfite solution (28 volumes) and diluted with water (20 volumes) and isopropyl acetate (12 volumes). After about 10 min of agitation, the layers were separated. The organic layer was then concentrated to dryness and the resulting residue was dissolved in isopropyl acetate (17 volumes) and washed with aq. NaCl solution (15 volumes). The organic layer was then concentrated to provide the compound of Formula (II-a): 1H NMR (400 MHz, DMSO-d$_6$) δ8.10 (s, 2H, N—H), 7.98 (s, 1H, Ar-H), 7.35-6.93 (m, 18H, Ar—H), 5.37 (d, 1H, Ar—H), 5.06 (d,1H), 4.58-4.44 (m, 6H, Ph-CH$_2$-), 4.00 (s, 1H), 3.93 (d, 1H), 3.69 (dd, 1H), 3.47 (dd, 1H).

Example 11. Synthesis of the Compound of Formula (VII) with BCl$_3$/B(OMe)$_3$

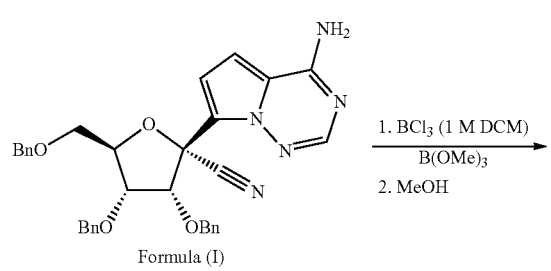

A reactor was charged with boron trichloride (1 M in dichloromethane, 3.6 equiv) and cooled to about 0° C. Trimethyl borate (1.8 equiv) was slowly added to the boron trichloride solution while maintaining a temperature below about 20° C. The solution was then warmed to about 20° C. and stirred for about 1 h. In a separate reactor, Formula (I) (1.0 equiv, scaling factor) was added, followed by dichloromethane (4 volumes) and the mixture cooled to about 0° C. The boron trichloride/trimethyl borate reagent and Formula (I) solution were combined, while maintaining a temperature below 20° C. The boron trichloride/trimethyl borate reagent was rinsed forward with dichloromethane (1 volume), and the mixture was warmed to about 35° C. for about 2 h. In a separate reactor, methanol (7 volumes) was added and cooled to about –15° C. The reaction mixture and methanol solution were combined, while maintaining temperature below about 25° C. The solution was warmed to about 20° C. and stirred for about 12 h. The slurry was filtered and the wet cake was rinsed with dichloromethane (2 volumes). The solids were transferred to a reactor with 20 wt % K$_2$CO$_3$ (0.8 equiv) and the resulting slurry agitated for about 1 h at about 20° C. The slurry was filtered and the cake was rinsed with water (3 volumes) and methanol (1 volume), then dried at about 60° C. to provide the compound of Formula (VII). $^1$H-NMR (400 MHz, H$_2$O-d$_2$): δ8.10 (s, 1H), 7.37 (d, J=5.1 Hz, 1H), 7.14 (d, J=4.8 Hz, 1H), 4.94 (d, J=5.4 Hz, 1H), 4.42 (app q, J=4.2 Hz, 1H), 4.35 (t, J=5.1 Hz, 1H), 3.86 (dd, J=12.8, 3.2 Hz,1H), 3.79 (dd, J=12.8, 4.7 Hz, 1H). $^{13}$C-NMR (100 MHz, DMSO-d$_6$): δ155.62, 147.87, 123.87, 117.34, 116.52, 110.77, 100.79, 85.42, 78.56, 74.24, 70.07, 60.94. HRMS (m/z): [M]$^+$ calc'd. for C$_{12}$H$_{13}$N$_5$O$_4$, 291.0968; found, 291.0967.

The present process can be compared to the previously reported process as shown in Table 1 below.

TABLE 1

| Process | Conditions | Crude Purity | Isolated Yield |
|---|---|---|---|
| Former Process | BCl$_3$, 0° C., 4 h | 53% | 18% |
| Example 11 | BCl$_3$/B(OMe)$_3$, 20° C., 18 h | 88% | 69% |

Example 12. Synthesis of the Compound of Formula (VII) with AlCl₃

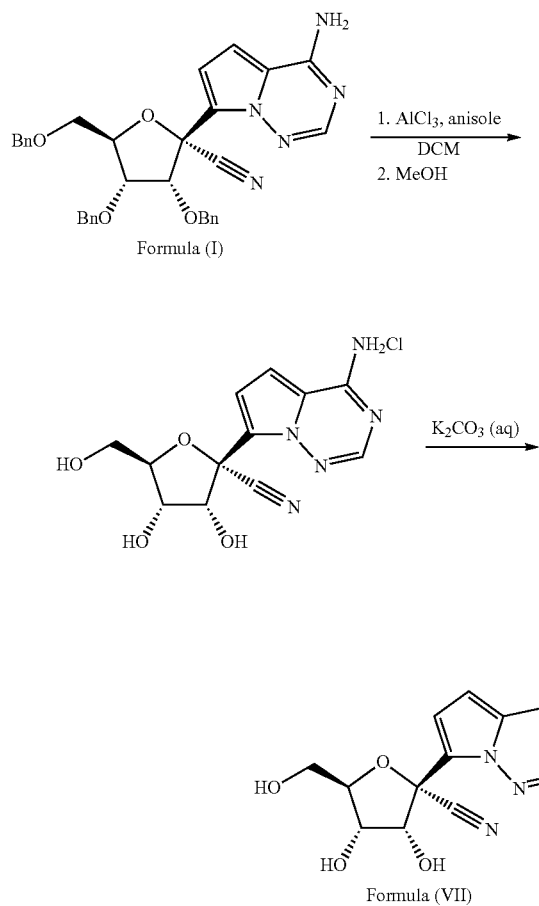

A first reactor was charged with anisole (6 volumes) and dichloromethane (1 volume), and cooled to about 10° C. Aluminum chloride (4.0 equiv) was added in portions, maintaining temperature at about 30° C. The contents were agitated for about 15 min. The compound of Formula (I) (1 equiv) was charged portionwise and rinsed forward with dichloromethane (0.5 volume). The contents were agitated at about 20° C. for about 6 h. In a second reactor, methanol (8 volumes) was added and cooled to about 0° C. The reaction mixture in the first reactor was cooled to about 0° C. followed by the addition of methanol from the second reactor, maintaining temperature about 20° C. The reaction mixture was recirculated between the two reactors until solids were dissolved. The solution was warmed to about 20° C. and stirred for about 12 h. The slurry was filtered and the wet cake was rinsed with MeOH (2 volumes). The solids were transferred to a reactor with 20 wt % $K_2CO_3$ (0.8 equiv) and the slurry agitated for about 1 h at about 20° C. The slurry was filtered and the cake was rinsed with water (3 volumes) and methanol (1 volume), then dried at about 60° C. to provide the compound of Formula (VII).

Example 13. Flow Reactor Synthesis of the Compound of Formula (VII)

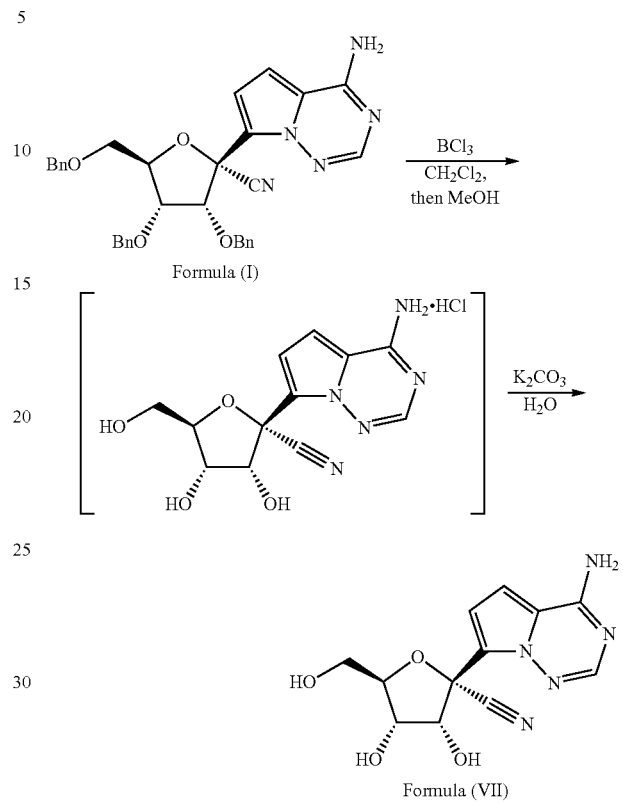

A reactor was charged with Formula (I) (1.0 equiv, scaling factor) and $CH_2Cl_2$ (4.5 volumes) to form a stock solution. This stock solution was then polish filtered and transferred to a fourth feed vessel (Feed 4, 210 of FIG. 2). A solution of $BCl_3$ (1.0 M in $CH_2Cl_2$) was then charged to a fifth feed vessel (Feed 5, 220). Feed 4 was pumped at a flow rate of approximately 12.8 mL/min through a pre-cooling loop at about 0° C., and Feed 5 was pumped at a flow rate of approximately 13.8 mL/min through a pre-cooling loop at about 0° C. Feeds 4 and 5 were combined in the reaction loop (240) at about 0° C. for about 135 seconds (2 minutes 15 seconds). The effluent 250 was collected directly into a vessel containing MeOH (7.0 volumes relative to the compound of Formula (I)) controlled to a temperature of about 0° C. Once collection was complete, the mixture was adjusted to about 20° C. and agitated for about 16 h. The resulting slurry was filtered, rinsed with $CH_2Cl_2$, and pulled dry using vacuum to yield the crude intermediate as a solid. These solids were charged back to the reactor, combined with water, and adjusted to about 20° C. To the resulting slurry, a solution of 20% (w/w) potassium carbonate in water was charged to adjust the pH to about 8–11, and the solution was agitated at about 20° C. for about 1 h. The resulting slurry was filtered, rinsed with water and MeOH and dried at about 60° C. to afford Formula (VII) compound.

Example 14. Synthesis of the Compound of Formula (VIII)

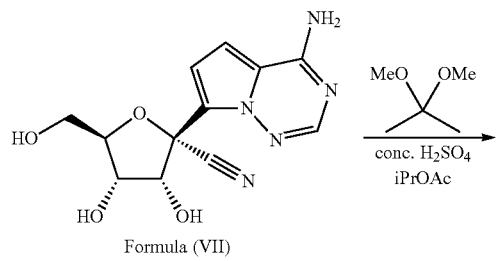

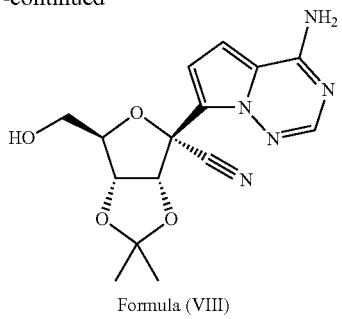

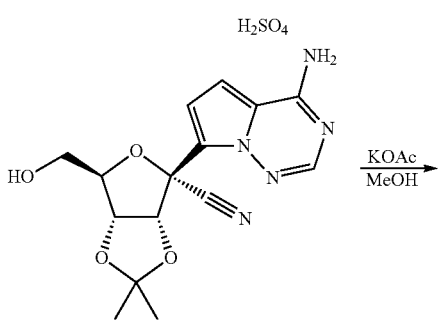

A reactor was charged with Formula (VII) (1.0 equiv, scaling factor) followed by isopropyl acetate (10 volumes), 2,2-dimethoxypropane (5.9 equiv), and cooled to about 20° C. Concentrated sulfuric acid (1.3 equiv) was charged and the reaction was heated to about 30° C. for about 3 h. The reaction mixture was filtered and the cake was rinsed with isopropyl acetate (3 volumes). The intermediate sulfate salt was transferred back to the reactor followed by the addition of potassium acetate (2.0 equiv) and methanol (15 volumes). Water (2 volumes) was then added and the reaction mixture stirred for about 1 hr. The solution was subjected to a carbon treatment followed by a polish filtration. The carbon cartridge was rinsed with methanol (7 volumes). The solution was then distilled to about 3 volumes followed by the addition of water (8 volumes) over about 2 h. The resulting slurry was filtered and the cake was rinsed with water (3 volumes). The solids were dried to yield the compound of Formula (VIII): 1H NMR (400 MHz, DMSO-d6) δ 7.91-7.98 (brm, 5H), 6.95-6.88 (m, 4H), 5.38 (d, J=6.6 Hz, 2H), 5.02 (t, J=5.7 Hz, 2H), 4.90 (dd, J=6.6, 3.1 Hz, 2H), 4.32 (td, J=5.3, 3.0 Hz, 2H), 3.53 (ddq, J=17.3, 11.6, 5.5 Hz, 4H), 1.64 (s, 6H), 1.37 (s, 6H). 13C NMR (100 MHz, DMSO-$d_6$) δ156.05, 148.62, 122.97, 117.42, 116.71, 115.87, 111.05, 101.32, 85.87, 84.37, 82.01, 80.41, 61.35, 26.34, 25.58.

Example 15. Synthesis of the Compound of Formula (X)

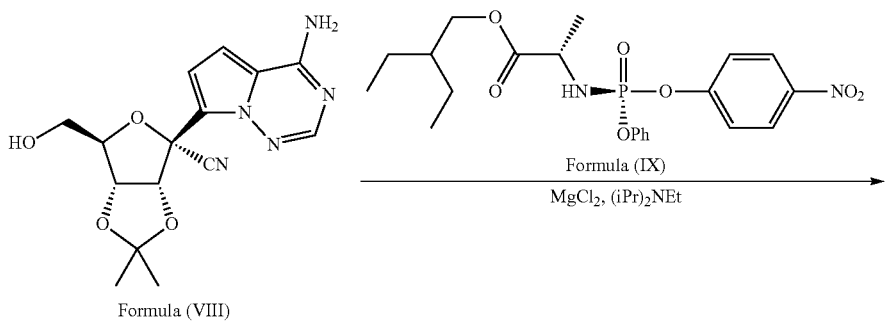

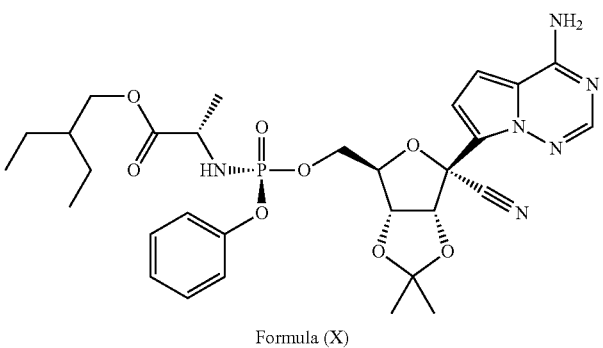

A reactor was charged with Formula (VIII) (1.0 equiv, scaling factor) followed by magnesium chloride (1.5 equiv.) and tetrahydrofuran (10 volumes). This mixture was cooled to about 25° C. N,N-diisopropylethylamine (2.5 equiv.) was charged and the reaction was stirred for about 16 h. at about 25° C. The reaction was quenched into tert-butyl methyl ether (10 volumes) and 10% (w/w) citric acid (10 volumes) at about 10° C. The layers were separated and the organic layer was washed with 10% (w/w) potassium carbonate (15 volumes), 10% (w/w) potassium carbonate (10 volumes), 10% (w/w) ammonium chloride (10 volumes), then 15% (w/w) sodium chloride (10 volumes). The organic layer was distilled to about 3.5 volumes followed by the addition of acetonitrile (10 volumes), distilled to about 3.5 volumes, charged with acetonitrile (7 volumes). The acetonitrile stock solution of Formula (X) was used in the next step.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of Formula (II-a):

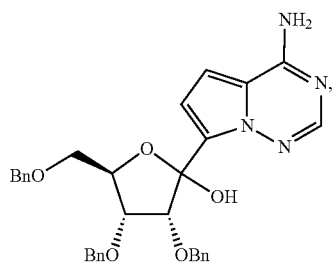

comprising adding a fifth input mixture to a fifth reactor, wherein the fifth input mixture comprises a compound of Formula (V):

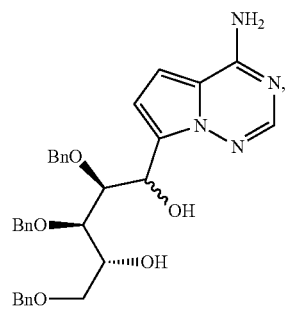

an oxidant, and a fifth base,
wherein the fifth reactor provides a fifth output mixture comprising the compound of Formula (II-a).

2. The method of claim 1, wherein
the oxidant is (2,2,6,6-tetramethylpiperidin-1-yl)oxyl, 9-azabicyclo[3.3.1]nonane N-oxyl, iodobenzene dichloride, iodobenzene diacetate, sodium hypochlorite, 1,1,1-tris(acetyloxy)-1,1-dihydro-1,2-benziodoxol-3-(1H)-one, dimethyl sulfoxide/pyridine sulfur trioxide, manganese oxide, 2,3-dichloro-5,6-dicyanobenzoquinone, or N-methylmorpholine-N-oxide/tetrapropylammonium perruthenate, or a combination thereof.

3. The method of claim 1, wherein the fifth base is sodium bicarbonate, potassium bicarbonate, sodium carbonate, potassium carbonate, sodium dihydrogen phosphate, potassium dihydrogen phosphate, sodium hydrogen phosphate, potassium hydrogen phosphate, sodium phosphate, potassium phosphate, or ammonium acetate, or a combination thereof.

4. The method of claim 1, wherein the fifth input mixture further comprises a fifth solvent selected from the group consisting of dichloromethane, dichloroethane, chloroform, toluene, trifluorotoluene, water, sulfolane, dimethylformamide, N-methylpyrrolidine, dimethyl sulfoxide, methyl acetate, isopropyl acetate, ethyl acetate, and acetonitrile, or a combination thereof.

5. The method of claim 4, wherein
the oxidant is (2,2,6,6-tetramethylpiperidin-1-yl)oxyl and iodobenzene diacetate;
the fifth base is potassium hydrogen phosphate; and
the fifth solvent is acetonitrile.

6. The method of claim 1, wherein the fifth reactor is maintained at a temperature of from about –10° C. to about 60° C.

7. The method of claim 6, wherein the fifth reactor is maintained at a temperature of from about 10° C. to about 30° C.

8. The method of claim 1, further comprising preparing the compound of Formula (V), the method comprising:
(a) adding a sixth input mixture to a sixth reactor, wherein the sixth input mixture comprises an amine-protecting agent, a sixth base, and a compound of Formula (IV):

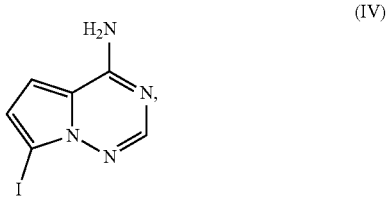

wherein the sixth reactor provides a sixth output mixture;
(b) adding a seventh input mixture to a seventh reactor, wherein the seventh input mixture comprises the sixth output mixture, a seventh transmetallating agent, and a compound of Formula (VI):

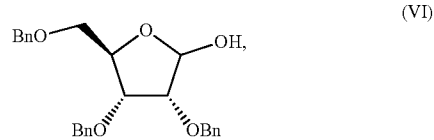 [SMILES: OC1O[C@H](COCc2ccccc2)[C@@H](OCc2ccccc2)[C@H]1OCc1ccccc1]

wherein the seventh reactor provides a seventh output mixture comprising a compound of Formula (V).

9. The method of claim 8, wherein the amine-protecting agent is chlorotrimethylsilane, chlorotriethylsilane, tert-butyldimethylchlorosilane, tert-butyldiphenylchlorosilane, 1,2-bis(chlorodimethylsilyl) ethane, trifluoroacetic anhydride, or di-(tert-butyl) dicarbonate.

10. The method of claim 8, wherein the sixth base is phenylmagnesium chloride, phenylmagnesium bromide, phenylmagnesium iodide, isopropylmagnesium chloride, isopropylmagnesium bromide, tert-butylmagnesium chloride, phenyllithium, methyllithium, isopropyllithium, tert-butyllithium, sodium hydride, potassium hydride, or calcium hydride, or a combination thereof.

11. The method of claim 8, wherein the sixth input mixture further comprises a sixth solvent selected from the group consisting of tetrahydrofuran (THF), 2-methyltetrahydrofuran, tert-butyl methyl ether, diisopropyl ether, cyclopentyl methyl ether, and toluene, or a combination thereof.

12. The method of claim 11, wherein the amine-protecting agent is chlorotrimethylsilane;

the sixth base is phenylmagnesium chloride; and the sixth solvent is tetrahydrofuran (THF).

13. The method of claims 8, wherein the sixth reactor is maintained at a temperature of from about −70° C. to about 40° C.

14. The method of claim 13, wherein the sixth reactor is maintained at a temperature of from about −20° C. to about 10° C.

15. The method of claim 8, wherein the seventh transmetallating agent is phenylmagnesium chloride, phenylmagnesium bromide, phenylmagnesium iodide, isopropylmagnesium chloride, isopropylmagnesium bromide, tert-butylmagnesium chloride, tert-butylmagnesium bromide, phenyllithium, methyllithium, isopropyllithium, or tert-butyllithium, or a combination thereof.

16. The method of claim 8, wherein the seventh input mixture further comprises a seventh solvent selected from the group consisting of tetrahydrofuran (THF), 2-methyltetrahydrofuran, tert-butyl methyl ether, diisopropyl ether, cyclopentyl methyl ether, and toluene, or a combination thereof.

17. The method of claim 16, wherein the seventh transmetallating agent is isopropylmagnesium chloride; and the seventh solvent is tetrahydrofuran (THF).

18. The method of claim 8, wherein the seventh reactor is maintained at a temperature of from about −70° C. to about 40° C.

19. The method of claim 18, wherein the seventh reactor is maintained at a temperature of from about −30° C. to about −10° C.

20. A method of preparing a compound of Formula (II-a):

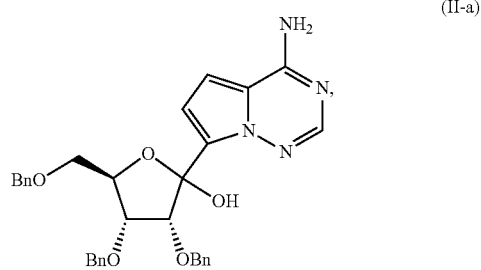 [SMILES: Nc1ncnn2c(C3(O)O[C@H](COCc4ccccc4)[C@@H](OCc4ccccc4)[C@H]3OCc3ccccc3)ccc12]

comprising adding a fifth input mixture to a fifth reactor, wherein the fifth input mixture comprises a compound of Formula (V):

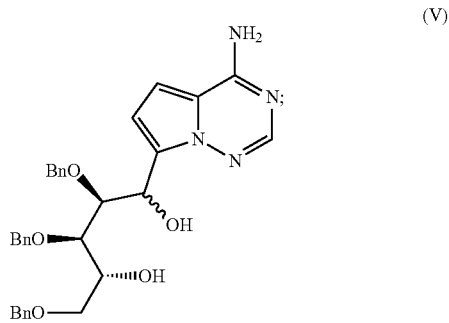 [SMILES: Nc1ncnn2c(C(O)[C@H](OCc3ccccc3)[C@H](OCc3ccccc3)[C@H](O)COCc3ccccc3)ccc12]

an oxidant wherein the oxidant is (2,2,6,6-tetramethylpiperidin-1-yl)oxyl, 9-azabicyclo[3.3.1]nonane N-oxyl, iodobenzene dichloride, iodobenzene diacetate, sodium hypochlorite, 1,1,1-tris(acetyloxy)-1,1-dihydro-1,2-benziodoxol-3-(1H)-one, dimethyl sulfoxide/pyridine sulfur trioxide, manganese oxide, 2,3-dichloro-5,6-dicyanobenzoquinone, or N-methylmorpholine-N-oxide/tetrapropylammonium perruthenate, or a combination thereof;

a fifth base wherein the fifth base is sodium bicarbonate, potassium bicarbonate, sodium carbonate, potassium carbonate, sodium dihydrogen phosphate, potassium dihydrogen phosphate, sodium hydrogen phosphate, potassium hydrogen phosphate, sodium phosphate, potassium phosphate, or ammonium acetate, or a combination thereof; and a fifth solvent wherein the fifth solvent is dichloromethane, dichloroethane, chloroform, toluene, trifluorotoluene, water, sulfolane, dimethylformamide, N-methylpyrrolidine, dimethyl sulfoxide, methyl acetate, isopropyl acetate, ethyl acetate, or acetonitrile, or a combination thereof wherein the fifth reactor provides a fifth output mixture comprising the compound of Formula (II-a).

\* \* \* \* \*

UNITED STATES PATENT AND TRADEMARK OFFICE
CERTIFICATE OF CORRECTION

PATENT NO. : 12,012,431 B2
APPLICATION NO. : 18/108480
DATED : June 18, 2024
INVENTOR(S) : Sankar Mohan Page 1 of 1

It is certified that error appears in the above-identified patent and that said Letters Patent is hereby corrected as shown below:

In the Claims

Column 60, Lines 5-6, Claim 2, delete "1,1,1-tris(acetyloxy)-1,1-dihydro-1,2-benziodoxo1-3-(1H)-one" and insert -- 1,1,1-tris(acetyloxy)-1,1-dihydro-1,2-benziodoxol-3-(1H)-one --.

Column 61, Line 26, Claim 13, delete "claims" and insert -- claim --.

Column 62, Lines 37-38, Claim 20, delete "1,1,1-tris(acetyloxy)-1,1-dihydro-1,2-benziodoxo1-3-(1H)-one" and insert -- 1,1,1-tris(acetyloxy)-1,1-dihydro-1,2-benziodoxol-3-(1H)-one --.

Signed and Sealed this
Twenty-seventh Day of August, 2024

Katherine Kelly Vidal
*Director of the United States Patent and Trademark Office*